United States Patent [19]

Rempfler et al.

[11] Patent Number: 4,973,690
[45] Date of Patent: Nov. 27, 1990

[54] UREAS

[75] Inventors: Hermann Rempfler, Ettingen; Dieter Dürr, Bottmingen, both of Switzerland

[73] Assignee: Ciba-Geigy Corporation, Ardsley, N.Y.

[21] Appl. No.: 332,189

[22] Filed: Apr. 3, 1989

[30] Foreign Application Priority Data

Apr. 12, 1988 [CH] Switzerland ............... 1355/88

[51] Int. Cl.$^5$ .................. A01N 43/54; C07D 239/42
[52] U.S. Cl. ........................ 544/279; 544/253; 544/278; 544/283; 544/297; 544/309; 544/311
[58] Field of Search .............. 71/92; 544/253, 283, 544/278, 279, 297, 309, 311

[56] References Cited

U.S. PATENT DOCUMENTS

| | | | |
|---|---|---|---|
| 4,659,363 | 4/1987 | Hueble et al. | 71/92 |
| 4,694,009 | 9/1987 | Hubele et al. | 514/269 |
| 4,783,459 | 11/1988 | Buhmann et al. | 514/235.8 |
| 4,802,909 | 2/1989 | Rempfler et al. | 71/92 |

FOREIGN PATENT DOCUMENTS

| | | |
|---|---|---|
| 013143 | 7/1980 | European Pat. Off. |
| 065480 | 11/1982 | European Pat. Off. |
| 126296 | 11/1984 | European Pat. Off. |
| 172786 | 2/1986 | European Pat. Off. |
| 151404 | 10/1981 | Fed. Rep. of Germany |

*Primary Examiner*—Mukund J. Shah
*Assistant Examiner*—Carol L. Cseh
*Attorney, Agent, or Firm*—Kevin T. Mansfield; Edward McC. Roberts

[57] ABSTRACT

The present invention relates to novel N-phenyl-N-pyrimidin-2-ylureas having a herbicidal and plant growth-regulating activity, to agrochemical compositions that contain those substances as active ingredients, to the use of the novel ureas for controlling weeds or for regulating plant growth, and to processes for the preparation of the novel compounds. The invention also relates to novel intermediates and to processes for the preparation thereof.

The novel compounds correspond to formula I

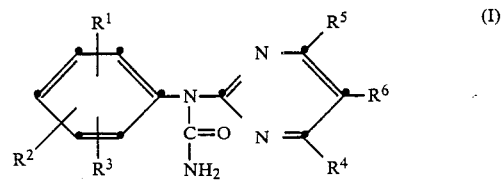

in which the radicals $R^1$ to $R^6$ have the meanings given in the text.

15 Claims, No Drawings

UREAS

The present invention relates to novel N-phenyl-N-pyrimidin-2-ylureas having a herbicidal and plant growth-regulating activity, to agrochemical compositions containing those substances as active ingredients, to the use of the novel ureas for controlling weeds or for regulating plant growth, and to processes for the preparation of the novel compounds. The invention also relates to novel intermediates and to processes for the preparation thereof.

(Pyrimidin-2-yl)-2-nitroanilines are known from Patent Specification DD-151 404 and from European Patent Application EP-A-0 172 786. These compounds are fungicidally active. In contrast, it has surprisingly been found that N-phenyl-N-pyrimidin-2-ylureas have a herbicidal and plant growth-regulating activity.

The invention relates to ureas of formula I

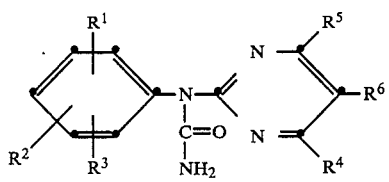

in which $R^1$, $R^2$ and $R^3$ are each, independently of the others, hydrogen; nitro; cyano; halogen; $C_1$-$C_4$alkyl; $C_1$-$C_4$alkyl-S(O)$_n$; $C_1$-$C_4$alkoxy; $C_1$-$C_4$haloalkyl; $C_1$-$C_4$haloalkoxy; $C_1$-$C_4$haloalkyl-S(O)$_n$; $C_1$-$C_4$alkoxycarbonyl; $C_1$-$C_4$alkylcarbonyl; aminocarbonyl; mono-$C_1$-$C_4$alkylaminocarbonyl; or di-$C_1$-$C_4$alkylaminocarbonyl; $R^4$ and $R^5$ are each, independently of the other, hydrogen; $C_1$-$C_4$alkyl; $C_1$-$C_4$alkoxy; $C_1$-$C_4$alkyl-S(O); $C_1$-$C_4$haloalkyl; $C_1$-$C_4$haloalkoxy; $C_1$-$C_4$haloalkyl-S(O)$_n$; phenyl that is unsubstituted or is substituted by up to three identical or different substituents from $C_1$-$C_4$alkyl, halogen, $C_1$-$C_4$alkoxy, $C_1$-$C_4$haloalkyl, nitro and cyano; furanyl; thiophenyl; $C_3$-$C_6$cycloalkyl; $C_1$-$C_4$-alkoxycarbonyl; $C_1$-$C_4$alkoxy-$C_1$-$C_4$alkyl; $C_1$-$C_4$alkoxycarbonyl-$C_1$-$C_4$alkyl; $C_1$-$C_4$alkylcarbonyl-$C_1$-$C_4$alkyl; $C_3$-$C_4$alkenyloxycarbonyl-$C_1$-$C_4$alkyl; $C_3$-$C_4$alkynyloxycarbonyl-$C_1$-$C_4$alkyl; halogen; or cyano;

$R^6$ is $C_1$-$C_4$alkyl; halogen; cyano; $C_3$-$C_6$cycloalkyl; $C_1$-$C_4$haloalkyl; $C_1$-$C_4$alkoxy; nitro; $C_1$-$C_4$alkyl-S(O)$_n$; $C_1$-$C_4$haloalkoxy; $C_1$-$C_4$haloalkyl-S(O)$_n$; or phenyl that is unsubstituted or is substituted by up to three identical or different substituents from halogen, $C_1$-$C_4$alkyl, $C_1$-$C_4$haloalkyl, $C_1$-$C_4$alkyl-S(O)$_n$, $C_1$-$C_4$alkoxy, $C_1$-$C_4$haloalkoxy, nitro and cyano; or $C_1$-$C_4$alkylthio-$C_1$-$C_4$alkyl;

n is 0, 1 or 2; or $R^5$ and $R^6$, together with the two carbon atoms to which they are bonded, are a fused, partially unsaturated, 4- to 8-membered ring which may be substituted by up to three identical or different substituents from $C_1$-$C_4$alkyl, halogen and $C_1$-$C_4$alkoxycarbonyl and/or is interrupted by O, S or N-($C_1$-$C_4$)-alkyl and/or may contain a double bond and/or a carbonyl group; including the salts thereof with acids, bases and complex formers.

Within the scope of the invention disclosed herein, the generic terms used include, for example, the following specific individual substituents, without this list implying any limitation of the invention:

Alkyl includes straight-chained or branched $C_1$-$C_4$alkyl radicals, such as methyl, ethyl, n-propyl, isopropyl, n-butyl, sec.-butyl, tert.-butyl and isobutyl. $C_1$-$C_3$alkyl radicals are preferred.

Halogen is fluorine, chlorine, bromine or iodine. In the case of the substituents $R^4$ to $R^6$, fluorine, chlorine and bromine are preferred and, in the case of the substituents $R^1$ to $R^3$, fluorine, chlorine, bromine and iodine are preferred.

Haloalkyl indicates alkyl radicals, according to the respective scope of definition given, that are completely or partially substituted by identical or different halogen atoms, such as, for example, trifluoromethyl, difluoromethyl, 1,1,2,2-tetrafluoroethyl, 2-chloroethyl, pentafluoroethyl, chlorodifluoromethyl, dichloromethyl, chlorofluoromethyl, 1,1-dichloro-2,2,2-trifluoroethyl, 1,1-dichloroethyl or heptafluoropropyl.

There may be mentioned as $C_1$-$C_4$alkoxycarbonyl radicals, inter alia, methoxycarbonyl, ethoxycarbonyl and the isomeric propoxycarbonyls and butoxycarbonyls.

Alkoxy within the scope of the respective definition of the isomeric alkoxy radicals is especially methoxy, ethoxy, (i)-propoxy, (n)-propoxy, (i)-butoxy, (t)-butoxy, (n)-butoxy and (sec.)-butoxy.

Haloalkoxy within the scope of the respective definition is an isomeric alkyl radical that is mono- or polysubstituted by identical or different halogen atoms, such as, for example, trifluoromethoxy, 2,2,2-trifluoroethoxy, 2,2,3,3,3-pentafluoropropoxy or 1,1,2,2-tetrafluoroethoxy, difluoromethoxy or 2-chloroethoxy.

There may be mentioned as alkoxyalkyl radicals, inter alia, 2-ethoxyethyl, 2-methoxyethyl, 3-methoxypropyl, 2-methoxy-1-methylethyl and methoxymethyl.

The group $C_1$-$C_4$alkyl-S(O)$_n$- represents the respective alkylthio, alkylsulfinyl and alkylsulfonyl radicals. Methylthio, methylsulfinyl, methylsulfonyl, ethylthio, ethylsulfinyl and ethylsulfonyl may be mentioned as being especially preferred.

The group $C_1$-$C_4$haloalkyl-S(O)$_n$- represents the respective haloalkylthio, haloalkylsulfinyl and haloalkylsulfonyl radicals. Difluoromethylthio, difluoromethylsulfinyl, difluoromethylsulfonyl, trifluoromethylthio and chlorofluoromethylthio are especially preferred.

In the case of the group $C_1$-$C_4$alkylthio-$C_1$-$C_4$alkyl, 2-methylthioethyl and 2-ethylthioethyl are to be given special mention.

$C_3$-$C_6$cycloalkyl is cyclopropyl, cyclobutyl, cyclopentyl or cyclohexyl, preferably cyclopropyl, cyclopentyl or cyclohexyl. In the case of radicals $R^4$ to $R^6$ cyclopropyl is preferred.

The phenyl radical mentioned as substituent may be substituted within the scope of the definition given. There may be mentioned as individual substituents, inter alia, unsubstituted phenyl, 2-chlorophenyl, 4-chlorophenyl, 2,4-dichlorophenyl, o-tolyl, p-tolyl, 2-trifluoromethylphenyl and 4-trifluoromethylphenyl.

In cases in which the radicals $R^5$ and $R^6$, together with the two carbon atoms to which they are bonded, form 4- to 8- membered rings, the following ring systems are preferred:

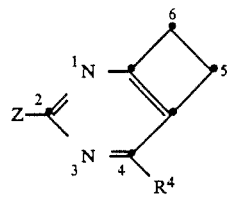

5,6-dihydro-cyclobuta[d]pyrimidines (a)

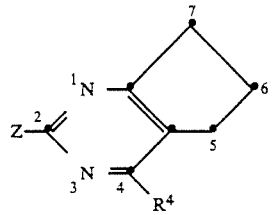

5H-6,7-dihydro-cyclopenta[d]pyrimidines (b)

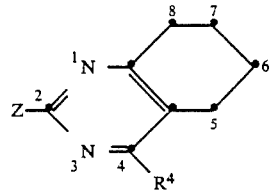

5,6,7,8-tetrahydro-quinazolines (c)

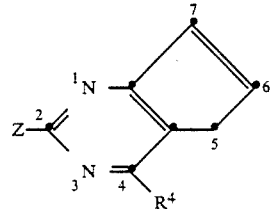

5H-cyclopenta[d]pyrimidines (d)

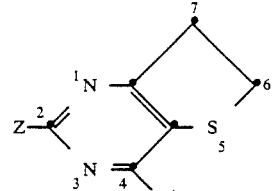

6,7-dihydro-thieno[2,3-d]pyrimidines (e)

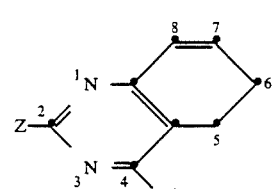

5,6,-dihydro-quinazolines (f)

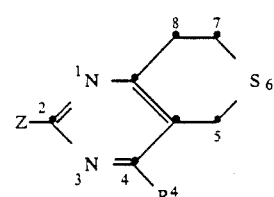

5H-7,8-dihydro-thiopyranol[4,3-d]pyrimidines (g)

-continued

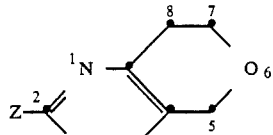

5H-7,8-dihydro-pyrano[4,3-d]pyrimidines (h)

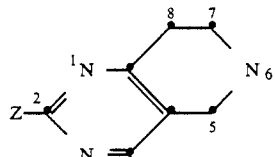

5,6,7,8-tetrahydro-pyrido[4,3-d]pyrimidines (i)

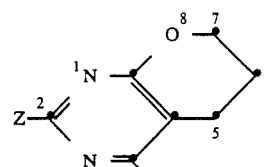

7H-5,6-dihydro-pyrano[2,3-d]pyrimidines (j)

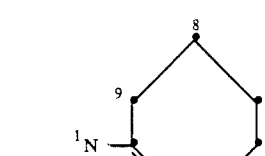

9H-5,6,7,8-tetrahydro-cyclohepta[d]pyrimidines (k)

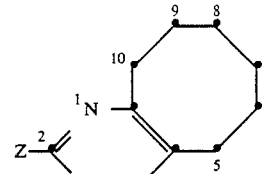

5,6,7,8,9,10-hexahydro-cycloocta[d]pyrimidines (l)

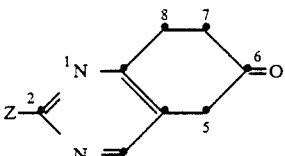

5H-7,8-dihydro-quinoxalines (m)

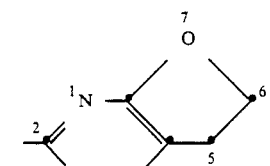

5,6-dihydro-furanol[3,2-e]pyrimidines (n)

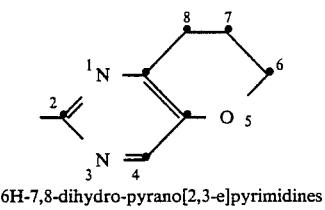

6H-7,8-dihydro-pyrano[2,3-e]pyrimidines

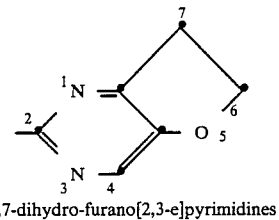

6,7-dihydro-furano[2,3-e]pyrimidines

In the above list of heterocycles, Z represents

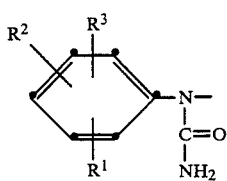

The compounds I containing the heterocycles a to m may be further substituted in the manner indicated in the definition of $R^5$ and $R^6$.

In addition to the unsubstituted radicals a to p, the following may be mentioned as preferred radicals:
6-methyl-5,6-dihydrocyclobuta[d]pyrimidinyl,
5H-7-methyl-6,7-dihydrocyclopenta[d]pyrimidinyl,
7,7-dimethyl-6,7-dihydrocyclopenta[d]pyrimidinyl,
5H-6-methyl-cyclopenta[d]pyrimidinyl,
5H-6-methyl-6,7-dihydrocyclopenta[d]pyrimidinyl,
5H-5-methyl-6,7-dihydrocyclopenta[d]pyrimidinyl,
5H-7-($C_1$-$C_4$alkoxycarbonyl)-6,7-dihydrocyclopenta[d]pyrimidinyl,
5H-6,6-dimethyl-6,7-dihydrocyclopenta[d]pyrimidinyl,
5H-7,7-dimethyl-6,7-dihydrocyclopenta[d]pyrimidinyl,
5H-6,7-dimethyl-6,7-dihydrocyclopenta[d]pyrimidinyl,
5H-7-ethyl-6,7-dihydrocyclopenta[d]pyrimidinyl,
5H-7-ethyl-7-methyl-6,7-dihydrocyclopenta[d]pyrimidinyl,
8-methyl-5,6,7,8-tetrahydroquinazoline,
8,8-dimethyl-5,6,7,8-tetrahydroquinazoline,
7-methyl-5,6,7,8-tetrahydroquinazoline,
5-methyl-5,6,7,8-tetrahydroquinazoline,
6-methyl-5,6,7,8-tetrahydroquinazoline,
6,6-dimethyl-5,6,7,8-tetrahydroquinazoline,
5,7-dimethyl-5,6-dihydroquinazoline,
6-methyl-5,6,7,8-tetrahydropyrido[4,3-d]pyrimidine,
8-($C_1$-$C_4$alkoxycarbonyl)-5,6,7,8-tetrahydroquinazoline,
6,8,8-trimethyl-5,6,7,8-tetrahydroquinazoline,
9H-9-methyl-5,6,7,8-tetrahydrocyclohepta[d]pyrimidine,
9H-9,9-dimethyl-5,6,7,8-tetrahydrocyclohepta[d]pyrimidine,
6-chloro-5,6,7,8-tetrahydroquinazoline.

In the further substituents that are composed of several base elements, the sub-elements may be freely selected within the scope of the definition and have the above meaning.

Attention is drawn to compounds of formula I that are unsubstituted in the 4-position of the phenyl ring

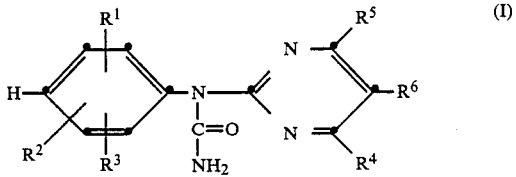

in which the radicals $R^1$ to $R^6$ are as defined hereinbefore.

The invention relates especially to compounds of formula I

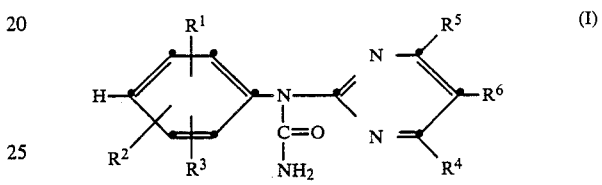

in which $R^1$ is hydrogen; nitro; cyano; halogen; $C_1$-$C_4$alkyl; $C_1$-$C_4$-alkyl-S(O)$_n$; $C_1$-$C_4$alkoxy; $C_1$-$C_4$haloalkyl; $C_1$-$C_4$haloalkoxy; $C_1$-$C_4$haloalkyl-S(O)$_n$; $C_1$-$C_4$alkoxycarbonyl; $C_1$-$C_4$alkylcarbonyl; aminocarbonyl; mono-$C_1$-$C_4$alkylaminocarbonyl; or di-$C_1$-$C_4$alkylaminocarbonyl;

$R^2$ is hydrogen; nitro; halogen; $C_1$-$C_4$alkyl; or $C_1$-$C_4$haloalkyl;

$R^3$ is hydrogen; halogen; or $C_1$-$C_4$alkyl and $R^4$ to $R^6$ and n are as defined hereinbefore.

Preferred are compounds of formula I

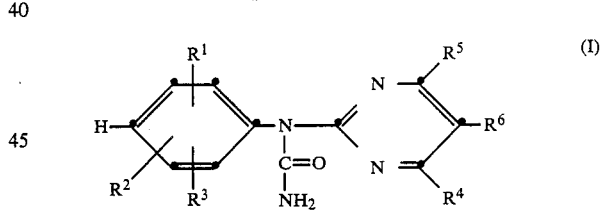

in which $R^1$ is hydrogen; nitro; cyano; halogen; $C_1$-$C_3$alkyl; $C_1$-$C_2$-alkyl-S(O)$_n$; $C_1$-$C_2$haloalkyl-S(O)$_n$; $C_1$-$C_3$alkoxy; $C_1$-$C_2$haloalkyl; $C_1$-$C_2$haloalkoxy; $C_1$-$C_3$alkoxycarbonyl; or dimethylaminocarbonyl;

$R^2$ is hydrogen; nitro; fluorine; chlorine; bromine; or $C_1$-$C_3$alkyl;

$R^3$ is hydrogen; chlorine; or $C_1$-$C_3$alkyl;

$R^4$ hydrogen; $C_1$-$C_4$alkyl; $C_1$-$C_3$alkoxy; $C_1$-$C_4$alkyl-S(O)$_n$-; $C_1$-$C_3$haloalkyl;

$C_1$-$C_2$haloalkoxy; phenyl; chlorophenyl; furanyl; $C_3$-$C_6$cycloalkyl; $C_1$-$C_4$alkoxycarbonyl-$C_1$-$C_2$-alkyl; $C_1$-$C_2$alkoxy-$C_1$-$C_2$alkyl; $C_1$-$C_2$haloalkylthio; chlorine; cyano; or acetonyl;

$R^5$ is hydrogen; $C_1$-$C_3$alkyl; $C_1$-$C_3$alkoxy; halogen; $C_1$-$C_3$haloalkyl; or $C_1$-$C_3$haloalkoxy;

$R^6$ is $C_1$-$C_3$alkyl; $C_1$-$C_3$alkoxy; $C_1$-$C_3$haloalkyl; $C_1$-$C_3$haloalkoxy; chlorine, bromine; $C_1$-$C_3$alkylthio; cyano; nitro; $C_1$-$C_2$alkoxy-$C_1$-$C_2$alkyl; phenyl; chlorophenyl; $C_1$-$C_3$alkoxycarbonyl; $C_1$-$C_2$alkylthio-$C_1$-$C_2$alkyl; or $C_1$-$C_2$cycloalkyl;

n is 0, 1 or 2;

$R^5$ and $R^6$ together are a —CH₂CH₂—, —CH₂—CH₂—CH₂—, —CH₂—CH₂—CH₂—CH₂—, —CH₂—CH₂—CO—CH₂—, —CH=CH—CH₂—, —CH=CH—CH₂—CH₂—, O—CH₂—CH₂—CH₂—, —CH₂—CH₂—S—, —CH₂—CH₂—S—CH₂—, —O—CH₂—CH₂—, —(CH₂)₅—, —(CH₂)₆—, —CH₂—CH₂—CH₂—O—, —CH₂—CH₂—O—, —CH₂—CH₂—O—CH₂— or —CH₂—CH₂—N($C_1$-$C_3$alkyl)—CH₂— bridge, each of which is unsubstituted or is substituted by up to three $C_1$-$C_3$alkyl radicals or by one methoxy or $C_1$-$C_3$alkoxycarbonyl radical or one chlorine atom.

Special prominence should be given to compounds of formula I

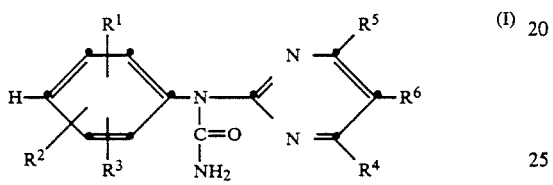

in which $R^1$ is nitro; cyano; halogen; methyl; ethyl; $C_1$-$C_3$haloalkyl; $C_1$-$C_2$alkyl-S(O)$_n$—, $C_1$-$C_2$haloalkyl-S(O)$_n$; methoxy; ethoxy; $C_1$-$C_3$haloalkyl; halomethoxy; $C_1$-$C_3$alkoxycarbonyl; or dimethylaminocarbonyl;

n is 0, 1 or 2;

$R^2$ is hydrogen; fluorine; chlorine; bromine; nitro; or methyl;

$R^3$ is hydrogen; chlorine; or methyl;

$R^4$ is $C_1$-$C_4$alkyl; $C_1$-$C_3$alkoxy; $C_1$-$C_4$alkylthio; methylsulfinyl; ethylsulfinyl; methylsulfonyl; ethylsulfonyl; $C_3$-$C_6$cycloalkyl; chlorine; cyano; $C_1$-$C_3$haloalkyl; methoxymethyl; methoxycarbonylmethyl; acetonyl; phenyl; 4-chlorophenyl; or 2-furanyl;

$R^5$ is $C_1$-$C_2$alkyl; chlorine; $C_1$-$C_3$haloalkyl; or halomethoxy;

$R^6$ is $C_1$-$C_3$alkyl; methoxy; ethoxy; $C_1$-$C_2$haloalkyl; chlorine; bromine; $C_1$-$C_3$alkylthio; cyano; nitro; $C_1$-$C_2$alkoxy-$C_1$-$C_2$alkyl; phenyl; 4-chlorophenyl; $C_1$-$C_2$alkoxycarbonyl; 2-methylthioethyl; or $C_3$-$C_6$cycloalkyl; or $R^5$ and $R^6$ together are —(CH₂)₃—, —CHCH₃—CH₂—CH₂—, —C(CH₃)₂—CH₂—CH₂—, —CH₂—CH(CH₃)—CH₂—, —CH₂—CH₂—CH(CH₃)—, —CH(COOCH₃)—CH₂—CH₂—, —CH(COOC₂H₅)—CH₂—CH₂—, —CH₂—C(CH₃)₂—CH₂—, —CH₂—CH₂—C(CH₃)₂—, —CH(CH₃)—CH(CH₃)—CH₂—, —CH(C₂H₅)—CH₂—CH₂—, —C(CH₃)(C₂H₅)—CH₂—CH₂—, —CH₂—CH₂—CH(CH₃)—CH₂—, —C(CH₃)=CH—CH₂—, —CH₂—CH₂—S—, —(CH₂)₄—, —CH(CH₃)—(CH₂)₃—, —C(CH₃)₂—(CH₂)₃—, —CH₂—CH(CH₃)—(CH₂)₂—, —(CH₂)₃—CH(CH₃)—, —(CH₂)₂—CH(CH₃)—CH₂—, —(CH₂)₂—C(CH₃)₂—CH₂—, —CH(CH₃)—CH₂—C(CH₃)₂—CH₂—, —(CH₂)₂—CO—CH₂—, —(CH₂)₂—CHCl—CH₂—, —C(CH₃)=CH—CH₂—C(CH₃)₂—, —(CH₂)₂—S—CH₂—, —(CH₂)₂—O—CH₂—, —(CH₂)₂—N(CH₃)—CH₂—, —O—(CH₂)₂—, —O—(CH₂)₃—, —(CH₂)₅—, —CH(CH₃)—(CH₂)₄—, —C(CH₃)₂—(CH₂)₄—, —(CH₂)₆—, —(CH₂)₃—O— or —(CH₂)₂—O—.

In view of their biological activity, attention is drawn in addition to the following compounds of formulae Ia to Ig, which have the following substitution pattern in the phenyl ring:

Compounds of formulae Ia to Ig

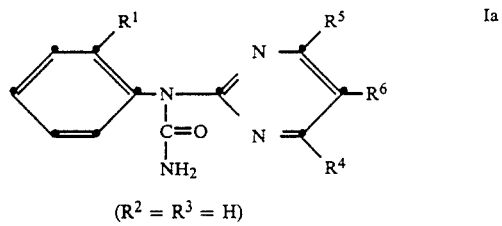

($R^2 = R^3 = H$)

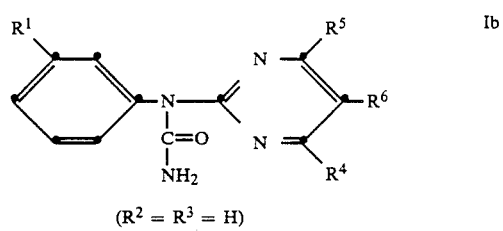

($R^2 = R^3 = H$)

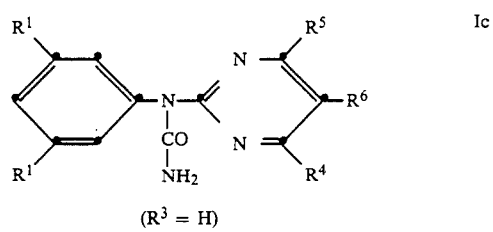

($R^3 = H$)

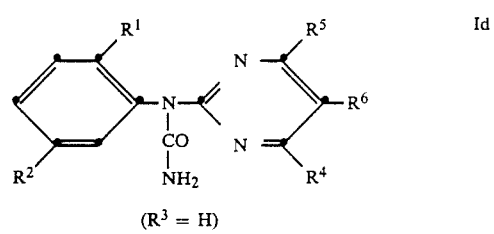

($R^3 = H$)

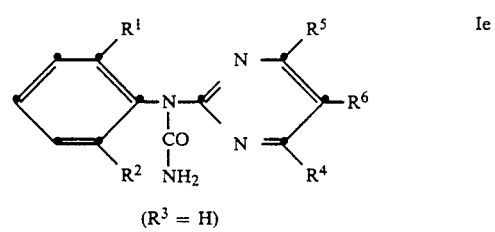

($R^3 = H$)

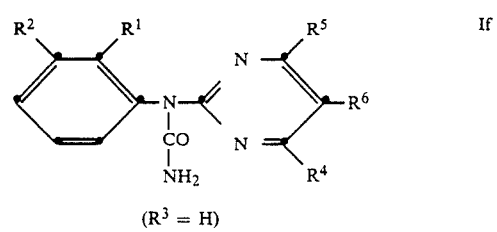

($R^3 = H$)

and

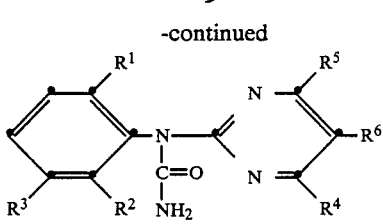

The substituents $R^1$ to $R^6$ in compounds of formulae Ia to Ig may have the scopes of definition given hereinbefore with respect to formula I.

Especially preferred is that sub-group of compounds of formula I in which the scopes of definition of the radicals $R^1$ to $R^4$ correspond to those given hereinbefore, and in which $R^5$ and $R^6$ together are a fused ring system according to one of the definitions given hereinbefore.

Attention is drawn most especially to compounds of formula Ie in which $R^1$ is nitro, fluorine or chlorine,
$R^2$ is hydrogen, fluorine, chlorine or methyl,
$R^4$ is trifluoromethyl and
$R^5$ and $R^6$ together are —$(CH_2)_3$— or —$(CH_2)_4$—.

The following compounds of formula I are to be mentioned specifically:

2-[N-carbamoyl-N-(2-methyl-6-nitrophenyl)-amino]-5,6,7,8-tetrahydro-4-trifluoromethyl-quinazoline,
2-([N-carbamoyl-N-(2-nitrophenyl)-amino]-4-trifluoromethyl-5H-6,7- dihydro-cyclopenta[d]pyrimidine,
2-[N-carbamoyl-N-(2-nitrophenyl)-amino]-4-chloro-5-(2-chloroethyl)-6-methyl-pyrimidine,
2-[N-carbamoyl-N-(2-nitrophenyl)-amino]-4-chloro-5-methyl-6-trifluoromethyl-pyrimidine,
2-[N-carbamoyl-N-(6-methyl-2-nitrophenyl)-amino]-4-ethyl-5-methyl-6-trifluoromethyl-pyrimidine,
2-[N-carbamoyl-N-(2-nitrophenyl)-amino]-4-trifluoromethyl-5-methyl-5,6,7,8-tetrahydro-quinazoline,
2-[N-carbamoyl-N-(2-nitrophenyl)-amino]-4-chloro-5,6,7,8-tetrahydroquinazoline,
2-[N-carbamoyl-N-(2-nitrophenyl)-amino]-4-trifluoromethyl-5,6,7,8-tetrahydro-quinazoline,
2-[N-carbamoyl-N-(2-nitrophenyl)-amino]-4-trifluoromethyl-9H-5,6,7,8-tetrahydro-cyclopenta[d]pyrimidine,
2-[N-carbamoyl-N-(2-nitrophenyl)-amino]-4-trifluoromethyl-5,6,7,8,9,10-hexahydro-cyclopenta[d]pyrimidine,
2-[N-carbamoyl-N-(6-methyl-2-nitrophenyl)-amino]-4-trifluoromethyl-5H-7-dihydro-cyclopenta[d]pyrimidine,
2-[N-carbamoyl-N-(6-methyl-2-nitrophenyl)-amino]-4-trifluoromethyl-5,6,7,8-tetrahydro-quinazoline,
2-[N-carbamoyl-N-(6-methyl-2-nitrophenyl)-amino]-4-trifluoromethyl-9H-5,6,7,8-tetrahydro-cyclopenta[d]pyrimidine,
2-[N-carbamoyl-N-(2,5-dichlorophenyl)-amino]-4-trifluoromethyl-5H-6,7-dihydro-cyclopenta[d]pyrimidine,
2-[N-carbamoyl-N-(2,5-dichlorophenyl)-amino]-4-chloro-5,6,7,8-tetrahydroquinazoline,
2-[N-carbamoyl-N-(2,5-dichlorophenyl)-amino]-4-trifluoromethyl-5,6,7,8-tetrahydro-quinazoline,
2-[N-carbamoyl-N-(2,5-dichlorophenyl)-amino]-4-trifluoromethyl-9H-5,6,7,8-tetrahydro-cyclohepta[d]pyrimidine,
2-[N-carbamoyl-N-(2,5-dichlorophenyl)-amino]-4-trifluoromethyl-5,6,7,8,9,10-hexahydro-cycloocta[d]pyrimidine,
2-[N-carbamoyl-N-(6-chloro-2-fluorophenyl)-amino]-4-trifluoromethyl-5,6,7,8-tetrahydro-quinazoline,
2-[N-carbamoyl-N-(6-chloro-2-fluorophenyl)-amino]-4-trifluoromethyl-5H-6,7-dihydro-cyclopenta[d]pyrimidine,
2-[N-carbamoyl-N-(2,5-dichlorophenyl)-amino]-4-trifluoromethyl-5H-6,7-dihydro-cyclopenta[d]pyrimidine,
2-[N-carbamoyl-N-(2-nitro-6-methylphenyl)-amino]-4-trifluoromethyl-5H-6,7-dihydro-cyclopenta[d]pyrimidine,
2-[N-carbamoyl-N-2-(nitrophenyl)-amino]-4-isopropyl-6-trifluoromethyl-5-methylpyrimidine,
2-[N-carbamoyl-N-(2,6-dichlorophenyl)-amino]-4-trifluoromethyl-5-methyl-6-chloropyrimidine,
2-[N-carbamoyl-N-(2,6-dichlorophenyl)-amino]-4-isopropyl-5-methyl-6-trifluoromethylpyrimidine,
2-[N-carbamoyl-N-(2-nitro-6-methylphenyl)-amino]-4,5-dimethyl-6-trifluoromethylpyrimidine,
2-[N-carbamoyl-N-(2,6-difluorophenyl)-amino]-4-ethyl-5-methyl-6-trifluoromethylpyrimidine,
2-[N-carbamoyl-N-(2-nitrophenyl)-amino]-4-difluoromethyl-5,6,7,8-tetrahydroquinazoline,
2-[N-carbamoyl-N-(2-nitrophenyl)-amino]-4-trifluoromethyl-7-methyl-5,6,7,8-tetrahydro-quinazoline,
2-[N-carbamoyl-N-(2-nitrophenyl)-amino]-4-trifluoromethyl-6-methyl-5,6,7,8-tetrahydro-quinazoline,
2-[N-carbamoyl-N-(2-nitro-6-methylphenyl)-amino]-4-chlorodifluoromethyl-5H-6,7-dihydro-cyclopenta[d]pyrimidine,
2-[N-carbamoyl-N-(2-nitro-6-methylphenyl)-amino]-4-chlorodifluoromethyl-5,6,7,8-tetrahydro-quinazoline,
2-[N-carbamoyl-N-(2-nitro-6-methylphenyl)-amino]-4-difluoromethyl-6,7,8-tetrahydro-quinazoline,
2-[N-carbamoyl-N-(2-nitro-6-methylphenyl)-amino]-4-tetrafluoromethyl-7-methyl-5,6,7,8-tetrahydro-quinazoline,
2-[N-carbamoyl-N-(2,6-dichlorophenyl)-amino]-4-trifluoromethyl-5,6-dihydro-cyclobuta[d]pyrimidine,
2-[N-carbamoyl-N-(2,6-dichlorophenyl)-amino]-4-difluoromethyl-5H-6,7-dihydro-cyclopenta[d]pyrimidine,
2-[N-carbamoyl-N-(2,6-dichlorophenyl)-amino]-4-trifluoromethyl-5,6,7,8-tetrahydro-quinazoline,
2-[N-carbamoyl-N-(2-chloro-6-methylphenyl)-amino]-4-trifluoromethyl-5H-6,7-dihydro-cyclopenta[d]pyrimidine,
2-[N-carbamoyl-N-(2-chloro-6-methylphenyl)-amino]-4-chlorodifluoromethyl-5H-6,7-dihydro-cyclopenta[d]pyrimidine,
2-[N-carbamoyl-N-(2-chloro-6-methylphenyl)-amino]-4-difluoromethyl-5H-6,7-dihydro-cyclopenta[d]pyrimidine,
2-[N-carbamoyl-N-(2-chloro-6-methylphenyl)-amino]-4-trifluoromethyl-6,7,8-tetrahydro-quinazoline,
2-[N-carbamoyl-N-(2-chloro-6-methylphenyl)-amino]-4-chlorodifluoromethyl-5,6,7,8-tetrahydro-quinazoline,
2-[N-carbamoyl-N-(2-chloro-6-methylphenyl)-amino]-4-difluoromethyl-5,6,7,8-tetrahydro-quinazoline, 2-[N-carbamoyl-N-(2-difluoromethoxyphenyl)-amino]-4-trifluoromethyl-5,6,7,8-tetrahydro-quinazoline,
2-[N-carbamoyl-N-(2-methylsulfinyl-5-chlorophenyl)-amino]-4-trifluoromethyl-5,6,7,8-tetrahydro-quinazoline,
2-[N-carbamoyl-N-(2-methylthio-5-chlorophenyl)-amino]-4-trifluoromethyl-5,6,7,8-tetrahydro-quinazoline,
2-[N-carbamoyl-N-(2-nitro-6-methylphenyl)-amino]-4-trifluoromethyl-5,6,7,8,9,10-hexahydro-cycloocta[d]pyrimidine,
2-[N-carbamoyl-N-(2-nitrophenyl)-amino]-4-chlorodifluoromethyl-5,6,7,8-tetrahydro-quinazoline,
2-[N-carbamoyl-N-(2-nitro-6-methylphenyl)-amino]-4-trifluoromethyl-6-methyl-5,6,7,8-tetrahydro-quinazoline,
2-[N-carbamoyl-N-(2-fluorophenyl)-amino]-4-trifluoromethyl-5,6,7,8-tetrahydro-quinazoline,
2-[N-carbamoyl-N-(2,6-dichloro-3-methylphenyl)-amino]-4-trifluoromethyl-5,6,7,8-tetrahydro-quinazoline,
2-[N-carbamoyl-N-(2,6-dichloro-3-methylphenyl)-amino]-4-trifluoromethyl-5H-6,7-dihydro-cyclopenta[d]pyrimidine,
2-[N-carbamoyl-N-(2-nitro-6-fluorophenyl)-amino]-4-trifluoromethyl-5,6,7,8-tetrahydro-quinazoline,
2-[N-carbamoyl-N-(2-nitro-6-fluorophenyl)-amino]-4-trifluoromethyl-5H-6,7-dihydro-cyclopenta[d]pyrimidine,
2-[N-carbamoyl-N-(2-methoxy-6-chlorophenyl)-amino]-4-trifluoromethyl-5,6,7,8-tetrahydro-quinazoline,
2-[N-carbamoyl-N-(2-methoxy-6-chlorophenyl)-amino]-4-trifluoromethyl-5H-6,7-dihydro-cyclopenta[d]pyrimidine,
2-[N-carbamoyl-N-(2,6-difluorophenyl)-amino]-4-trifluoromethylthio-5,6,7,8-tetrahydro-quinazoline,
2-[N-carbamoyl-N-(2,6-difluorophenyl)-amino]-4-chlorodifluoromethyl-5,6,7,8-tetrahydro-quinazoline,
2-[N-carbamoyl-N-(2,6-difluorophenyl)-amino]-4-difluoromethyl-5,6,7,8-tetrahydro-quinazoline,
2-[N-carbamoyl-N-(2-methyl-5-fluorophenyl)amino]-4-trifluoromethyl-5,6,7,8-tetrahydro-quinazoline,
2-[N-carbamoyl-N-(2,6-dibromophenyl)-amino]-4-trifluoromethyl-5,6,7,8-tetrahydro-quinazoline,
2-[N-carbamoyl-N-(2,6-dimethylphenyl)-amino]-4-difluoromethyl-5,6,7,8-tetrahydro-quinazoline,
2-[N-carbamoyl-N-(2-nitrophenyl)-amino]-4-chlorodifluoromethyl-5H-6,7-dihydro-cyclopenta[d]pyrimidine,
2-[N-carbamoyl-N-(2-nitrophenyl)-amino]-4-difluoromethyl-5H-6,7-dihydrocyclopenta[d]pyrimidine,
2-[N-carbamoyl-N-(2,5-dichlorophenyl)-amino]-4-difluoromethyl-5H-6,7-dihydro-cyclopenta[d]pyrimidine,
2-[N-carbamoyl-N-(2-fluoro-6-chlorophenyl)-amino]-4-difluoromethyl-5H-6,7-dihydro-cyclopenta[d]pyrimidine,
2-[N-carbamoyl-N-(2-difluoromethylthiophenyl)-amino]-4-trifluoromethyl-5H-6,7-dihydro-cyclopenta[d]pyrimidine,
2-[N-carbamoyl-N-(2-difluoromethoxy-6-methylphenyl)-amino]-4-trifluoromethyl-5,6,7,8-tetrahydro-quinazoline,
2-[N-carbamoyl-N-(2,6-difluorophenyl)-amino]-4-difluoromethyl-5H-6,7-dihydro-cyclopenta[d]pyrimidine,
2-[N-carbamoyl-N-(2-nitrophenyl)-amino]-4-chloro-5-methyl-6-thiomethylpyrimidine,
2-[N-carbamoyl-N-(2-methyl-6-chlorophenyl)-amino]-4-chloro-5-methyl-6-trifuloromethylpyrimidine,
2-[N-carbamoyl-N-(2-nitrophenyl)-amino]-4-trifluoromethyl-5-methyl-6ethoxypyrimidine and
2-[N-carbamoyl-N-(2-nitrophenyl)-amino]-4-trifluoromethyl-5-methoxy-6chloropyrimidine.

The compounds of formula I can be prepared by (a) reacting an aniline of formula II with phosgene to form a carbamoyl chloride of formula III and reacting this with NH₃ in a second step

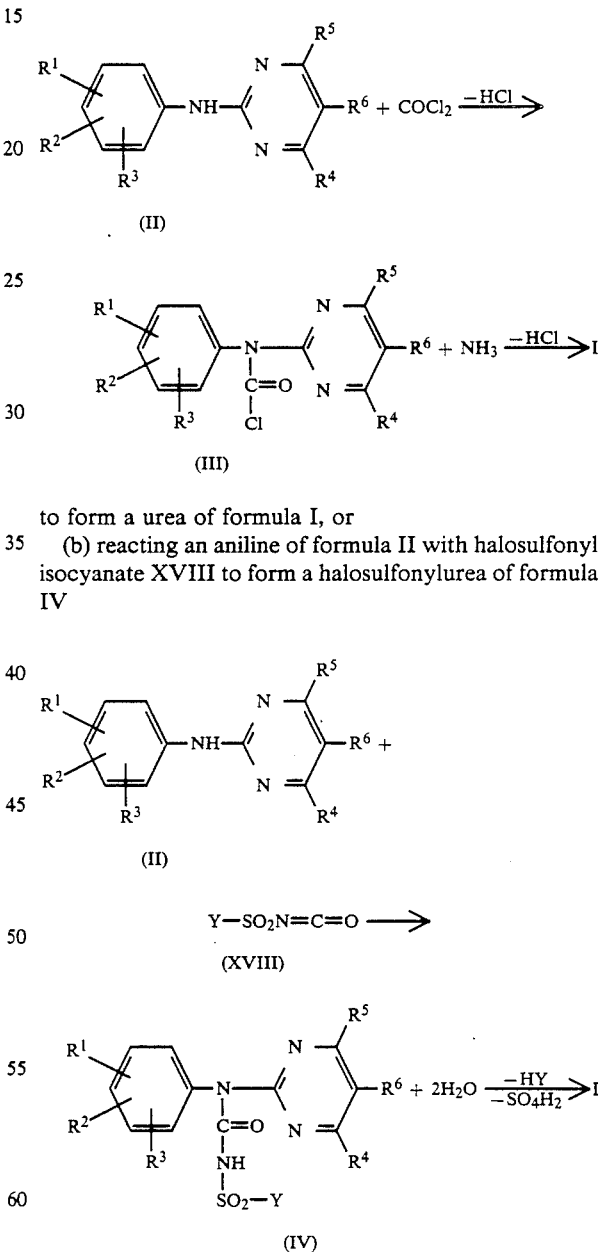

to form a urea of formula I, or (b) reacting an aniline of formula II with halosulfonyl isocyanate XVIII to form a halosulfonylurea of formula IV and hydrolysing this in a second step, or directly, to a compound of formula I, Y being a group that can be removed under the reaction conditions, such as halogen, preferably chlorine.

Furthermore, ureas of formula I'

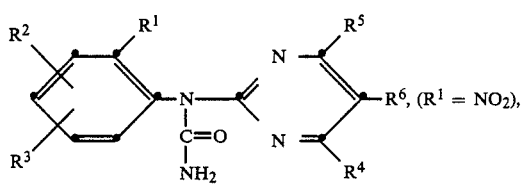 (I')

in which $R^1$ is bonded in the ortho-position of the phenyl ring and represents nitro, can be prepared by (c) rearranging a sulfonylurea of formula V, under the action of an aqueous base, to form a urea of formula I'

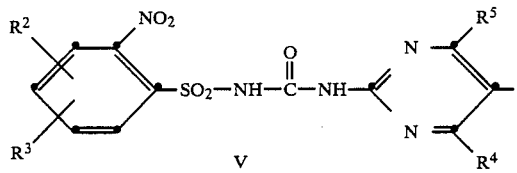

NaOH/water or KOH/water preferably being used as aqueous bases.

The reactions II→III, III→I, V→I' and IV→I, which proceed with the removal of hydrogen halide or the elimination of HY, are preferably carried out using acid-binding agents (bases).

Suitable acid-binding agents are organic or inorganic bases, for example tertiary amines, such as trialkylamines (trimethylamine, triethylamine, tripropylamine etc.), pyridines (pyridine, 4-dimethylaminopyridine, 4-pyrrolidylaminopyridine etc.), and alcoholates, such as, for example, potassium tert.-butoxide, sodium methoxide or sodium ethoxide. The aforementioned reactions, including also the reaction V→I', can also be carried out with bases under phase transfer conditions according to processes that are known per se. (Lit. Dehmlow & Dehmlow, Phase Transfer Catalysis Verlag Chemie, Weinheim, 1983).

It is possible, in principle, for one or more solvents or diluents that are inert towards the reaction to be present in process variants (a), (b) and (c), should there be no specific details given. Suitable solvents or diluents are, for example, aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butylmethyl ether etc.), anisole, dioxan, tetrahydrofuran; nitriles, such as acetonitrile, propionitrile; N,N-dialkylated amides, such as dimethylformamide; dimethyl sulfoxide; ketones, such as acetone, diethyl ketone, methyl ethyl ketone; and mixtures of such solvents with each other.

The anilines of formula II, like the carbamoyl chlorides of formula III and the novel ureas of formula Iv, are valuable intermediates.

Some anilines of formula II are already known (Tagungsber. Akad. Landwirtschaftswiss. German Democratic Republic 1984, 222Chem. Abstr. 102 162 065b; Biomed Mass. Spectrum 11 (1984), 435–40; DD 151 404; Tetrahedron Lett. 1969 2595–8; DE-OS 18 00 708; Z. Chem. 8 (1968) 103–4).

The invention accordingly relates also to the novel anilines of formula II

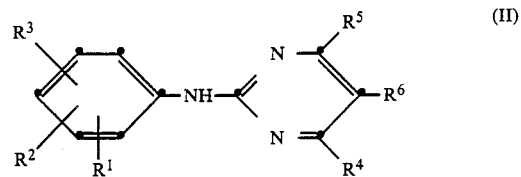

in which the radicals $R^1$ to $R^6$ are as defined hereinbefore.

Especially preferred are the anilines II in which $R^5$

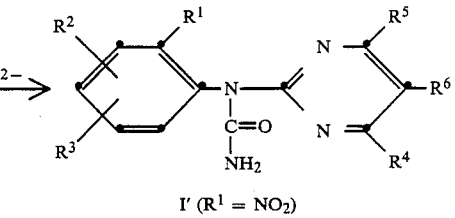

I' ($R^1 = NO_2$)

and $R^6$ together are a fused bridge.

Another object of this invention are to the novel carbamoyl chlorides of formula III

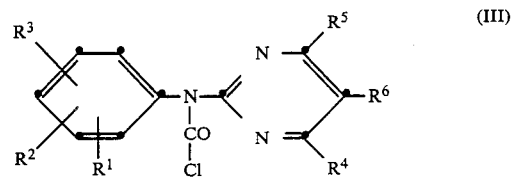

in which the radicals $R^1$ to $R^6$ are as defined hereinbefore, and the novel ureas of formula IV

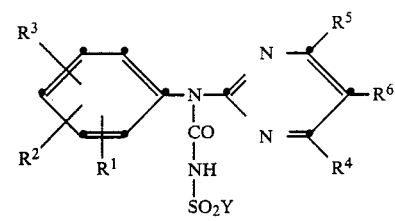

in which the radicals $R^1$ to $R^6$ are as defined hereinbefore and Y is halogen.

The novel anilines of formula II can be prepared analogously to processes known from the literature by (d) reacting a guanidine of formula VI, in which the radicals $R^1$ to $R^3$ are as defined hereinbefore, with a 1,3-dicarbonyl compound of formula VII in which the radicals $R^4$ to $R^6$ are as defined hereinbefore

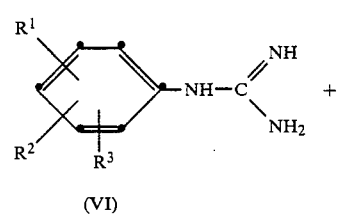

(VI)

-continued

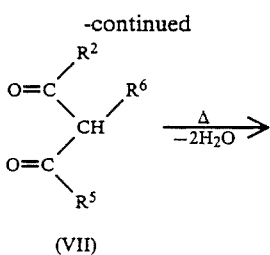

(VII)

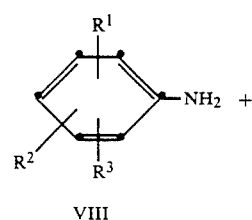

(II)

the condensation reaction if desired being carried out in the presence of a water-binding agent (Lit.: D. J. Brown in "The Chemistry of Heterocyclic Compounds" Vol. VI 1962, Interscience Publ. New York; J. Am. Chem. Soc. 69 1819 (1947); J. Am. Chem. Soc. 72 2948 (1950); J. Org. Chem. 29 1439 (1964) or J. Org. Chem. 29 1883 (1964), Houben-Weyl "Methoden d. org. Chemie" Vol. VIII p. 180 ff), or (e) reacting an aniline of formula VIII with a pyrimidine of formula IX under the action of a base,

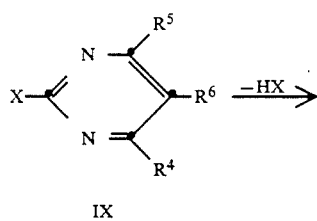

VIII

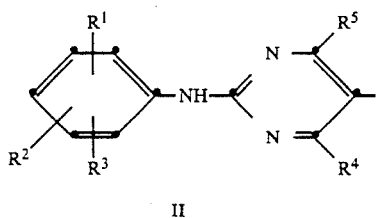

IX

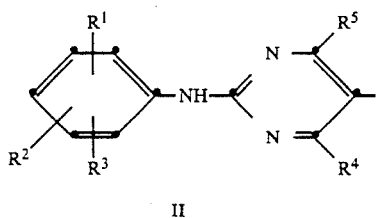

II in which formulae the radicals $R^1$ to $R^6$ are as defined hereinbefore and X is a nucleofugal group, such as halogen, or $C_1$-$C_4$alkylsulfonyl.

Suitable bases for carrying out this process are, inter alia, potassium tert.-butoxide, $Na_2CO_3$, $K_2CO_3$ or NaH.

These processes are generally available for the synthesis of compounds of formula II and are applicable to all educts of formulae V, VI, VII and VIII (in which the radicals $R^1$ to $R^6$ are as defined within the scope of the formula of compounds I).

The sulfonylureas V are obtainable analogously to processes known from the literature by (f) reacting a sulfonamide X, in which $R^2$ and $R^3$ are as defined hereinbefore, with phosgene to form an isocyanate XI, and then allowing this to react with a 2-aminopyrimidine XII to form V:

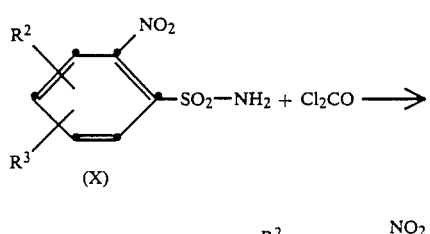

(X)

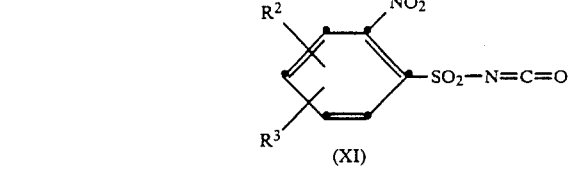

(XI)

$$XI + H_2N-\underset{(XII)}{\diagdown}$$

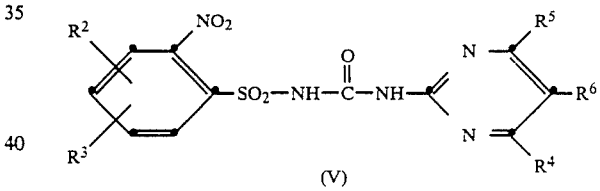

(V)

or (g) reacting a 2-aminopyrimidine XII, in which $R^4$ to $R^5$ are as defined hereinbefore, with phosgene to form an isocyanate XIII, and then allowing this to react with a sulfonamide X, in which $R^2$ and $R^3$ are as defined hereinbefore, to form V:

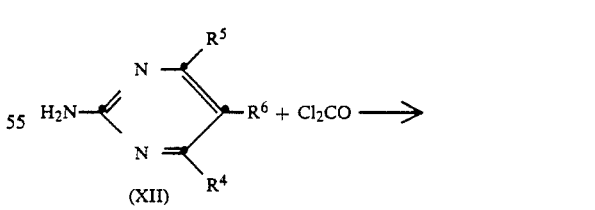

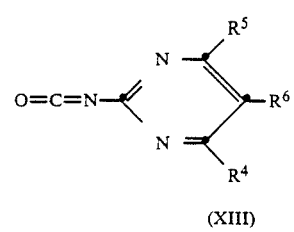

(XIII)

-continued

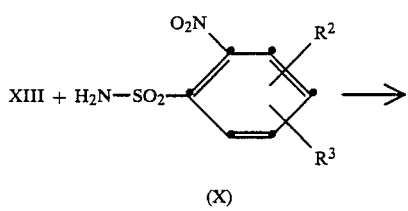

(X)

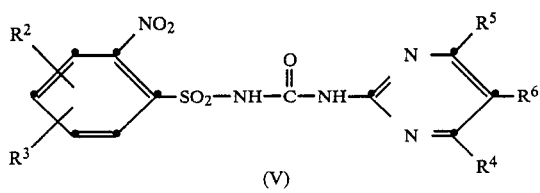

(V)

The guanidines VI can be prepared analogously to processes known from the literature by (h) reacting an aniline VIII, in which $R^1$ to $R^3$ are as defined hereinbefore, with cyanamide:

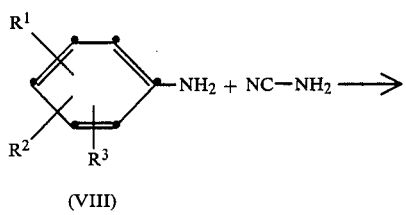

(VIII)

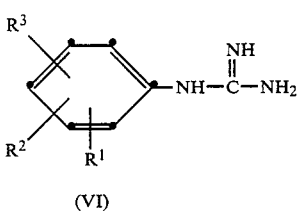

(VI)

or (i) reacting a thiourea ($R^7=H$) or an isothiourea ($R^7=C_1$-$C_4$alkyl) of formula XIV, in which the radicals $R^1$ to $R^3$ are hereinbefore and $R^7$ is hydrogen or $C_1$-$C_4$alkyl, with ammonia to form the guanidine VI:

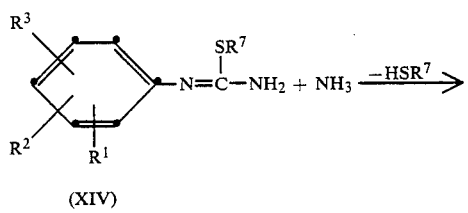

(XIV)

-continued

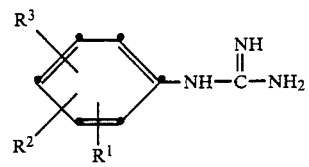

(VI)

(Literature: process h): Houben-Weyl, Methoden de . Chemie, Thieme, Struttgart, Vol. VIII p. 98, 180; process i): Houb-Weyl, Methoden der Org. Chemie, Thieme, Stuttgart, Vol. VIII p. 183).

The β-diketones VII can also be prepared an to processes known from the literature by (j) reacting, under the reaction conditions of a condensation, a ketone XV, in which $R^5$ and $R^6$ are as defined hereinbefore, with a compound of formula XVI, in which $R^4$ is as defined hereinbefore and Z is a group that can be removed under the reaction of a Claisen condensation, such as $C_1$-$C_4$alkoxy, phenoxy, benz halogen.

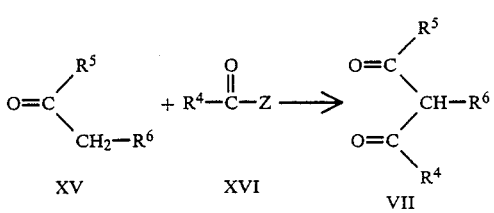

XV    XVI    VII (Lit.: C. Ferry Reaktionen der organischen Synthese, Thieme Stuttgart, 1978 p. 312 and the literature cited therein).

The 2-aminopyrimidines XII, the 2-isocyanopyrimidines XIII, the 2-halopyrimidines IX' (in which X=halogen), the 2-mercaptopyrimidines IX" (in which X=SH), the 2-alkylthiopyrimidines IX''' (in which X=$C_1$-$C_4$alkylthio) and the 2-alkylsulfonylpyrimidines IX'''' (in which X=$C_1$-$C_4$alkyl-$SO_2$-), in which compounds the radicals $R^4$ to $R^5$ are as defined hereinbefore, are in most cases novel.

It is especially the compounds of formulae XI, XIII and IX in which the radicals $R^5$ and $R^6$ together are a fused carbocyclic or heterocyclic radical that are novel.

There are numerous methods of synthesis available to the skilled person for the preparation of the compounds of formulae XIII, IX', IX" and IX''''. These are generally known to the chemist and are described comprehensively in the relevant textbooks.

The following synthesis scheme (scheme I) shows an extract of the possible methods of preparing these compounds, the β-diketone VII being used as starting material in each case:

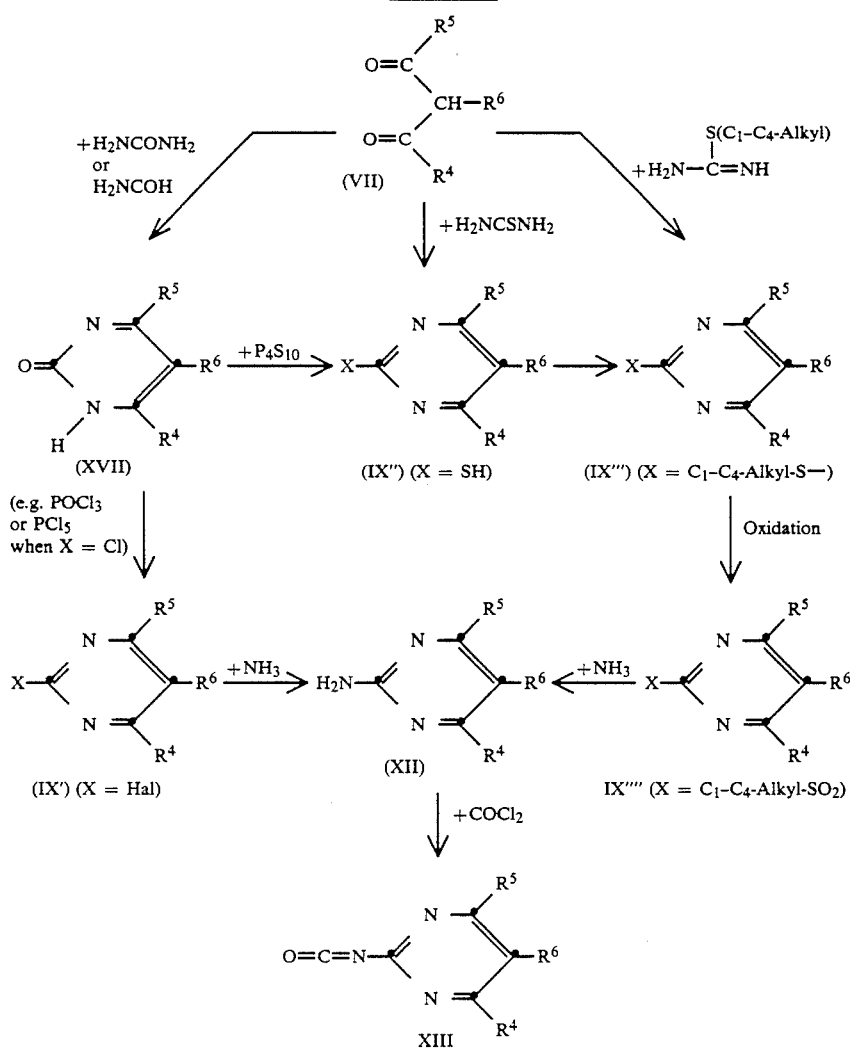

Scheme I

The pyridinones XVII, in which the radicals $R^4$ to $R^6$ are as defined hereinbefore, are also in some cases novel.

In particular, those pyrimidinones of formula XVII in which the radicals $R^5$ and $R^6$ together are fused carbocyclic or heterocyclic radical are novel.

The invention furthermore relates to herbicidal and plant growth-regulating compositions containing a compound of formula I together with suitable adjuvants and/or carriers.

The active ingredients of the formula I are in general used successfully at application rates of from 0.005 to 5 kg/ha, especially from 0.1 to 3 kg/ha. The dosage necessary to achieve the desired effect can be ascertained by tests. It is dependent upon the nature of the action, the stage of development of the crop plants and of the weed and on the application (locus, time, method), and may vary within wide ranges, subject to these parameters.

At lower rates of application the compounds of formula I are distinguished by growth-inhibiting and selective herbicidal properties which make them excellent for use in crops of useful plants, especially cereals, cotton, soybeans, rape, maize and rice.

The compounds of formula I also have plant growth-regulating properties. The growth of both monocotyledons and dicotyledons is affected.

Inhibition of the vegetative growth makes it possible with many crop plants for the crop to be more densely planted, so that it is possible to achieve a higher yield per unit area of soil.

Another mechanism of the increase in yield when using growth regulators is based on the fact that the nutrients are used to the greater advantage of the formation of the flowers and fruit whilst the vegetative growth is restricted.

At higher rates of application, weeds and grasses are damaged in their development to such an extent that they die.

In an especially advantageous manner, the growth-regulating compounds of formula I can be used for regulating the growth of intersown plants in maize crops.

Plants that are suitable in principle for intersowing in crops of maize are those that cover the soil between the individual maize plants and thus especially counteract soil erosion in maize crops. Suitable plants for intersowing are, inter alia, rape, trefoil, grasses or leguminosae.

At suitable rates of application the compounds of formula I inhibit the new growth of grasses. This makes it possible to reduce the number of cuts necessary or to increase the intervals between cutting in grassed areas (parks, gardens, etc.). In an especially advantageous manner it is possible to use granulate formulations of the active ingredients of formula I for this purpose. Either the granulate may contain the active ingredient on its own together with the customary adjuvants and carriers, or the active ingredient is formulated as a granulate together with a mineral fertiliser and/or, if desired, other active ingredients for controlling moss or other plant growth that is undesirable in grassed areas. Application in the form of a scatter granulate for direct soil application makes it possible, using equipment customary for maintaining grassed areas, to inhibit the new growth of grasses for a relatively long period. The granulate can be prepared in a manner known per se, and it preferably has a granule size of 0.1 to 2.0 mm, especially 0.25 to 1.0 mm.

The invention relates also to herbicidal and plant growth-regulating compositions that contain an active ingredient of formula I, and to methods of controlling weeds pre-emergence and post-emergence and of influencing the growth of monocotyledonous and dicotyledonous plants, especially grasses, tropical cover crops and suckers.

The compounds of formula I are used in unmodified form or, preferably, in the form of compositions together with the adjuvants conventionally employed in the art of formulation, and are therefore advantageously formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The active substances of formula I can thus also be applied to mineral fertilisers (as a dressing). The composition so obtainable is advantageously suitable as a growth regulator for grasses.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties.

The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

Agglutinants are especially those adjuvants that in the case of granulation cause the carrier material, the adjuvants and the active ingredients to stick together, such as gum arabic or carboxymethylcellulose.

Surfactants customary in the art of formulation are described, inter alia, in the following publications:

"1987 International Mc Cutcheon's Emulsifiers and Detergents", Glen Rock, N.J., USA.

Dr. Helmut Stache "Tensid Taschenbuch"
Carl Hanser Varlag, Munich/Vienna 1981.

The preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed especially as follows (%=percent by weight)

| Emulsifiable concentrates | |
|---|---|
| a compound of formula I | 1 to 20%, preferably 5 to 10% |
| surfactant | 5 to 30%, preferably 10 to 20% |
| liquid carrier | 50 to 94%, preferably 70 to 85%. |
| Dusts | |
| a compound of formula I | 0.1 to 10%, preferably 0.1 to 1% |
| solid carrier | 99.9 to 90%, preferably 99.9 to 99%. |
| Suspension concentrates | |
| a compound of formula I | 5 to 75%, preferably 10 to 50% |
| water | 94 to 25%, preferably 90 to 30% |
| surfactant | 1 to 40%, preferably 2 to 30%. |
| Wettable powders | |
| a compound of formula I | 0.5 to 90%, preferably 1 to 80% |
| surfactant | 0.5 to 20%, preferably 1 to 15% |
| solid carrier | 5 to 95%, preferably 15 to 90%. |
| Granulates | |
| a compound of formula I | 0.5 to 30%, preferably 3 to 15% |
| solid carrier | 99.5 to 70%, preferably 97 to 85%. |

| Scatter granulate | |
|---|---|
| a compound of formula I | 0.01 to 30%, preferably 0.05 to 15% |
| agglutinant | 0.05 to 5%, preferably 0.1 to 2% |
| surfactant | 0.5 to 20%, preferably 1 to 15% |
| solid carrier | 99.44 to 45%, preferably 95 to 65% |

Whereas commercial products will preferably be formulated as concentrates, the end user will normally employ dilute formulations. The formulations can be diluted to a concentration as low as 0.001% active ingredient. The rates of application are normally from 0.005 to 5 kg active ingredient/ha.

The compositions may also contain further additives such as stabilisers, antifoams, viscosity regulators, binders, tackifiers and also fertilisers or other active ingredients for obtaining special effects.

Preparation Examples:

The (uncorrected) melting points in the following Preparation Examples are in °C.

P. 1. Compounds of formula I

P. 1.1.

2-[N-carbamoyl-N-(2-methyl-6-nitrophenyl)-amino]-5,6,7,8-tetrahydro-4-trifluoromethyl-quinazoline 2.2 ml of chlorosulfonyl isocyanate are added at 3° C. to a solution of 7.0 g of 2-(2-methyl-6-nitrophenylamino)-5,6,7,8-tetrahydro-4-trifluoromethyl-quinazoline in 100 ml of ethyl acetate. The whole is stirred for one hour while cooling on an ice-bath, and subsequently 50 ml of ethyl acetate and 30 ml of water are added. The organic phase is separated off, washed with brine, dried and concentrated in vacuo. The residue is triturated with hexane, the product crystallising out. 7.8 g of the title compound of formula are isolated in the form of crystals having a melting point of 161°–162° C. (decomp.) (comp. No. 1.563).

The compounds of Table 1 can be prepared in an analogous manner:

TABLE 1

Compounds of formula: (I)

| Comp. No | $R^1$ | $R^2$ | $R^3$ | $R^4$ | $R^5$ | $R^6$ | Phys. data |
|---|---|---|---|---|---|---|---|
| 1.001 | 2-Cl | H | H | $CH_3$ | Cl | $CH_3$ | |
| 1.002 | 2-Cl | H | H | $CH_3$ | $CF_3$ | $CH_3$ | |
| 1.003 | 2-Cl | H | H | $C_2H_5$ | $CF_3$ | $CH_3$ | |
| 1.004 | 2-Cl | H | H | $OCH_3$ | $CF_3$ | $CH_3$ | |
| 1.005 | 2-Cl | H | H | $CH_3$ | $CF_3$ | $C_2H_5$ | |
| 1.006 | 2-F | H | H | $CH_3$ | $CF_3$ | $CH_3$ | |
| 1.007 | 2-F | H | H | $CH_3$ | Cl | $CH_3$ | |

TABLE 1-continued

Compounds of formula:

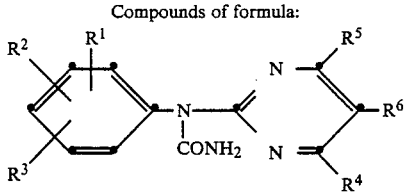

(I)

| | | | | | | | |
|---|---|---|---|---|---|---|---|
| 1.008 | 2-F | H | H | C₂H₅ | CF₃ | CH₃ | |
| 1.009 | 2-F | H | H | SCH₃ | CF₃ | CH₃ | |
| 1.010 | 2-F | H | H | OCH₃ | CH₃ | CN | |
| 1.011 | 2-Br | H | H | CH₃ | Cl | CH₃ | |
| 1.012 | 2-Br | H | H | CH₃ | CF₃ | CH₃ | |
| 1.013 | 2-Br | H | H | C₂H₅ | CF₃ | CH₃ | |
| 1.014 | 2-Br | H | H | C₂H₅ | CF₂Cl | CH₃ | |
| 1.015 | 2-Br | H | H | C₂H₅ | CHFCl | CH₃ | |
| 1.016 | 2-Br | H | H | C₂H₅ | C₂F₅ | CH₃ | |
| 1.017 | 2-Br | H | H | C₂H₅ | CHCl₂ | CH₃ | |
| 1.018 | 2-Br | H | H | CH₃ | CF₂CF₃ | CH₃ | |
| 1.019 | 2-Br | H | H | OCH₃ | CF₃ | CH₃ | |
| 1.020 | 2-Br | H | H | SCH₃ | CF₃ | CH₃ | |
| 1.021 | 2-Br | H | H | SCH₃ | CH₃ | CH₃ | |
| 1.022 | 2-Br | H | H | SO₂CH₃ | CH₃ | CH₃ | |
| 1.023 | 2-Br | H | H | Cyclopropyl | CF₃ | CH₃ | |
| 1.024 | 2-Br | H | H | C₃H₇(i) | CF₃ | CH₃ | |
| 1.025 | 2-Br | H | H | CH₃ | Cl | CH₂CH₂Cl | |
| 1.026 | 2-Br | H | H | CH₃ | Cl | CH₂CH₂OCH₃ | |
| 1.027 | 2-Br | H | H | OCH₃ | CH₃ | CH₂CH₂OCH₃ | |
| 1.028 | 2-J | H | H | CH₃ | Cl | CH₃ | |
| 1.029 | 2-J | H | H | CH₃ | CF₃ | CH₃ | |
| 1.030 | 2-J | H | H | C₂H₅ | CF₃ | CH₃ | |
| 1.031 | 2-J | H | H | OCH₃ | CH₃ | CH₃ | |
| 1.032 | 2-J | H | H | CH₃ | Cl | C₂H₅ | |
| 1.033 | 2-J | H | H | Cyclopropyl | CF₃ | CH₃ | |
| 1.034 | 2-CF₃ | H | H | CH₃ | Cl | CH₃ | |
| 1.035 | 2-CF₃ | H | H | OCH₃ | CH₃ | CH₃ | |
| 1.036 | 2-CF₃ | H | H | SCH₃ | CH₃ | CH₃ | |
| 1.037 | 2-CF₃ | H | H | SO₂CH₃ | CH₃ | CH₃ | |
| 1.038 | 2-CF₃ | H | H | CH₃ | CF₃ | CH₃ | |
| 1.039 | 2-CF₃ | H | H | C₂H₅ | CF₃ | CH₃ | |
| 1.040 | 2-CF₃ | H | H | C₂H₅ | CF₂Cl | CH₃ | |
| 1.041 | 2-CF₃ | H | H | C₂H₅ | CHCl₂ | CH₃ | |
| 1.042 | 2-CF₃ | H | H | C₂H₅ | CF₂CF₃ | CH₃ | |
| 1.043 | 2-CF₃ | H | H | OCH₃ | CH₃ | CN | |
| 1.044 | 2-CF₃ | H | H | OCH₃ | CH₃ | NO₂ | |
| 1.045 | 2-CF₃ | H | H | OCH₃ | CH₃ | Cl | |
| 1.046 | 2-NO₂ | H | H | CH₃ | Cl | CH₃ | |
| 1.047 | 2-NO₂ | H | H | CH₃ | CF₃ | CH₃ | |
| 1.048 | 2-NO₂ | H | H | OCH₃ | CF₃ | CH₃ | |
| 1.049 | 2-NO₂ | H | H | SCH₃ | CH₃ | CH₃ | |
| 1.050 | 2-NO₂ | H | H | SOCH₃ | CH₃ | CH₃ | |
| 1.051 | 2-NO₂ | H | H | SO₂CH₃ | CH₃ | CH₃ | |
| 1.052 | 2-NO₂ | H | H | SCH₃ | CF₃ | CH₃ | |
| 1.053 | 2-NO₂ | H | H | CH₃ | CF₃ | Phenyl | |
| 1.054 | 2-NO₂ | H | H | OCH₃ | CF₃ | 4-Cl-Phenyl | |
| 1.055 | 2-NO₂ | H | H | Cl | CF₃ | 4-Cl-Phenyl | |
| 1.056 | 2-NO₂ | H | H | CH₃ | Cl | CH₂CH₂Cl | m.p. 145–146° C. |
| 1.057 | 2-NO₂ | H | H | OCH₃ | CH₃ | CH₂CH₂OCH₃ | |
| 1.058 | 2-NO₂ | H | H | C₂H₅ | CF₃ | CH₃ | m.p. 160–161° C. |
| 1.059 | 2-NO₂ | H | H | C₂H₅ | CF₂Cl | CH₃ | |
| 1.060 | 2-NO₂ | H | H | C₂H₅ | CHCl₂ | CH₃ | |
| 1.061 | 2-NO₂ | H | H | C₂H₅ | CHFCl | CH₃ | |
| 1.062 | 2-NO₂ | H | H | C₂H₅ | C₂H₅ | CH₃ | |
| 1.063 | 2-NO₂ | H | H | C₂H₅ | C₃F₇(n) | CH₃ | |
| 1.064 | 2-NO₂ | H | H | C₂H₅ | CCl₂CF₃ | CH₃ | |
| 1.065 | 2-NO₂ | H | H | C₃H₇(n) | CF₃ | CH₃ | |
| 1.066 | 2-NO₂ | H | H | C₃H₇(n) | CF₃ | C₂H₅ | |
| 1.067 | 2-NO₂ | H | H | C₃H₇(i) | CF₃ | CH₃ | m.p. 162–163° C. |
| 1.068 | 2-NO₂ | H | H | Cyclopropyl | CF₃ | CH₃ | |
| 1.069 | 2-NO₂ | H | H | CH₃ | OCHF₂ | CH₃ | |
| 1.070 | 2-NO₂ | H | H | OCH₃ | CH₃ | NO₂ | |
| 1.071 | 2-NO₂ | H | H | OCH₃ | CH₃ | Cl | |
| 1.072 | 2-NO₂ | H | H | OCH₃ | CH₃ | CN | |
| 1.073 | 2-NO₂ | H | H | CH₃ | Cl | CN | |
| 1.074 | 2-NO₂ | H | H | CH₃ | Cl | NO₂ | |
| 1.075 | 2-NO₂ | H | H | CH₃ | Cl | Cl | |
| 1.076 | 2-NO₂ | H | H | SCH₃ | CH₃ | Cl | |
| 1.077 | 2-NO₂ | H | H | SO₂CH₃ | CH₃ | Cl | |
| 1.078 | 2-NO₂ | H | H | OCH₃ | CH₃ | COOCH₃ | |
| 1.079 | 2-NO₂ | H | H | CH₃ | CH₃ | COOCH₃ | |
| 1.080 | 2-NO₂ | H | H | CH₃ | CF₂Cl | CH₃ | |

TABLE 1-continued

Compounds of formula:

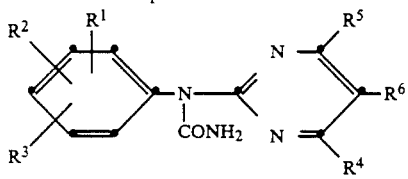

(I)

| | | | | | | |
|---|---|---|---|---|---|---|
| 1.081 | 2-OCH$_3$ | H | H | CH$_3$ | Cl | CH$_3$ |
| 1.082 | 2-OCH$_3$ | H | H | CH$_3$ | CF$_3$ | CH$_3$ |
| 1.083 | 2-OCH$_3$ | H | H | C$_2$H$_5$ | CF$_3$ | CH$_3$ |
| 1.084 | 2-OCH$_3$ | H | H | OCH$_3$ | CH$_3$ | CH$_3$ |
| 1.085 | 2-OCH$_3$ | H | H | OCH$_3$ | CF$_3$ | CH$_3$ |
| 1.086 | 2-OCF$_3$ | H | H | CH$_3$ | Cl | CH$_3$ |
| 1.087 | 2-OCF$_3$ | H | H | CH$_3$ | CF$_3$ | CH$_3$ |
| 1.088 | 2-OCF$_3$ | H | H | OCH$_3$ | CH$_3$ | CH$_3$ |
| 1.089 | 2-OCF$_3$ | H | H | SCH$_3$ | CH$_3$ | CH$_3$ |
| 1.090 | 2-OCF$_3$ | H | H | SO$_2$CH$_3$ | CH$_3$ | CH$_3$ |
| 1.091 | 2-OCF$_3$ | H | H | C$_2$H$_5$ | CF$_3$ | CH$_3$ |
| 1.092 | 2-OCF$_3$ | H | H | C$_2$H$_5$ | CF$_2$Cl | CH$_3$ |
| 1.093 | 2-OCF$_3$ | H | H | SCH$_3$ | CF$_3$ | CH$_3$ |
| 1.094 | 2-OCF$_3$ | H | H | OCH$_3$ | CF$_3$ | CH$_3$ |
| 1.095 | 2-OCF$_3$ | H | H | OC$_2$H$_5$ | CF$_3$ | CH$_3$ |
| 1.096 | 2-OCHF$_2$ | H | H | CH$_3$ | Cl | CH$_3$ |
| 1.097 | 2-OCHF$_2$ | H | H | CH$_3$ | Cl | C$_2$H$_5$ |
| 1.098 | 2-OCHF$_2$ | H | H | OCH$_3$ | CH$_3$ | C$_2$H$_5$ |
| 1.099 | 2-OCHF$_2$ | H | H | SCH$_3$ | CH$_3$ | CH$_3$ |
| 1.100 | 2-OCHF$_2$ | H | H | SO$_2$CH$_3$ | CH$_3$ | CH$_3$ |
| 1.101 | 2-OCHF$_2$ | H | H | CH$_3$ | CF$_3$ | CH$_3$ |
| 1.102 | 2-OCHF$_2$ | H | H | C$_2$H$_5$ | CF$_3$ | CH$_3$ |
| 1.103 | 2-OCHF$_2$ | H | H | C$_2$H$_5$ | CF$_2$Cl | CH$_3$ |
| 1.104 | 2-OCHF$_2$ | H | H | CH$_3$ | Cl | CH$_2$CH$_2$Cl |
| 1.105 | 2-OCHF$_2$ | H | H | OCH$_3$ | CH$_3$ | CH$_2$CH$_2$OCH$_3$ |
| 1.106 | 2-OCHF$_2$ | H | H | OC$_2$H$_5$ | CH$_3$ | CH$_2$CH$_2$OC$_2$H$_5$ |
| 1.107 | 2-OCHF$_2$ | H | H | Cyclopropyl | CF$_3$ | CH$_3$ |
| 1.108 | 2-OCHF$_2$ | H | H | C$_3$H$_7$(i) | CF$_3$ | CH$_3$ |
| 1.109 | 2-OC$_2$H$_5$ | H | H | CH$_3$ | Cl | CH$_3$ |
| 1.110 | 2-OC$_2$H$_5$ | H | H | CH$_3$ | CF$_3$ | CH$_3$ |
| 1.111 | 2-OC$_2$H$_5$ | H | H | OCH$_3$ | CH$_3$ | CH$_3$ |
| 1.112 | 2-OC$_2$H$_5$ | H | H | OCH$_3$ | CF$_3$ | CH$_3$ |
| 1.113 | 2-CN | H | H | CH$_3$ | CF$_3$ | CH$_3$ |
| 1.114 | 2-CN | H | H | C$_2$H$_5$ | CF$_3$ | CH$_3$ |
| 1.115 | 2-CN | H | H | OCH$_3$ | CH$_3$ | CH$_3$ |
| 1.116 | 2-CN | H | H | OCH$_3$ | CF$_3$ | CH$_3$ |
| 1.117 | 2-CN | H | H | SCH$_3$ | CF$_3$ | CH$_3$ |
| 1.118 | 2-CN | H | H | Cyclopropyl | CF$_3$ | CH$_3$ |
| 1.119 | 2-CN | H | H | OCH$_3$ | CH$_3$ | Cl |
| 1.120 | 2-COOCH$_3$ | H | H | CH$_3$ | CF$_3$ | CH$_3$ |
| 1.121 | 2-COOCH$_3$ | H | H | OCH$_3$ | CF$_3$ | CH$_3$ |
| 1.122 | 2-COOCH$_3$ | H | H | C$_2$H$_5$ | CF$_3$ | CH$_3$ |
| 1.123 | 2-COOCH$_3$ | H | H | CH$_3$ | CF$_3$ | Phenyl |
| 1.124 | 2-CON(CH$_3$)$_2$ | H | H | CH$_3$ | Cl | CH$_3$ |
| 1.125 | 2-CON(CH$_3$)$_2$ | H | H | CH$_3$ | CF$_3$ | CH$_3$ |
| 1.126 | 2-CON(CH$_3$)$_2$ | H | H | OCH$_3$ | CF$_3$ | CH$_3$ |
| 1.127 | 2-CON(CH$_3$)$_2$ | H | H | OCH$_3$ | CF$_3$ | C$_2$H$_5$ |
| 1.128 | 2-CH$_3$ | H | H | CH$_3$ | Cl | CH$_3$ |
| 1.129 | 2-CH$_3$ | H | H | CH$_3$ | CF$_3$ | CH$_3$ |
| 1.130 | 2-CH$_3$ | H | H | C$_2$H$_5$ | CF$_3$ | CH$_3$ |
| 1.131 | 2-CH$_3$ | H | H | CH$_3$ | CF$_2$Cl | CH$_3$ |
| 1.132 | 2-CH$_3$ | H | H | OCH$_3$ | CF$_3$ | CH$_3$ |
| 1.133 | 2-C$_2$H$_5$ | H | H | CH$_3$ | Cl | CH$_3$ |
| 1.134 | 2-C$_2$H$_5$ | H | H | CH$_3$ | CF$_3$ | CH$_3$ |
| 1.135 | 2-C$_2$H$_5$ | H | H | OCH$_3$ | CF$_3$ | CH$_3$ |
| 1.136 | 2-C$_2$H$_5$ | H | H | SCH$_3$ | CF$_3$ | CH$_3$ |
| 1.137 | 3-Cl | H | H | CH$_3$ | CF$_3$ | CH$_3$ |
| 1.138 | 3-Br | H | H | CH$_3$ | CF$_3$ | CH$_3$ |
| 1.139 | 3-CF$_3$ | H | H | C$_2$H$_5$ | CF$_3$ | CH$_3$ |
| 1.140 | 3-Cl | 5-Cl | H | CH$_3$ | Cl | CH$_3$ |
| 1.141 | 3-Cl | 5-Cl | H | CH$_3$ | CF$_3$ | CH$_3$ |
| 1.142 | 3-Cl | 5-Cl | H | C$_2$H$_5$ | CF$_3$ | CH$_3$ |
| 1.143 | 3-Cl | 5-Cl | H | OCH$_3$ | CF$_3$ | CH$_3$ |
| 1.144 | 2-Cl | 5-Cl | H | CH$_3$ | Cl | CH$_3$ |
| 1.145 | 2-Cl | 5-Cl | H | CH$_3$ | CF$_3$ | CH$_3$ |
| 1.146 | 2-Cl | 5-Cl | H | OCH$_3$ | CF$_3$ | CH$_3$ |
| 1.147 | 2-Cl | 5-Cl | H | SCH$_3$ | CH$_3$ | CH$_3$ |
| 1.148 | 2-Cl | 5-Cl | H | SOCH$_3$ | CH$_3$ | CH$_3$ |
| 1.149 | 2-Cl | 5-Cl | H | SO$_2$CH$_3$ | CH$_3$ | CH$_3$ |
| 1.150 | 2-Cl | 5-Cl | H | SC$_2$H$_5$ | CF$_3$ | CH$_3$ |
| 1.151 | 2-Cl | 5-Cl | H | SC$_3$H$_7$(i) | CF$_3$ | CH$_3$ |
| 1.152 | 2-Cl | 5-Cl | H | OC$_2$H$_5$ | CF$_3$ | CH$_3$ |
| 1.153 | 2-Cl | 5-Cl | H | SOC$_2$H$_5$ | CF$_3$ | CH$_3$ |

TABLE 1-continued

Compounds of formula: (I)

[Structure: R², R¹ on benzene ring with R³; N-CONH₂ linked to central carbon with N=C-R⁵, N=C-R⁴, and R⁶]

| | R² | R¹ | R³ | R⁴ | R⁵ | R⁶ | |
|---|---|---|---|---|---|---|---|
| 1.154 | 2-Cl | 5-Cl | H | OC₃H₇(i) | CF₃ | CH₃ | |
| 1.155 | 2-Cl | 5-Cl | H | CH₃ | Cl | Phenyl | |
| 1.156 | 2-Cl | 5-Cl | H | OCH₃ | CH₃ | Phenyl | |
| 1.157 | 2-Cl | 5-Cl | H | CH₃ | Cl | CH₂CH₂Cl | |
| 1.158 | 2-Cl | 5-Cl | H | OCH₃ | CH₃ | CH₂CH₂OCH₃ | |
| 1.159 | 2-Cl | 5-Cl | H | C₂H₅ | CF₃ | CH₃ | |
| 1.160 | 2-Cl | 5-Cl | H | CH₃ | CF₂Cl | CH₃ | |
| 1.161 | 2-Cl | 5-Cl | H | CH₃ | C₂H₅ | CH₃ | |
| 1.162 | 2-Cl | 5-Cl | H | CH₃ | C₃F₇(n) | CH₃ | |
| 1.163 | 2-Cl | 5-Cl | H | C₂H₅ | CF₂Cl | CH₃ | |
| 1.164 | 2-Cl | 5-Cl | H | C₂H₅ | CHF₂ | CH₃ | |
| 1.165 | 2-Cl | 5-Cl | H | CH₃ | CCl₂CF₃ | CH₃ | |
| 1.166 | 2-Cl | 5-Cl | H | C₃H₇(n) | CF₃ | CH₃ | |
| 1.167 | 2-Cl | 5-Cl | H | C₃H₇(i) | CF₃ | CH₃ | |
| 1.168 | 2-Cl | 5-Cl | H | Cyclopropyl | CF₃ | CH₃ | |
| 1.169 | 2-Cl | 5-Cl | H | CH₃ | CF₃ | C₂H₅ | |
| 1.170 | 2-Cl | 5-Cl | H | CH₃ | CF₃ | C₃H₇(i) | |
| 1.171 | 2-Cl | 5-Cl | H | CH₃ | OCHF₂ | CH₃ | |
| 1.172 | 2-Cl | 5-Cl | H | OCH₃ | CH₃ | NO₂ | |
| 1.173 | 2-Cl | 5-Cl | H | OCH₃ | CH₃ | Cl | |
| 1.174 | 2-Cl | 5-Cl | H | OCH₃ | CH₃ | CN | |
| 1.175 | 2-Cl | 5-Cl | H | OC₂H₅ | CH₃ | CN | |
| 1.176 | 2-Cl | 5-Cl | H | CH₃ | Cl | CN | |
| 1.177 | 2-Cl | 5-Cl | H | CH₃ | Cl | NO₂ | |
| 1.178 | 2-Cl | 5-Cl | H | CH₃ | Cl | Cl | |
| 1.179 | 2-Cl | 5-Cl | H | C₂H₅ | Cl | Cl | |
| 1.180 | 2-Cl | 5-Cl | H | C₂H₅ | Cl | Br | |
| 1.181 | 2-Cl | 5-Cl | H | OCH₃ | CH₃ | COOCH₃ | |
| 1.182 | 2-Cl | 5-Cl | H | CH₃ | CH₃ | COOC₂H₅ | |
| 1.183 | 2-Cl | 6-Cl | H | CH₃ | Cl | CH₃ | |
| 1.184 | 2-Cl | 6-Cl | H | CH₃ | CF₃ | CH₃ | |
| 1.185 | 2-Cl | 6-Cl | H | CH₃ | CF₃ | C₂H₅ | |
| 1.186 | 2-Cl | 6-Cl | H | OCH₃ | CF₃ | CH₃ | |
| 1.187 | 2-Cl | 6-Cl | H | SCH₃ | CF₃ | CH₃ | |
| 1.188 | 2-Cl | 6-Cl | H | CF₃ | Cl | CH₃ | m.p. 182–183° C. |
| 1.189 | 2-Cl | 6-Cl | H | SC₄H₉(n) | CF₃ | CH₃ | |
| 1.190 | 2-Cl | 6-Cl | H | SC₂H₅ | CH₃ | CH₃ | |
| 1.191 | 2-Cl | 6-Cl | H | SOC₂H₅ | CH₃ | CH₃ | |
| 1.192 | 2-Cl | 6-Cl | H | SO₂C₂H₅ | CH₃ | CH₃ | |
| 1.193 | 2-Cl | 6-Cl | H | C₂H₅ | CF₃ | CH₃ | |
| 1.194 | 2-Cl | 6-Cl | H | C₃H₇(n) | CF₃ | CH₃ | |
| 1.195 | 2-Cl | 6-Cl | H | C₄H₉(n) | CF₃ | CH₃ | |
| 1.196 | 2-Cl | 6-Cl | H | Cyclopropyl | CF₃ | CH₃ | |
| 1.197 | 2-Cl | 6-Cl | H | C₃H₇(i) | CF₃ | CH₃ | m.p. 164–165° C. |
| 1.198 | 2-Cl | 6-Cl | H | CH₃ | CF₂Cl | CH₃ | |
| 1.199 | 2-Cl | 6-Cl | H | CH₃ | CHF₂ | CH₃ | |
| 1.200 | 2-Cl | 6-Cl | H | CH₃ | CHCl₂ | CH₃ | |
| 1.201 | 2-Cl | 6-Cl | H | CH₃ | CHFCl | CH₃ | |
| 1.202 | 2-Cl | 6-Cl | H | CH₃ | CCl₂CF₃ | CH₃ | |
| 1.203 | 2-Cl | 6-Cl | H | CH₃ | OCHF₂ | CH₃ | |
| 1.204 | 2-Cl | 6-Cl | H | OCH₃ | CH₃ | NO₂ | |
| 1.205 | 2-Cl | 6-Cl | H | OCH₃ | CF₃ | NO₂ | |
| 1.206 | 2-Cl | 6-Cl | H | OCH₃ | CF₃ | Cl | |
| 1.207 | 2-Cl | 6-Cl | H | OCH₃ | CH₃ | CN | |
| 1.208 | 2-Cl | 6-Cl | H | CH₃ | Cl | CN | |
| 1.209 | 2-Cl | 6-Cl | H | CH₃ | Cl | NO₂ | |
| 1.210 | 2-Cl | 6-Cl | H | CH₃ | Cl | Cl | |
| 1.211 | 2-Cl | 6-Cl | H | CH₃ | Cl | Br | |
| 1.212 | 2-Cl | 6-Cl | H | OCH₃ | CH₃ | COOCH₃ | |
| 1.213 | 2-Cl | 3-Cl | H | CH₃ | Cl | CH₃ | |
| 1.214 | 2-Cl | 3-Cl | H | CH₃ | CF₃ | CH₃ | |
| 1.215 | 2-Cl | 3-Cl | H | C₂H₅ | CF₃ | CH₃ | |
| 1.216 | 2-Cl | 3-Cl | H | C₂H₅ | CF₂Cl | CH₃ | |
| 1.217 | 2-NO₂ | 3-CH₃ | H | CH₃ | Cl | CH₃ | |
| 1.218 | 2-NO₂ | 3-CH₃ | H | CH₃ | CF₃ | CH₃ | |
| 1.219 | 2-NO₂ | 3-CH₃ | H | C₂H₅ | CF₃ | CH₃ | |
| 1.220 | 2-NO₂ | 3-CH₃ | H | C₂H₅ | CF₂Cl | CH₃ | |
| 1.221 | 2-NO₂ | 3-Cl | H | CH₃ | Cl | CH₃ | |
| 1.222 | 2-NO₂ | 3-Cl | H | CH₃ | CF₃ | CH₃ | |
| 1.223 | 2-NO₂ | 3-Cl | H | OCH₃ | CH₃ | CH₃ | |
| 1.224 | 2-NO₂ | 3-Cl | H | C₂H₅ | CF₃ | CH₃ | |
| 1.225 | 2-NO₂ | 3-Cl | H | C₂H₅ | CF₂Cl | CH₃ | |
| 1.226 | 2-NO₂ | 5-Cl | H | CH₃ | Cl | CH₃ | |

TABLE 1-continued

Compounds of formula:

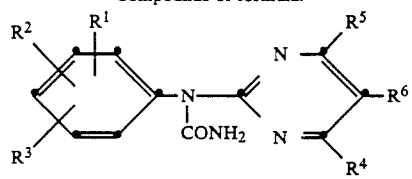

(I)

| | | | | | | | |
|---|---|---|---|---|---|---|---|
| 1.227 | 2-NO$_2$ | 5-Cl | H | CH$_3$ | CF$_3$ | CH$_3$ | |
| 1.228 | 2-NO$_2$ | 5-Cl | H | C$_2$H$_5$ | CF$_3$ | CH$_3$ | |
| 1.229 | 2-NO$_2$ | 5-Cl | H | CH$_3$ | CF$_2$Cl | CH$_3$ | |
| 1.230 | 2-NO$_2$ | 5-Cl | H | SCH$_3$ | CH$_3$ | CH$_3$ | |
| 1.231 | 2-NO$_2$ | 5-Cl | H | SOCH$_3$ | CH$_3$ | CH$_3$ | |
| 1.232 | 2-NO$_2$ | 5-Cl | H | SO$_2$CH$_3$ | CH$_3$ | CH$_3$ | |
| 1.233 | 2-NO$_2$ | 5-Cl | H | CN | CH$_3$ | CH$_3$ | |
| 1.234 | 2-NO$_2$ | 5-Cl | H | OCH$_3$ | CF$_3$ | CH$_3$ | |
| 1.235 | 2-NO$_2$ | 5-Cl | H | SCH$_3$ | CF$_3$ | CH$_3$ | |
| 1.236 | 2-NO$_2$ | 5-Cl | H | OC$_3$H$_7$(i) | CF$_3$ | CH$_3$ | |
| 1.237 | 2-NO$_2$ | 5-Cl | H | SC$_2$H$_5$ | CF$_3$ | CH$_3$ | |
| 1.238 | 2-NO$_2$ | 5-Cl | H | C$_3$H$_7$(i) | CF$_3$ | CH$_3$ | |
| 1.239 | 2-NO$_2$ | 6-Cl | H | CH$_3$ | Cl | CH$_3$ | |
| 1.240 | 2-NO$_2$ | 6-Cl | H | CH$_3$ | CF$_3$ | CH$_3$ | |
| 1.241 | 2-NO$_2$ | 6-Cl | H | OCH$_3$ | CF$_3$ | CH$_3$ | |
| 1.242 | 2-NO$_2$ | 6-Cl | H | SCH$_3$ | CF$_3$ | CH$_3$ | |
| 1.243 | 2-NO$_2$ | 6-Cl | H | SOCH$_3$ | CF$_3$ | CH$_3$ | |
| 1.244 | 2-NO$_2$ | 6-Cl | H | SO$_2$CH$_3$ | CF$_3$ | CH$_3$ | |
| 1.245 | 2-NO$_2$ | 6-Cl | H | C$_2$H$_5$ | CF$_3$ | CH$_3$ | |
| 1.246 | 2-NO$_2$ | 6-Cl | H | Cyclopropyl | CF$_3$ | CH$_3$ | |
| 1.247 | 2-NO$_2$ | 6-Cl | H | C$_3$H$_7$(i) | CF$_3$ | CH$_3$ | |
| 1.248 | 2-NO$_2$ | 6-Cl | H | CH$_3$ | CF$_2$Cl | CH$_3$ | |
| 1.249 | 2-NO$_2$ | 5-CH$_3$ | H | CH$_3$ | Cl | CH$_3$ | |
| 1.250 | 2-NO$_2$ | 5-CH$_3$ | H | CH$_3$ | CF$_3$ | CH$_3$ | |
| 1.251 | 2-NO$_2$ | 5-CH$_3$ | H | OCH$_3$ | CF$_3$ | CH$_3$ | |
| 1.252 | 2-NO$_2$ | 5-CH$_3$ | H | CF$_3$ | Cl | CH$_3$ | |
| 1.253 | 2-NO$_2$ | 5-CH$_3$ | H | SCH$_3$ | CF$_3$ | CH$_3$ | |
| 1.254 | 2-NO$_2$ | 5-CH$_3$ | H | C$_2$H$_5$ | CF$_3$ | CH$_3$ | |
| 1.255 | 2-NO$_2$ | 5-CH$_3$ | H | C$_3$H$_7$(n) | CF$_3$ | CH$_3$ | |
| 1.256 | 2-NO$_2$ | 5-CH$_3$ | H | C$_3$H$_7$(i) | CF$_3$ | CH$_3$ | |
| 1.257 | 2-NO$_2$ | 5-CH$_3$ | H | Cyclopropyl | CF$_3$ | CH$_3$ | |
| 1.258 | 2-NO$_2$ | 5-CH$_3$ | H | CH$_3$ | CF$_2$Cl | CH$_3$ | |
| 1.259 | 2-NO$_2$ | 5-CH$_3$ | H | CH$_3$ | CHFCl | CH$_3$ | |
| 1.260 | 2-NO$_2$ | 5-CH$_3$ | H | OCH$_3$ | CH$_3$ | NO$_2$ | |
| 1.261 | 2-NO$_2$ | 5-CH$_3$ | H | OCH$_3$ | CH$_3$ | CN | |
| 1.262 | 2-NO$_2$ | 5-CH$_3$ | H | OCH$_3$ | CH$_3$ | Cl | |
| 1.263 | 2-NO$_2$ | 5-CH$_3$ | H | OCH$_3$ | CH$_3$ | COOCH$_3$ | |
| 1.264 | 2-NO$_2$ | 5-CH$_3$ | H | OC$_3$H$_7$(n) | CF$_3$ | CH$_3$ | |
| 1.265 | 2-NO$_2$ | 5-CH$_3$ | H | SC$_2$H$_5$ | CF$_3$ | CH$_3$ | |
| 1.266 | 2-NO$_2$ | 6-CH$_3$ | H | CH$_3$ | Cl | CH$_3$ | |
| 1.267 | 2-NO$_2$ | 6-CH$_3$ | H | OCH$_3$ | CH$_3$ | CH$_3$ | |
| 1.268 | 2-NO$_2$ | 6-CH$_3$ | H | SCH$_3$ | CH$_3$ | CH$_3$ | |
| 1.269 | 2-NO$_2$ | 6-CH$_3$ | H | SOCH$_3$ | CH$_3$ | CH$_3$ | |
| 1.270 | 2-NO$_2$ | 6-CH$_3$ | H | SO$_2$CH$_3$ | CH$_3$ | CH$_3$ | |
| 1.271 | 2-NO$_2$ | 6-CH$_3$ | H | CF$_3$ | Cl | CH$_3$ | |
| 1.272 | 2-NO$_2$ | 6-CH$_3$ | H | OCH$_3$ | CF$_3$ | CH$_3$ | |
| 1.273 | 2-NO$_2$ | 6-CH$_3$ | H | OC$_2$H$_5$ | CF$_3$ | CH$_3$ | |
| 1.274 | 2-NO$_2$ | 6-CH$_3$ | H | SCH$_3$ | CF$_3$ | CH$_3$ | |
| 1.275 | 2-NO$_2$ | 6-CH$_3$ | H | SOCH$_3$ | CF$_3$ | CH$_3$ | |
| 1.276 | 2-NO$_2$ | 6-CH$_3$ | H | SO$_2$CH$_3$ | CF$_3$ | CH$_3$ | |
| 1.277 | 2-NO$_2$ | 6-CH$_3$ | H | SC$_3$H$_7$(i) | CF$_3$ | CH$_3$ | |
| 1.278 | 2-NO$_2$ | 6-CH$_3$ | H | CF$_3$ | Cl | C$_2$H$_5$ | |
| 1.279 | 2-NO$_2$ | 6-CH$_3$ | H | OCH$_3$ | CF$_3$ | C$_2$H$_5$ | |
| 1.280 | 2-NO$_2$ | 6-CH$_3$ | H | SCH$_3$ | CF$_3$ | C$_2$H$_5$ | |
| 1.281 | 2-NO$_2$ | 6-CH$_3$ | H | CF$_3$ | Cl | C$_3$H$_7$(i) | |
| 1.282 | 2-NO$_2$ | 6-CH$_3$ | H | OCH$_3$ | CF$_3$ | C$_3$H$_7$(i) | |
| 1.283 | 2-NO$_2$ | 6-CH$_3$ | H | SC$_2$H$_5$ | CF$_3$ | C$_3$H$_7$(i) | |
| 1.284 | 2-NO$_2$ | 6-CH$_3$ | H | CH$_3$ | CF$_3$ | CH$_3$ | m.p. 165-166° C. |
| 1.285 | 2-NO$_2$ | 6-CH$_3$ | H | C$_2$H$_5$ | CF$_3$ | CH$_3$ | m.p. 158-159° C. |
| 1.286 | 2-NO$_2$ | 6-CH$_3$ | H | C$_3$H$_7$(n) | CF$_3$ | CH$_3$ | |
| 1.287 | 2-NO$_2$ | 6-CH$_3$ | H | C$_3$H$_7$(i) | CF$_3$ | CH$_3$ | |
| 1.288 | 2-NO$_2$ | 6-CH$_3$ | H | Cyclopropyl | CF$_3$ | CH$_3$ | |
| 1.289 | 2-NO$_2$ | 6-CH$_3$ | H | C$_4$H$_9$(n) | CF$_3$ | CH$_3$ | |
| 1.290 | 2-NO$_2$ | 6-CH$_3$ | H | CH$_3$ | CF$_2$Cl | CH$_3$ | |
| 1.291 | 2-NO$_2$ | 6-CH$_3$ | H | CH$_3$ | CHF$_2$ | CH$_3$ | |
| 1.292 | 2-NO$_2$ | 6-CH$_3$ | H | CH$_3$ | CHCl$_2$ | CH$_3$ | |
| 1.293 | 2-NO$_2$ | 6-CH$_3$ | H | CH$_3$ | CHFCl | CH$_3$ | |
| 1.294 | 2-NO$_2$ | 6-CH$_3$ | H | CH$_3$ | C$_2$F$_5$ | CH$_3$ | |
| 1.295 | 2-NO$_2$ | 6-CH$_3$ | H | CH$_3$ | C$_3$H$_7$(n) | CH$_3$ | |
| 1.296 | 2-NO$_2$ | 6-CH$_3$ | H | C$_2$H$_5$ | CF$_2$Cl | CH$_3$ | |
| 1.297 | 2-NO$_2$ | 6-CH$_3$ | H | C$_3$H$_7$(i) | CF$_2$Cl | CH$_3$ | |
| 1.298 | 2-NO$_2$ | 6-CH$_3$ | H | Cyclopropyl | CF$_2$Cl | CH$_3$ | |
| 1.299 | 2-NO$_2$ | 6-CH$_3$ | H | C$_2$H$_5$ | C$_2$F$_5$ | CH$_3$ | |

TABLE 1-continued

Compounds of formula: (I)

| | $R^2$ | $R^1$ | $R^3$ | $R^4$ | $R^5$ | $R^6$ | |
|---|---|---|---|---|---|---|---|
| 1.300 | 2-NO$_2$ | 6-CH$_3$ | H | C$_2$H$_5$ | CHCl$_2$ | CH$_3$ | |
| 1.301 | 2-NO$_2$ | 6-CH$_3$ | H | CH$_3$ | CCl$_2$CF$_3$ | CH$_3$ | |
| 1.302 | 2-NO$_2$ | 6-CH$_3$ | H | CH$_3$ | OCHF$_2$ | CH$_3$ | |
| 1.303 | 2-NO$_2$ | 6-CH$_3$ | H | CH$_3$ | Cl | CH$_2$CH$_2$Cl | |
| 1.304 | 2-NO$_2$ | 6-CH$_3$ | H | OCH$_3$ | CH$_3$ | CH$_2$CH$_2$OCH$_3$ | |
| 1.305 | 2-NO$_2$ | 6-CH$_3$ | H | SCH$_3$ | CH$_3$ | CH$_2$CH$_2$SCH$_3$ | |
| 1.306 | 2-NO$_2$ | 6-CH$_3$ | H | CN | CH$_3$ | CH$_3$ | |
| 1.307 | 2-NO$_2$ | 6-CH$_3$ | H | CH$_3$ | CF$_3$ | Phenyl | |
| 1.308 | 2-NO$_2$ | 6-CH$_3$ | H | CH$_3$ | Cl | Phenyl | |
| 1.309 | 2-NO$_2$ | 6-CH$_3$ | H | OCH$_3$ | CH$_3$ | NO$_2$ | |
| 1.310 | 2-NO$_2$ | 6-CH$_3$ | H | OCH$_3$ | CH$_3$ | Cl | |
| 1.311 | 2-NO$_2$ | 6-CH$_3$ | H | OCH$_3$ | CH$_3$ | CN | |
| 1.312 | 2-NO$_2$ | 6-CH$_3$ | H | CH$_3$ | Cl | CN | |
| 1.313 | 2-NO$_2$ | 6-CH$_3$ | H | CH$_3$ | Cl | NO$_2$ | |
| 1.314 | 2-NO$_2$ | 6-CH$_3$ | H | CH$_3$ | Cl | Cl | |
| 1.315 | 2-NO$_2$ | 6-CH$_3$ | H | SCH$_3$ | CH$_3$ | Cl | |
| 1.316 | 2-NO$_2$ | 6-CH$_3$ | H | CH$_3$ | Cl | OCH$_3$ | |
| 1.317 | 2-NO$_2$ | 6-CH$_3$ | H | OCH$_3$ | CH$_3$ | COOC$_2$H$_5$ | |
| 1.318 | 2-NO$_2$ | 6-CH$_3$ | H | CH$_3$ | CH$_3$ | COOCH$_3$ | |
| 1.319 | 2-NO$_2$ | 5-F | H | CH$_3$ | Cl | CH$_3$ | |
| 1.320 | 2-NO$_2$ | 5-F | H | CH$_3$ | CF$_3$ | CH$_3$ | |
| 1.321 | 2-NO$_2$ | 5-F | H | C$_2$H$_5$ | CF$_3$ | CH$_3$ | |
| 1.322 | 2-NO$_2$ | 6-F | H | CH$_3$ | Cl | CH$_3$ | |
| 1.323 | 2-NO$_2$ | 6-F | H | OCH$_3$ | CH$_3$ | CH$_3$ | |
| 1.324 | 2-NO$_2$ | 6-F | H | CH$_3$ | CF$_3$ | CH$_3$ | |
| 1.325 | 2-NO$_2$ | 6-F | H | CH$_3$ | CF$_2$Cl | CH$_3$ | |
| 1.326 | 2-NO$_2$ | 6-Br | H | CH$_3$ | Cl | CH$_3$ | |
| 1.327 | 2-NO$_2$ | 6-Br | H | CH$_3$ | CF$_3$ | CH$_3$ | |
| 1.328 | 2-NO$_2$ | 6-Br | H | C$_2$H$_5$ | CF$_3$ | CH$_3$ | |
| 1.329 | 2-NO$_2$ | 6-Br | H | Cyclopropyl | CF$_3$ | CH$_3$ | |
| 1.330 | 2-NO$_2$ | 6-Br | H | CH$_3$ | CHFCl | CH$_3$ | |
| 1.331 | 2-NO$_2$ | 6-Br | H | CH$_3$ | CF$_2$Cl | CH$_3$ | |
| 1.332 | 2-NO$_2$ | 6-Br | H | CH$_3$ | CHCl$_2$ | CH$_3$ | |
| 1.333 | 2-F | 5-F | H | CH$_3$ | Cl | CH$_3$ | |
| 1.334 | 2-F | 5-F | H | CH$_3$ | CF$_3$ | CH$_3$ | |
| 1.335 | 2-F | 5-F | H | C$_2$H$_5$ | CF$_3$ | CH$_3$ | |
| 1.336 | 2-F | 5-F | H | C$_2$H$_5$ | C$_2$F$_5$ | CH$_3$ | |
| 1.337 | 2-F | 5-F | H | C$_2$H$_5$ | CF$_2$Cl | CH$_3$ | |
| 1.338 | 2-F | 6-F | H | CH$_3$ | Cl | CH$_3$ | |
| 1.339 | 2-F | 6-F | H | CH$_3$ | CF$_3$ | CH$_3$ | |
| 1.340 | 2-F | 6-F | H | C$_2$H$_5$ | CF$_3$ | CH$_3$ | m.p. 144–145° C. |
| 1.341 | 2-F | 6-F | H | OCH$_3$ | CF$_3$ | CH$_3$ | |
| 1.342 | 2-F | 6-F | H | SCH$_3$ | CF$_3$ | CH$_3$ | |
| 1.343 | 2-F | 6-Cl | H | CH$_3$ | Cl | CH$_3$ | |
| 1.344 | 2-F | 6-Cl | H | CH$_3$ | CF$_3$ | CH$_3$ | |
| 1.345 | 2-F | 6-Cl | H | CH$_3$ | C$_2$F$_5$ | CH$_3$ | |
| 1.346 | 2-F | 6-Cl | H | C$_2$H$_5$ | CF$_3$ | CH$_3$ | |
| 1.347 | 2-F | 6-Cl | H | C$_2$H$_5$ | CF$_2$Cl | CH$_3$ | |
| 1.348 | 2-CF$_3$ | 6-Cl | H | CH$_3$ | Cl | CH$_3$ | |
| 1.349 | 2-CF$_3$ | 6-Cl | H | CH$_3$ | CF$_3$ | CH$_3$ | |
| 1.350 | 2-CF$_3$ | 6-Cl | H | C$_2$H$_5$ | CF$_3$ | CH$_3$ | |
| 1.351 | 2-CF$_3$ | 6-Cl | H | C$_2$H$_5$ | CF$_2$Cl | CH$_3$ | |
| 1.352 | 2-CF$_3$ | 6-Cl | H | CH$_3$ | C$_2$F$_5$ | CH$_3$ | |
| 1.353 | 2-CF$_3$ | 6-CH$_3$ | H | CH$_3$ | Cl | CH$_3$ | |
| 1.354 | 2-CF$_3$ | 6-CH$_3$ | H | CH$_3$ | CF$_3$ | CH$_3$ | |
| 1.355 | 2-CF$_3$ | 6-CH$_3$ | H | C$_2$H$_5$ | CF$_3$ | CH$_3$ | |
| 1.356 | 2-CF$_3$ | 6-CH$_3$ | H | Cyclopropyl | CF$_3$ | CH$_3$ | |
| 1.357 | 2-OCHF$_2$ | 5-Cl | H | CH$_3$ | Cl | CH$_3$ | |
| 1.358 | 2-OCHF$_2$ | 5-Cl | H | CH$_3$ | CF$_3$ | CH$_3$ | |
| 1.359 | 2-OCHF$_2$ | 5-Cl | H | C$_2$H$_5$ | CF$_3$ | CH$_3$ | |
| 1.360 | 2-OCHF$_2$ | 5-Cl | H | CH$_3$ | CF$_2$Cl | CH$_3$ | |
| 1.361 | 2-OCHF$_2$ | 5-Cl | H | CH$_3$ | CHCl$_2$ | CH$_3$ | |
| 1.362 | 2-OCHF$_2$ | 5-Cl | H | CF$_3$ | Cl | CH$_3$ | |
| 1.363 | 2-OCHF$_2$ | 5-Cl | H | OCH$_3$ | CF$_3$ | CH$_3$ | |
| 1.364 | 2-OCHF$_2$ | 5-Cl | H | SC$_2$H$_5$ | CF$_3$ | CH$_3$ | |
| 1.365 | 2-OCHF$_2$ | 5-Cl | H | CF$_3$ | Cl | C$_2$H$_5$ | |
| 1.366 | 2-OCHF$_2$ | 5-Cl | H | OCH$_3$ | CF$_3$ | C$_2$H$_5$ | |
| 1.367 | 2-OCHF$_2$ | 5-Cl | H | OC$_2$H$_5$ | CF$_3$ | C$_2$H$_5$ | |
| 1.368 | 2-OCHF$_2$ | 5-Cl | H | SCH$_3$ | CF$_3$ | C$_2$H$_5$ | |
| 1.369 | 2-OCF$_3$ | 5-Cl | H | CH$_3$ | Cl | CH$_3$ | |
| 1.370 | 2-OCF$_3$ | 5-Cl | H | CH$_3$ | CF$_3$ | CH$_3$ | |
| 1.371 | 2-OCF$_3$ | 5-Cl | H | C$_2$H$_5$ | CF$_3$ | CH$_3$ | |
| 1.372 | 2-OCF$_3$ | 5-Cl | H | CH$_3$ | C$_2$H$_5$ | CH$_3$ | |

TABLE 1-continued

Compounds of formula:

$$\text{(I)}$$

| | $R^2$ | $R^1$ | $R^3$ | | $R^5$ | $R^6$ | $R^4$ |
|---|---|---|---|---|---|---|---|

| | | | | | | | |
|---|---|---|---|---|---|---|---|
| 1.373 | 2-OCF$_3$ | 5-Cl | H | CH$_3$ | CF$_2$Cl | CH$_3$ | |
| 1.374 | 2-C$_2$H$_5$ | 6-CH$_3$ | H | CH$_3$ | Cl | CH$_3$ | |
| 1.375 | 2-C$_2$H$_5$ | 6-CH$_3$ | H | CH$_3$ | CF$_3$ | CH$_3$ | |
| 1.376 | 2-C$_2$H$_5$ | 6-CH$_3$ | H | OCH$_3$ | CF$_3$ | CH$_3$ | |
| 1.377 | 2-C$_2$H$_5$ | 6-CH$_3$ | H | SCH$_3$ | CF$_3$ | CH$_3$ | |
| 1.378 | 2-C$_2$H$_5$ | 6-CH$_3$ | H | OC$_3$H$_7$(i) | CF$_3$ | CH$_3$ | |
| 1.379 | 2-CF$_3$ | 6-NO$_2$ | H | CH$_3$ | Cl | CH$_3$ | |
| 1.380 | 2-CF$_3$ | 6-NO$_2$ | H | CH$_3$ | CF$_3$ | CH$_3$ | |
| 1.381 | 2-NO$_2$ | 6-NO$_2$ | H | CH$_3$ | CF$_3$ | CH$_3$ | |
| 1.382 | 2-NO$_2$ | 6-NO$_2$ | H | OCH$_3$ | CF$_3$ | CH$_3$ | |
| 1.383 | 2-Cl | 6-Cl | 3-CH$_3$ | CH$_3$ | Cl | CH$_3$ | |
| 1.384 | 2-Cl | 6-Cl | 3-CH$_3$ | CH$_3$ | CF$_3$ | CH$_3$ | |
| 1.385 | 2-Cl | 6-Cl | 3-CH$_3$ | CH$_3$ | CF$_3$ | C$_2$H$_5$ | |
| 1.386 | 2-Cl | 6-Cl | 3-Cl | CH$_3$ | Cl | CH$_3$ | |
| 1.387 | 2-Cl | 6-Cl | 3-Cl | CH$_3$ | CF$_3$ | CH$_3$ | |
| 1.388 | 2-Cl | 6-Cl | 3-Cl | C$_2$H$_5$ | CF$_3$ | CH$_3$ | |
| 1.389 | 2-CH$_3$ | 3-Cl | H | CH$_3$ | Cl | CH$_3$ | |
| 1.390 | 2-CH$_3$ | 3-Cl | H | CH$_3$ | CF$_3$ | CH$_3$ | |
| 1.391 | 2-CH$_3$ | 3-Cl | H | C$_2$H$_5$ | CF$_3$ | CH$_3$ | |
| 1.392 | 2-CH$_3$ | 5-Cl | H | CH$_3$ | Cl | CH$_3$ | |
| 1.393 | 2-CH$_3$ | 5-Cl | H | CH$_3$ | CF$_3$ | CH$_3$ | |
| 1.394 | 2-CH$_3$ | 5-Cl | H | C$_2$H$_5$ | CF$_3$ | CH$_3$ | |
| 1.395 | 2-CH$_3$ | 5-Cl | H | C$_2$H$_5$ | CF$_2$Cl | CH$_3$ | |
| 1.396 | 2-CH$_3$ | 5-Cl | H | OCH$_3$ | CF$_3$ | CH$_3$ | |
| 1.397 | 2-CH$_3$ | 6-Cl | H | CH$_3$ | Cl | CH$_3$ | |
| 1.398 | 2-CH$_3$ | 6-Cl | H | CH$_3$ | CF$_3$ | CH$_3$ | |
| 1.399 | 2-CH$_3$ | 6-Cl | H | C$_2$H$_5$ | CF$_3$ | CH$_3$ | |
| 1.400 | 2-CH$_3$ | 6-Cl | H | C$_2$H$_5$ | CHCl$_2$ | CH$_3$ | |
| 1.401 | 2-CH$_3$ | 6-Cl | H | C$_2$H$_5$ | CF$_2$Cl | CH$_3$ | |
| 1.402 | 2-CH$_3$ | 6-Cl | H | OC$_2$H$_5$ | CF$_3$ | CH$_3$ | |
| 1.403 | 2-CH$_3$ | 6-Cl | H | SCH$_3$ | CF$_3$ | CH$_3$ | |
| 1.404 | 2-CH$_3$ | 6-Cl | H | OC$_4$H$_9$(n) | CF$_3$ | CH$_3$ | |
| 1.405 | 2-CH$_3$ | 6-Cl | H | CH$_3$ | Cl | SCH$_3$ | |
| 1.406 | 2-CH$_3$ | 6-CH$_3$ | H | CH$_3$ | Cl | CH$_3$ | |
| 1.407 | 2-CH$_3$ | 6-CH$_3$ | H | CH$_3$ | CF$_3$ | CH$_3$ | |
| 1.408 | 2-CH$_3$ | 6-CH$_3$ | H | C$_2$H$_5$ | CF$_3$ | CH$_3$ | |
| 1.409 | 2-CH$_3$ | 6-CH$_3$ | H | Cyclopropyl | CF$_3$ | CH$_3$ | |
| 1.410 | 2-CH$_3$ | 6-CH$_3$ | H | C$_2$H$_5$ | CF$_2$Cl | CH$_3$ | |
| 1.411 | 2-Cl | 3-CH$_3$ | H | CH$_3$ | Cl | CH$_3$ | |
| 1.412 | 2-Cl | 3-CH$_3$ | H | CH$_3$ | CF$_3$ | CH$_3$ | |
| 1.413 | 2-Cl | 3-CH$_3$ | H | C$_2$H$_5$ | CF$_3$ | CH$_3$ | |
| 1.414 | 2-Cl | 5-CH$_3$ | H | CH$_3$ | Cl | CH$_3$ | |
| 1.415 | 2-Cl | 5-CH$_3$ | H | CH$_3$ | CF$_3$ | CH$_3$ | |
| 1.416 | 2-Cl | 5-CH$_3$ | H | C$_2$H$_5$ | CF$_3$ | CH$_3$ | |
| 1.417 | 2-Cl | 5-CH$_3$ | H | C$_2$H$_5$ | CF$_2$Cl | CH$_3$ | |
| 1.418 | 2-NO$_2$ | H | H | CH$_2$Cl | Cl | CH$_3$ | |
| 1.419 | 2-NO$_2$ | H | H | CH$_2$OCH$_3$ | Cl | CH$_3$ | |
| 1.420 | 2-NO$_2$ | H | H | CH$_3$ | Cl | SCH$_3$ | |
| 1.421 | 2-NO$_2$ | H | H | CH$_3$ | Cl | SC$_2$H$_5$ | |
| 1.422 | 2-NO$_2$ | H | H | CH$_3$ | Cl | OCH$_3$ | |
| 1.423 | 2-NO$_2$ | H | H | CH$_3$ | Cl | OC$_2$H$_5$ | |
| 1.424 | 2-NO$_2$ | 6-CH$_3$ | H | CH$_2$OCH$_3$ | Cl | CH$_3$ | |
| 1.425 | 2-NO$_2$ | 6-CH$_3$ | H | CH$_3$ | Cl | SCH$_3$ | |
| 1.426 | 2-NO$_2$ | 6-CH$_3$ | H | CH$_3$ | Cl | OC$_2$H$_5$ | |
| 1.427 | 2-NO$_2$ | 6-CH$_3$ | H | CH$_3$ | Cl | SC$_2$H$_5$ | |
| 1.428 | 2-NO$_2$ | 6-CH$_3$ | H | CH$_3$ | Cl | SC$_3$H$_7$(i) | |
| 1.429 | 2-Cl | 5-Cl | H | CH$_3$ | Cl | OCH$_3$ | |
| 1.430 | 2-Cl | 5-Cl | H | CH$_3$ | Cl | SCH$_3$ | |
| 1.431 | 2-Cl | 5-Cl | H | CH$_3$ | Cl | OC$_2$H$_5$ | |
| 1.432 | 2-Cl | 6-Cl | H | CH$_2$OCH$_3$ | CF$_3$ | CH$_3$ | |
| 1.433 | 2-Cl | 6-Cl | H | CH$_2$OCH$_3$ | Cl | CH$_3$ | |
| 1.434 | 2-Cl | 6-Cl | H | CH$_3$ | Cl | OCH$_3$ | |
| 1.435 | 2-Cl | 6-Cl | H | CH$_3$ | Cl | SCH$_3$ | |
| 1.436 | 2-Cl | 6-Cl | H | CH$_3$ | Cl | OC$_2$H$_5$ | |
| 1.437 | 2-Cl | 6-Cl | H | CH$_3$ | Cl | SC$_2$H$_5$ | |
| 1.438 | 2-NO$_2$ | H | H | CH$_2$COOCH$_3$ | CF$_3$ | CH$_3$ | |
| 1.439 | 2-NO$_2$ | H | H | $\underset{\text{CH}_2\text{CCH}_3}{\overset{\text{O}}{\|}}$ | CF$_3$ | CH$_3$ | |
| 1.440 | 2-OCH$_3$ | 5-Cl | H | CH$_3$ | Cl | CH$_3$ | |
| 1.441 | 2-OCH$_3$ | 5-Cl | H | CH$_3$ | CF$_3$ | CH$_3$ | |

TABLE 1-continued

Compounds of formula: (I)

| Comp. No. | R$^1$ | R$^2$ | R$^3$ | R$^5$ | R$^6$ | R$^4$ | Phys. data |
|---|---|---|---|---|---|---|---|
| 1.442 | 2-OCH$_3$ | 5-Cl | H | C$_2$H$_5$ | CF$_3$ | CH$_3$ | |
| 1.443 | 2-OCH$_3$ | 5-Cl | H | CH$_3$ | CF$_2$Cl | CH$_3$ | |
| 1.444 | 2-OCH$_3$ | 5-Cl | H | CH$_3$ | C$_2$F$_5$ | CH$_3$ | |
| 1.445 | 2-OCH$_3$ | 5-Cl | H | Cyclopropyl | CF$_3$ | CH$_3$ | |

| Comp. No. | R$^1$ | R$^2$ | R$^3$ | —R$^5$—R$^6$— | R$^4$ | Phys. data |
|---|---|---|---|---|---|---|
| 1.446 | 2-NO$_2$ | H | H | —CH$_2$—CH$_2$— | CF$_3$ | |
| 1.447 | 2-NO$_2$ | H | H | —CHCH$_3$—CH$_2$— | CF$_3$ | |
| 1.448 | 2-NO$_2$ | H | H | —CH$_2$—CH$_2$— | CF$_2$Cl | |
| 1.449 | 2-NO$_2$ | H | H | —(CH$_2$)$_3$— | CF$_3$ | m.p. 160–161° C. |
| 1.450 | 2-NO$_2$ | H | H | —(CH$_2$)$_3$— | Cl | |
| 1.451 | 2-NO$_2$ | H | H | —(CH$_2$)$_3$— | OCH$_3$ | |
| 1.452 | 2-NO$_2$ | H | H | —(CH$_2$)$_3$— | SCH$_3$ | |
| 1.453 | 2-NO$_2$ | H | H | —(CH$_2$)$_3$— | SOCH$_3$ | |
| 1.454 | 2-NO$_2$ | H | H | —(CH$_2$)$_3$— | SO$_2$CH$_3$ | |
| 1.455 | 2-NO$_2$ | H | H | —CHCH$_3$—CH$_2$—CH$_2$— | CF$_3$ | |
| 1.456 | 2-NO$_2$ | H | H | —CHCH$_3$—CH$_2$—CH$_2$— | Cl | |
| 1.457 | 2-NO$_2$ | H | H | —CHCH$_3$—CH$_2$—CH$_2$— | CHCl$_2$ | |
| 1.458 | 2-NO$_2$ | H | H | —CHCH$_3$—CH$_2$—CH$_2$— | CHFCl | |
| 1.459 | 2-NO$_2$ | H | H | —CHCH$_3$—CH$_2$—CH$_2$— | CF$_2$Cl | |
| 1.460 | 2-NO$_2$ | H | H | —C(CH$_3$)$_2$—CH$_2$—CH$_2$— | CF$_3$ | |
| 1.461 | 2-NO$_2$ | H | H | —C(CH$_3$)$_2$—CH$_2$CH$_2$ | Cl | |
| 1.462 | 2-NO$_2$ | H | H | —C(CH$_3$)$_2$—CH$_2$—CH$_2$ | CF$_2$CF$_3$ | |
| 1.463 | 2-NO$_2$ | H | H | —CH=CCH$_3$—CH$_2$— | CF$_3$ | |
| 1.464 | 2-NO$_2$ | H | H | —CH=CCH$_3$—CH$_2$— | Cl | |
| 1.465 | 2-NO$_2$ | H | H | —CH=CCH$_3$—CH$_2$— | CHF$_2$ | |
| 1.466 | 2-NO$_2$ | H | H | —CH$_2$—CHCH$_3$—CH$_2$— | Cl | |
| 1.467 | 2-NO$_2$ | H | H | —CH$_2$—CHCH$_3$—CH$_2$— | CF$_3$ | |
| 1.468 | 2-NO$_2$ | H | H | —CH$_2$—CH$_2$—CHCH$_3$— | Cl | |
| 1.469 | 2-NO$_2$ | H | H | —CH$_2$—CH$_2$—CHCH$_3$— | CF$_3$ | |
| 1.470 | 2-NO$_2$ | H | H | —CH(COOCH$_3$)—CH$_2$—CH$_2$— | Cl | |
| 1.471 | 2-NO$_2$ | H | H | —CH(COOC$_2$H$_5$)—CH$_2$—CH$_2$— | Cl | |
| 1.472 | 2-NO$_2$ | H | H | —CH$_2$—CH$_2$—S— | Cl | |
| 1.473 | 2-NO$_2$ | H | H | —CH$_2$—CH$_2$—S— | CF$_3$ | |
| 1.474 | 2-NO$_2$ | H | H | —CH$_2$—CH$_2$—S— | CF$_2$Cl | |
| 1.475 | 2-NO$_2$ | H | H | —CH$_2$—CH$_2$—S— | CHCl$_2$ | |
| 1.476 | 2-NO$_2$ | H | H | —CH$_2$—C(CH$_3$)$_2$—CH$_2$— | Cl | |
| 1.477 | 2-NO$_2$ | H | H | —CH$_2$—C(CH$_3$)$_2$—CH$_2$— | CF$_3$ | |
| 1.478 | 2-NO$_2$ | H | H | —CH$_2$—C(CH$_3$)$_2$—CH$_2$— | CF$_2$CF$_3$ | |
| 1.479 | 2-NO$_2$ | H | H | —CH$_2$—CH$_2$—C(CH$_3$)$_2$— | Cl | |
| 1.480 | 2-NO$_2$ | H | H | —CH$_2$—CH$_2$—C(CH$_3$)$_2$— | CF$_3$ | |
| 1.481 | 2-NO$_2$ | H | H | —CH$_2$—CH$_2$—C(CH$_3$)$_2$— | CF$_2$CF$_3$ | |
| 1.482 | 2-NO$_2$ | H | H | —CHCH$_3$—CHCH$_3$—CH$_2$— | Cl | |
| 1.483 | 2-NO$_2$ | H | H | —CHCH$_3$—CHCH$_3$—CH$_2$— | CF$_3$ | |
| 1.484 | 2-NO$_2$ | H | H | —CHCH$_3$—CHCH$_3$—CH$_2$— | CF$_2$Cl | |
| 1.485 | 2-NO$_2$ | H | H | —CH(C$_2$H$_5$)—CH$_2$—CH$_2$— | Cl | |
| 1.486 | 2-NO$_2$ | H | H | —CH(C$_2$H$_5$)—CH$_2$—CH$_2$— | CF$_3$ | |
| 1.487 | 2-NO$_2$ | H | H | —C(CH$_3$)(C$_2$H$_5$)—CH$_2$—CH$_2$ | Cl | |
| 1.488 | 2-NO$_2$ | H | H | —C(CH$_3$)(C$_2$H$_5$)—CH$_2$CH$_2$ | CF$_3$ | |
| 1.489 | 2-NO$_2$ | H | H | —CHCH$_3$—(CH$_2$)$_3$— | Cl | |
| 1.490 | 2-NO$_2$ | H | H | —CHCH$_3$—(CH$_2$)$_3$— | CF$_3$ | m.p. 170–171° C. |
| 1.491 | 2-NO$_2$ | H | H | —CHCH$_3$—(CH$_2$)$_3$— | CF$_2$CF$_3$ | |
| 1.492 | 2-NO$_2$ | H | H | —CHCH$_3$—(CH$_2$)$_3$— | CF$_2$Cl | |
| 1.493 | 2-NO$_2$ | H | H | —CHCH$_3$—(CH$_2$)$_3$— | CHF$_2$ | |
| 1.494 | 2-NO$_2$ | H | H | —(CH$_2$)$_4$— | Cl | m.p. 168–170° C. |
| 1.495 | 2-NO$_2$ | H | H | —(CH$_2$)$_4$— | OCH$_3$ | |
| 1.496 | 2-NO$_2$ | H | H | —(CH$_2$)$_4$— | CF$_3$ | m.p. 163–164° C. |
| 1.497 | 2-NO$_2$ | H | H | —(CH$_2$)$_4$— | CHF$_2$ | m.p. 154–155° C. |
| 1.498 | 2-NO$_2$ | H | H | —(CH$_2$)$_4$— | CHCl$_2$ | |
| 1.499 | 2-NO$_2$ | H | H | —(CH$_2$)$_4$— | CHFCl | |
| 1.500 | 2-NO$_2$ | H | H | —(CH$_2$)$_4$— | CF$_2$CF$_3$ | |
| 1.501 | 2-NO$_2$ | H | H | —(CH$_2$)$_4$— | C$_3$F$_7$(n) | |
| 1.502 | 2-NO$_2$ | H | H | —(CH$_2$)$_4$— | CCl$_2$CF$_3$ | |
| 1.503 | 2-NO$_2$ | H | H | —(CH$_2$)$_4$— | SCH$_3$ | |
| 1.504 | 2-NO$_2$ | H | H | —(CH$_2$)$_4$— | SOCH$_3$ | |
| 1.505 | 2-NO$_2$ | H | H | —(CH$_2$)$_4$— | SO$_2$CH$_3$ | |
| 1.506 | 2-NO$_2$ | H | H | —C(CH$_3$)$_2$—(CH$_2$)$_3$— | Cl | |
| 1.507 | 2-NO$_2$ | H | H | —C(CH$_3$)$_2$—(CH$_2$)$_3$— | CF$_3$ | |
| 1.508 | 2-NO$_2$ | H | H | —C(CH$_3$)$_2$—(CH$_2$)$_3$— | CF$_2$Cl | |
| 1.509 | 2-NO$_2$ | H | H | —C(CH$_3$)$_2$—(CH$_2$)$_3$— | CHF$_2$ | |
| 1.510 | 2-NO$_2$ | H | H | —C(CH$_3$)$_2$—(CH$_2$)$_3$— | CF$_2$CF$_3$ | |
| 1.511 | 2-NO$_2$ | H | H | —CH$_2$—CHCH$_3$—(CH$_2$)$_2$— | Cl | |
| 1.512 | 2-NO$_2$ | H | H | —CH$_2$—CHCH$_3$—(CH$_2$)$_2$— | CF$_3$ | m.p. 147–148° C. |

TABLE 1-continued

Compounds of formula:

$$R^2, R^1, R^3, R^4, R^5, R^6, CONH_2 \quad (I)$$

| | | | | | | |
|---|---|---|---|---|---|---|
| 1.513 | 2-NO$_2$ | H | H | —(CH$_2$)$_3$—CHCH$_3$— | Cl | |
| 1.514 | 2-NO$_2$ | H | H | —(CH$_2$)$_3$—CHCH$_3$— | CF$_3$ | |
| 1.515 | 2-NO$_2$ | H | H | —(CH$_2$)$_2$—CHCH$_3$—CH$_2$— | Cl | |
| 1.516 | 2-NO$_2$ | H | H | —(CH$_2$)$_2$—CHCH$_3$—CH$_2$— | OCH$_3$ | |
| 1.517 | 2-NO$_2$ | H | H | —(CH$_2$)$_2$—CHCH$_3$—CH$_2$— | CF$_3$ | m.p. 184° C. (decomp.) |
| 1.518 | 2-NO$_2$ | H | H | —(CH$_2$)$_2$—CHCH$_3$—CH$_2$— | CF$_2$Cl | |
| 1.519 | 2-NO$_2$ | H | H | —(CH$_2$)$_2$—CHCH$_3$—CH$_2$— | CHCl$_2$ | |
| 1.520 | 2-NO$_2$ | H | H | —(CH$_2$)$_2$—C(CH$_3$)$_2$—CH$_2$— | Cl | |
| 1.521 | 2-NO$_2$ | H | H | —(CH$_2$)$_2$—C(CH$_3$)$_2$—CH$_3$— | CF$_3$ | |
| 1.522 | 2-NO$_2$ | H | H | —CH=CCH$_3$—CH$_2$—C(CH$_3$)$_2$— | Cl | |
| 1.523 | 2-NO$_2$ | H | H | —CH=CCH$_3$—CH$_2$—C(CH$_3$)$_2$— | CF$_3$ | |
| 1.524 | 2-NO$_2$ | H | H | —CH$_2$—CH(OCH$_3$)—(CH$_2$)$_2$ | Cl | |
| 1.525 | 2-NO$_2$ | H | H | —CH$_2$—CH(OCH$_3$)—(CH$_2$)$_2$ | CF$_3$ | |
| 1.526 | 2-NO$_2$ | H | H | —(CH$_2$)$_2$—S—CH$_2$— | Cl | |
| 1.527 | 2-NO$_2$ | H | H | —(CH$_2$)$_2$—S—CH$_2$— | CF$_3$ | |
| 1.528 | 2-NO$_2$ | H | H | —(CH$_2$)$_2$—O—CH$_2$— | Cl | |
| 1.529 | 2-NO$_2$ | H | H | —(CH$_2$)$_2$—NCH$_3$—CH$_2$— | CF$_3$ | |
| 1.530 | 2-NO$_2$ | H | H | —O—(CH$_2$)$_2$— | CF$_3$ | |
| 1.531 | 2-NO$_2$ | H | H | —O—(CH$_2$)$_3$— | CF$_3$ | |
| 1.532 | 2-NO$_2$ | H | H | —CH(COOC$_2$H$_5$)—(CH$_2$)$_3$ | Cl | |
| 1.533 | 2-NO$_2$ | H | H | —CH(COOC$_2$H$_5$)—(CH$_2$)$_3$ | CF$_3$ | |
| 1.534 | 2-NO$_2$ | H | H | —CHCH$_3$—CH$_2$—C(CH$_3$)$_2$—CH$_2$— | Cl | |
| 1.535 | 2-NO$_2$ | H | H | —CHCH$_3$—CH$_2$—C(CH$_3$)$_2$—CH$_2$— | CF$_3$ | |
| 1.536 | 2-NO$_2$ | H | H | —CHCH$_3$—CH$_2$—C(CH$_3$)$_2$—CH$_2$— | CF$_2$CF$_3$ | |
| 1.537 | 2-NO$_2$ | H | H | —(CH$_2$)$_5$— | Cl | |
| 1.538 | 2-NO$_2$ | H | H | —(CH$_2$)$_5$— | CF$_3$ | m.p. 156–158° C. |
| 1.539 | 2-NO$_2$ | H | H | —CHCH$_3$—(CH$_2$)$_4$— | Cl | |
| 1.540 | 2-NO$_2$ | H | H | —CHCH$_3$—(CH$_2$)$_4$— | CF$_3$ | |
| 1.541 | 2-NO$_2$ | H | H | —C(CH$_3$)$_2$—(CH$_2$)$_4$— | Cl | |
| 1.542 | 2-NO$_2$ | H | H | —C(CH$_3$)$_2$—(CH$_2$)$_4$— | CF$_3$ | |
| 1.543 | 2-NO$_2$ | H | H | —(CH$_2$)$_6$— | Cl | |
| 1.544 | 2-NO$_2$ | H | H | —(CH$_2$)$_6$— | CF$_3$ | m.p. 154–156° C. |
| 1.545 | 2-NO$_2$ | 6-CH$_3$ | H | —(CH$_2$)$_3$— | CF$_3$ | m.p. 167–168° C. |
| 1.546 | 2-NO$_2$ | 6-CH$_3$ | H | —(CH$_2$)$_3$— | Cl | |
| 1.547 | 2-NO$_2$ | 6-CH$_3$ | H | —(CH$_2$)$_3$— | OCH$_3$ | |
| 1.548 | 2-NO$_2$ | 6-CH$_3$ | H | —(CH$_2$)$_3$— | CF$_2$Cl | m.p. 177–178° C. |
| 1.549 | 2-NO$_2$ | 6-CH$_3$ | H | —(CH$_2$)$_3$— | CF$_2$CF$_3$ | |
| 1.550 | 2-NO$_2$ | 6-CH$_3$ | H | —(CH$_2$)$_3$— | CHCl$_2$ | |
| 1.551 | 2-NO$_2$ | 6-CH$_3$ | H | —CHCH$_3$—CH$_2$—CH$_2$— | Cl | |
| 1.552 | 2-NO$_2$ | 6-CH$_3$ | H | —CHCH$_3$—CH$_2$—CH$_2$ | CF$_3$ | |
| 1.553 | 2-NO$_2$ | 6-CH$_3$ | H | —CHCH$_3$—CH$_2$—CH$_2$ | CF$_2$Cl | |
| 1.554 | 2-NO$_2$ | 6-CH$_3$ | H | —C(CH$_3$)$_2$—CH$_2$—CH$_2$— | Cl | |
| 1.555 | 2-NO$_2$ | 6-CH$_3$ | H | —C(CH$_3$)$_2$—CH$_2$—CH$_2$— | CF$_3$ | |
| 1.556 | 2-NO$_2$ | 6-CH$_3$ | H | —C(CH$_3$)$_2$—CH$_2$—CH$_2$— | CF$_2$CF$_3$ | |
| 1.557 | 2-NO$_2$ | 6-CH$_3$ | H | —C(CH$_3$)$_2$—CH$_2$—CH$_2$— | CF$_2$Cl | |
| 1.558 | 2-NO$_2$ | 6-CH$_3$ | H | —C(CH$_3$)$_2$—CH$_2$—CH$_2$— | CHCl$_2$ | |
| 1.559 | 2-NO$_2$ | 6-CH$_3$ | H | —CH$_2$—CH$_2$—S— | Cl | |
| 1.560 | 2-NO$_2$ | 6-CH$_3$ | H | —CH$_2$—CH$_2$—S— | CF$_3$ | |
| 1.561 | 2-NO$_2$ | 6-CH$_3$ | H | —(CH$_2$)$_4$— | Cl | |
| 1.562 | 2-NO$_2$ | 6-CH$_3$ | H | —(CH$_2$)$_4$— | OCH$_3$ | |
| 1.563 | 2-NO$_2$ | 6-CH$_3$ | H | —(CH$_2$)$_4$— | CF$_3$ | m.p. 161–162° C. |
| 1.564 | 2-NO$_2$ | 6-CH$_3$ | H | —(CH$_2$)$_4$— | CF$_2$Cl | m.p. 175–177° C. |
| 1.565 | 2-NO$_2$ | 6-CH$_3$ | H | —(CH$_2$)$_4$— | CHF$_2$ | m.p. 148–149° C. |
| 1.566 | 2-NO$_2$ | 6-CH$_3$ | H | —(CH$_2$)$_4$— | CHFCl | |
| 1.567 | 2-NO$_2$ | 6-CH$_3$ | H | —(CH$_2$)$_4$— | CHCl$_2$ | |
| 1.568 | 2-NO$_2$ | 6-CH$_3$ | H | —(CH$_2$)$_4$— | CF$_2$CF$_3$ | |
| 1.569 | 2-NO$_2$ | 6-CH$_3$ | H | —(CH$_2$)$_4$— | C$_3$F$_7$(n) | |
| 1.570 | 2-NO$_2$ | 6-CH$_3$ | H | —(CH$_2$)$_4$— | CCl$_2$CF$_3$ | |
| 1.571 | 2-NO$_2$ | 6-CH$_3$ | H | —(CH$_2$)$_4$— | SCH$_3$ | |
| 1.572 | 2-NO$_2$ | 6-CH$_3$ | H | —(CH$_2$)$_4$ | SOCH$_3$ | |
| 1.573 | 2-NO$_2$ | 6-CH$_3$ | H | —(CH$_2$)$_4$ | SO$_2$CH$_3$ | |
| 1.574 | 2-NO$_2$ | 6-CH$_3$ | H | —C(CH$_3$)$_2$—(CH$_2$)$_3$— | Cl | |
| 1.575 | 2-NO$_2$ | 6-CH$_3$ | H | —C(CH$_3$)$_2$—(CH$_2$)$_3$— | CF$_3$ | |
| 1.576 | 2-NO$_2$ | 6-CH$_3$ | H | —CH$_2$—CHCH$_3$—(CH$_2$)$_2$— | Cl | |
| 1.577 | 2-NO$_2$ | 6-CH$_3$ | H | —CH$_2$—CHCH$_3$—(CH$_2$)$_2$— | CF$_3$ | m.p. 156–157° C. |
| 1.578 | 2-NO$_2$ | 6-CH$_3$ | H | —CH$_2$—CHCH$_3$—(CH$_2$)$_2$— | CF$_2$Cl | |
| 1.579 | 2-NO$_2$ | 6-CH$_3$ | H | —CH$_2$—CHCH$_3$—(CH$_2$)$_2$— | CHCl$_2$ | |
| 1.580 | 2-NO$_2$ | 6-CH$_3$ | H | —(CH$_2$)$_2$—NCH$_3$—CH$_2$— | CF$_3$ | |
| 1.581 | 2-NO$_2$ | 6-CH$_3$ | H | —(CH$_2$)$_5$— | Cl | |
| 1.582 | 2-NO$_2$ | 6-CH$_3$ | H | —(CH$_2$)$_5$— | CF$_3$ | m.p. 168–170° C. |
| 1.583 | 2-NO$_2$ | 6-CH$_3$ | H | —CH$_2$—CH$_2$—CH$_2$—O— | Cl | |
| 1.584 | 2-NO$_2$ | 6-CH$_3$ | H | —CH$_2$—CH$_2$—O— | CF$_3$ | |

TABLE 1-continued

Compounds of formula: (I)

| | R² | R³ | R¹ | (R ring) | R⁴/R⁵/R⁶ | m.p. |
|---|---|---|---|---|---|---|
| 1.585 | 2-Cl | H | H | —(CH₂)₃— | CF₃ | |
| 1.586 | 2-Cl | H | H | —(CH₂)₄— | CF₃ | |
| 1.587 | 2-Cl | 5-Cl | H | —(CH₂)₃— | Cl | |
| 1.588 | 2-Cl | 5-Cl | H | —(CH₂)₃— | CF₃ | m.p. 165–166° C. |
| 1.589 | 2-Cl | 5-Cl | H | —(CH₂)₃— | OCH₃ | |
| 1.590 | 2-Cl | 5-Cl | H | —(CH₂)₃— | CF₂Cl | |
| 1.591 | 2-Cl | 5-Cl | H | —(CH₂)₃— | CF₂CF₃ | |
| 1.592 | 2-Cl | 5-Cl | H | —(CH₂)₃— | CHCl₂ | |
| 1.593 | 2-Cl | 5-Cl | H | —C(CH₃)₂—CH₂—CH₂— | Cl | |
| 1.594 | 2-Cl | 5-Cl | H | —C(CH₃)₂—CH₂—CH₂— | OCH₃ | |
| 1.595 | 2-Cl | 5-Cl | H | —C(CH₃)₂—CH₂—CH₂— | CF₃ | |
| 1.596 | 2-Cl | 5-Cl | H | —C(CH₃)₂—CH₂—CH₂— | CF₂Cl | |
| 1.597 | 2-Cl | 5-Cl | H | —C(CH₃)₂—CH₂—CH₂— | CHCl₂ | |
| 1.598 | 2-Cl | 5-Cl | H | —C(CH₃)₂—CH₂—CH₂— | CF₂CF₃ | |
| 1.599 | 2-Cl | 5-Cl | H | —CH₂—CH₂—S— | Cl | |
| 1.600 | 2-Cl | 5-Cl | H | —CH₂—CH₂—S— | CF₃ | |
| 1.601 | 2-Cl | 5-Cl | H | —(CH₂)₄— | Cl | m.p. 168–169° C. |
| 1.602 | 2-Cl | 5-Cl | H | —(CH₂)₄— | OCH₃ | |
| 1.603 | 2-Cl | 5-Cl | H | —(CH₂)₄— | SCH₃ | |
| 1.604 | 2-Cl | 5-Cl | H | —(CH₂)₄— | SOCH₃ | |
| 1.605 | 2-Cl | 5-Cl | H | —(CH₂)₄— | SO₂CH₃ | |
| 1.606 | 2-Cl | 5-Cl | H | —(CH₂)₄— | CF₃ | m.p. 171–172° C. |
| 1.607 | 2-Cl | 5-Cl | H | —(CH₂)₄— | CF₂Cl | |
| 1.608 | 2-Cl | 5-Cl | H | —(CH₂)₄— | CHF₂ | |
| 1.609 | 2-Cl | 5-Cl | H | —(CH₂)₄— | CHCl₂ | |
| 1.610 | 2-Cl | 5-Cl | H | —(CH₂)₄— | CHFCl | |
| 1.611 | 2-Cl | 5-Cl | H | —(CH₂)₄— | CF₂CF₃ | |
| 1.612 | 2-Cl | 5-Cl | H | —(CH₂)₄— | C₃F₇n | |
| 1.613 | 2-Cl | 5-Cl | H | —C(CH₃)₂—(CH₂)₃— | Cl | |
| 1.614 | 2-Cl | 5-Cl | H | —C(CH₃)₂—(CH₂)₃— | OCH₃ | |
| 1.615 | 2-Cl | 5-Cl | H | —C(CH₃)₂—(CH₂)₃— | CF₃ | |
| 1.616 | 2-Cl | 5-Cl | H | —C(CH₃)₂—(CH₂)₃— | CF₂Cl | |
| 1.617 | 2-Cl | 5-Cl | H | —(CH₂)₅— | Cl | |
| 1.618 | 2-Cl | 5-Cl | H | —(CH₂)₅— | OCH₃ | |
| 1.619 | 2-Cl | 5-Cl | H | —(CH₂)₅— | CF₃ | m.p. 145–146° C. |
| 1.620 | 2-Cl | 5-Cl | H | —(CH₂)₅— | CF₂Cl | |
| 1.621 | 2-Cl | 5-Cl | H | —(CH₂)₆— | Cl | |
| 1.622 | 2-Cl | 5-Cl | H | —(CH₂)₆— | OCH₃ | |
| 1.623 | 2-Cl | 5-Cl | H | —(CH₂)₆— | CF₃ | m.p. 152–153° C. |
| 1.624 | 2-Cl | 5-Cl | H | —(CH₂)₆— | CF₂Cl | |
| 1.625 | 2-Cl | 6-Cl | H | —(CH₂)₃— | Cl | |
| 1.626 | 2-Cl | 6-Cl | H | —(CH₂)₃— | OCH₃ | |
| 1.627 | 2-Cl | 6-Cl | H | —(CH₂)₂— | CF₃ | m.p. 185–186° C. |
| 1.628 | 2-Cl | 6-Cl | H | —(CH₂)₃— | CF₂Cl | |
| 1.629 | 2-Cl | 6-Cl | H | —(CH₂)₃— | CHF₂ | m.p. 182–183° C. |
| 1.630 | 2-Cl | 6-Cl | H | —(CH₂)₃— | CF₂CF₃ | |
| 1.631 | 2-Cl | 6-Cl | H | —(CH₂)₄— | Cl | |
| 1.632 | 2-Cl | 6-Cl | H | —(CH₂)₄— | OCH₃ | |
| 1.633 | 2-Cl | 6-Cl | H | —(CH₂)₄— | CF₃ | m.p. 179–180° C. |
| 1.634 | 2-Cl | 6-Cl | H | —(CH₂)₄— | CF₂Cl | |
| 1.635 | 2-Cl | 6-Cl | H | —(CH₂)₄— | CHCl₂ | |
| 1.636 | 2-Cl | 6-Cl | H | —(CH₂)₄— | CHF₂ | |
| 1.637 | 2-Cl | 6-Cl | H | —CH₂—CH₂—CHCH₃—CH₂— | CF₃ | |
| 1.638 | 2-Cl | 6-Cl | H | —CH₂—CH₂—CHCH₃—CH₂— | CF₂Cl | |
| 1.639 | 2-Cl | 6-Cl | H | —CH₂—CH₂—CHCH₃—CH₂— | CHF₃ | |
| 1.640 | 2-Cl | 6-Cl | H | —(CH₂)₅— | CF₃ | |
| 1.641 | 2-Cl | 6-CH₃ | H | —(CH₂)₃— | Cl | |
| 1.642 | 2-Cl | 6-CH₃ | H | —(CH₂)₃— | CF₃ | m.p. 165–167° C. |
| 1.643 | 2-Cl | 6-CH₃ | H | —(CH₂)₃— | CF₂Cl | m.p. 182–183° C. |
| 1.644 | 2-Cl | 6-CH₃ | H | —(CH₂)₃— | CHF₂ | m.p. 173–174° C. |
| 1.645 | 2-Cl | 6-CH₃ | H | —(CH₂)₄— | Cl | |
| 1.646 | 2-Cl | 6-CH₃ | H | —(CH₂)₄— | CF₃ | m.p. 170–172° C. |
| 1.647 | 2-Cl | 6-CH₃ | H | —(CH₂)₄— | CF₂Cl | m.p. 185–186° C. |
| 1.648 | 2-Cl | 6-CH₃ | H | —(CH₂)₄— | CHF₂ | m.p. 167–168° C. |
| 1.649 | 2-Cl | 6-CH₃ | H | —(CH₂)₅— | CF₃ | |
| 1.650 | 2-Cl | 6-CH₃ | H | —(CH₂)₆— | CF₃ | |
| 1.651 | 2-Br | H | H | —(CH₂)₃— | Cl | |
| 1.652 | 2-Br | H | H | —(CH₂)₃— | CF₃ | |
| 1.653 | 2-Br | H | H | —(CH₂)₄— | Cl | |
| 1.654 | 2-Br | H | H | —(CH₂)₄— | CF₃ | |
| 1.655 | 2-Br | H | H | —(CH₂)₄— | CF₂Cl | |
| 1.656 | 2-CF₃ | H | H | —(CH₂)₃— | Cl | |
| 1.657 | 2-CF₃ | H | H | —(CH₂)₃— | CF₃ | |

TABLE 1-continued

Compounds of formula:

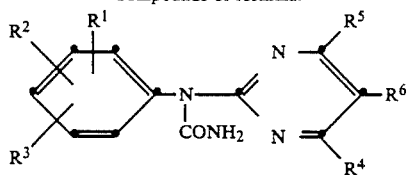
(I)

| Comp. No | R¹ | R² | R³ | R⁴ | | R⁶ | Phys. data |
|---|---|---|---|---|---|---|---|
| 1.658 | 2-CF₃ | H | H | —(CH₂)₃— | | CF₂Cl | |
| 1.659 | 2-CF₃ | 6-Cl | H | —(CH₂)₃— | | CF₃ | |
| 1.660 | 2-CF₃ | 6-Cl | H | —(CH₂)₄— | | CF₃ | |
| 1.661 | 2-OCH₃ | H | H | —(CH₂)₃— | | Cl | |
| 1.662 | 2-OCH₃ | H | H | —(CH₂)₃— | | CF₃ | |
| 1.663 | 2-OCH₃ | H | H | —(CH₂)₄— | | Cl | |
| 1.664 | 2-OCH₃ | H | H | —(CH₂)₄— | | CF₃ | |
| 1.665 | 2-OCH₃ | 5-Cl | H | —(CH₂)₃— | | Cl | |
| 1.666 | 2-OCH₃ | 5-Cl | H | —(CH₂)₃— | | CF₃ | |
| 1.667 | 2-OCH₃ | 5-Cl | H | —(CH₂)₄— | | Cl | |
| 1.668 | 2-OCH₃ | 5-Cl | H | —(CH₂)₄— | | CF₃ | |
| 1.669 | 2-OCHF₂ | H | H | —(CH₂)₃— | | Cl | |
| 1.670 | 2-OCHF₂ | H | H | —(CH₂)₃— | | CF₃ | |
| 1.671 | 2-OCHF₂ | H | H | —(CH₂)₄— | | Cl | |
| 1.672 | 2-OCHF₂ | H | H | —(CH₂)₄— | | CF₃ | m.p. 134–135° C. |
| 1.673 | 2-OCHF₂ | 5-Cl | H | —(CH₂)₃— | | Cl | |
| 1.674 | 2-OCHF₂ | 5-Cl | H | —(CH₂)₃— | | CF₃ | |
| 1.675 | 2-OCHF₂ | 5-Cl | H | —(CH₂)₄— | | Cl | |
| 1.676 | 2-OCHF₂ | 5-Cl | H | —(CH₂)₄— | | CF₃ | |
| 1.677 | 2-OCF₃ | H | H | —(CH₂)₃— | | Cl | |
| 1.678 | 2-OCF₃ | H | H | —(CH₂)₃— | | CF₃ | |
| 1.679 | 2-OCF₃ | H | H | —(CH₂)₄— | | Cl | |
| 1.680 | 2-OCF₃ | H | H | —(CH₂)₄— | | CF₃ | |
| 1.681 | 2-OCF₃ | 5-Cl | H | —(CH₂)₃— | | Cl | |
| 1.682 | 2-OCF₃ | 5-Cl | H | —(CH₂)₃— | | CF₃ | |
| 1.683 | 2-OCF₃ | 5-Cl | H | —(CH₂)₄— | | CF₃ | |
| 1.684 | 2-CH₃ | 5-Cl | H | —(CH₂)₃— | | Cl | |
| 1.685 | 2-CH₃ | 5-Cl | H | —(CH₂)₃— | | CF₃ | |
| 1.686 | 2-CH₃ | 5-Cl | H | —(CH₂)₄— | | Cl | |
| 1.687 | 2-CH₃ | 5-Cl | H | —(CH₂)₄— | | CF₃ | |
| 1.688 | 2-CN | H | H | —(CH₂)₃— | | CF₃ | |
| 1.689 | 2-CN | H | H | —(CH₂)₄— | | CF₃ | |
| 1.690 | 2-COOCH₃ | H | H | —(CH₂)₃— | | CF₃ | |
| 1.691 | 2-COOCH₃ | H | H | —(CH₂)₄— | | CF₃ | |
| 1.692 | 2-CH₃ | 6-CH₃ | H | —(CH₂)₄— | | Cl | |
| 1.693 | 2-CH₃ | 6-CH₃ | H | —(CH₂)₄— | | CF₃ | |
| 1.694 | 2-CH₃ | 6-CH₃ | H | —(CH₂)₄— | | CF₃ | |
| 1.695 | 2-CH₃ | 6-C₂H₅ | H | —(CH₂)₃— | | CF₃ | |
| 1.696 | 2-CH₃ | 6-C₂H₅ | H | —(CH₂)₄— | | CF₃ | |
| 1.697 | 2-NO₂ | H | H | —(CH₂)₃— | | CH₃ | |
| 1.698 | 2-NO₂ | H | H | —(CH₂)₄— | | CH₃ | |
| 1.699 | 2-NO₂ | 6-CH₃ | H | —(CH₂)₃— | | CH₃ | |
| 1.700 | 2-NO₂ | 6-CH₃ | H | —(CH₂)₄— | | CH₃ | |

| Comp. No | R¹ | R² | R³ | R⁴ | R⁵ | R⁶ | Phys. data |
|---|---|---|---|---|---|---|---|
| 1.701 | 2-SCH₃ | H | H | CH₃ | CF₃ | CH₃ | |
| 1.702 | 2-SOCH₃ | H | H | CH₃ | CF₃ | CH₃ | |
| 1.703 | 2-SCHF₂ | H | H | CH₃ | CF₃ | CH₃ | |
| 1.704 | 2-SOCHF₂ | H | H | CH₃ | CF₃ | CH₃ | |
| 1.705 | 2-CHF₂ | H | H | C₂H₅ | CF₃ | CH₃ | |
| 1.706 | 2-CH₂F | H | H | CH₃ | CF₃ | CH₃ | |
| 1.707 | 2-CF₂CH₃ | H | H | CH₃ | CF₃ | CH₃ | |
| 1.708 | 2-CH₂CH₂CF₃ | H | H | CH₃ | CF₃ | CH₃ | |
| 1.709 | 2-CHClCHClCF₃ | H | H | CH₃ | CF₃ | CH₃ | |
| 1.710 | 2-OCF₂CHF₂ | H | H | CH₃ | CF₃ | CH₃ | |
| 1.711 | 2-OCF₂CHF₂ | 5-Cl | H | CH₃ | CF₃ | CH₃ | |
| 1.712 | 2-SCH₃ | 5-Cl | H | CH₃ | CF₃ | CH₃ | |
| 1.713 | 2-SO₂CH₃ | 5-Cl | H | CH₃ | CF₃ | CH₃ | |
| 1.714 | 2-SCHF₂ | 5-Cl | H | CH₃ | CF₃ | CH₃ | |
| 1.715 | 2-SO₂CHF₂ | 5-Cl | H | CH₃ | CF₃ | CH₃ | |
| 1.716 | 2-CF₂CF₃ | H | H | C₂H₅ | CF₃ | CH₃ | |
| 1.717 | 2-CF₂CF₃ | H | H | CH₃ | CF₃ | Cl | |
| 1.718 | 2-OCH₂CH₂Cl | H | H | CH₃ | CF₃ | CH₃ | |
| 1.719 | 2-OCH₂CH₂Cl | 5-Cl | H | C₂H₅ | CF₃ | CH₃ | |
| 1.720 | 2-COOCH₃ | 6-Cl | H | CH₃ | CF₃ | CH₃ | |
| 1.721 | 2-COOCH₃ | 6-Cl | H | C₂H₅ | CF₃ | CH₃ | |
| 1.722 | 2-COOC₂H₅ | 6-Cl | H | CH₃ | CF₃ | SCH₃ | |
| 1.723 | 2-COOCH₃ | 6-Cl | H | CH₃ | Cl | SCH₃ | |
| 1.724 | 2-COOCH₃ | 6-Cl | H | CH₃ | Br | SCH₃ | |
| 1.725 | 2-COOCH₃ | 6-CH₃ | H | CH₃ | CF₃ | CH₃ | |
| 1.726 | 2-COOCH₃ | 6-CH₃ | H | CF₃ | Cl | CH₃ | |
| 1.727 | 2-COOC₃H₇(n) | 6-CH₃ | H | CH₃ | CF₃ | CH₃ | |
| 1.728 | 2-NO₂ | H | H | CH₃ | Br | Cl | |

TABLE 1-continued

Compounds of formula (I):

| Comp. No | R¹ | R² | R³ | R⁵ | R⁶ | R⁴ | Phys. data |
|---|---|---|---|---|---|---|---|
| 1.729 | 2-NO$_2$ | 6-CH$_3$ | H | CF$_3$ | F | CH$_3$ | |
| 1.730 | 2-NO$_2$ | 6-CH$_3$ | H | CF$_3$ | Br | CH$_3$ | |
| 1.731 | 2-NO$_2$ | 6-CH$_3$ | H | CH$_3$ | F | CH$_3$ | |
| 1.732 | 2-NO$_2$ | 6-CH$_3$ | H | CH$_3$ | Br | CH$_3$ | |
| 1.733 | 2-NO$_2$ | 6-CH$_3$ | H | CH$_3$ | CF$_3$ | Cyclopentyl | |
| 1.734 | 2-NO$_2$ | 6-CH$_3$ | H | CH$_3$ | CF$_3$ | Cyclopropyl | |
| 1.735 | 2-NO$_2$ | H | H | CH$_3$ | CF$_3$ | Cyclohexyl | |
| 1.736 | 2-NO$_2$ | H | H | C$_2$H$_5$ | CF$_3$ | Cyclopentyl | |
| 1.737 | 2-Cl | 5-Cl | H | CH$_3$ | CF$_3$ | Cyclopentyl | |
| 1.738 | 2-NO$_2$ | H | H | Cyclopentyl | CF$_3$ | CH$_3$ | |
| 1.739 | 2-NO$_2$ | 6-CH$_3$ | H | Cyclopentyl | CF$_3$ | CH$_3$ | |
| 1.740 | 2-Cl | 5-Cl | H | Cyclopentyl | CF$_3$ | CH$_3$ | |
| 1.741 | 2-Cl | 5-Cl | H | Cyclohexyl | CF$_3$ | CH$_3$ | |
| 1.742 | 2-Cl | 5-Cl | H | Cyclohexyl | Cl | CH$_3$ | |
| 1.743 | 2-NO$_2$ | H | H | Cyclohexyl | CF$_3$ | CH$_3$ | |
| 1.744 | 2-NO$_2$ | 6-CH$_3$ | H | Cyclohexyl | CF$_3$ | CH$_3$ | |
| 1.745 | 2-NO$_2$ | H | H | SCHF$_2$ | CF$_3$ | CH$_3$ | |
| 1.746 | 2-NO$_2$ | H | H | SCF$_3$ | CF$_3$ | CH$_3$ | |
| 1.747 | 2-NO$_2$ | 6-CH$_3$ | H | SCHF$_2$ | CF$_3$ | CH$_3$ | |
| 1.748 | 2-NO$_2$ | 6-CH$_3$ | H | SCHFCl | CF$_3$ | CH$_3$ | |
| 1.749 | 2-Cl | 5-Cl | H | SCHF$_2$ | CF$_3$ | CH$_3$ | |
| 1.750 | 2-Cl | 6-CH$_3$ | H | SCHF$_2$ | CF$_2$ | CH$_3$ | |
| 1.751 | 2-NO$_2$ | 6-CH$_3$ | H | Phenyl | CF$_3$ | CH$_3$ | |
| 1.752 | 2-NO$_2$ | 6-CH$_3$ | H | 4-Cl-Phenyl | CF$_3$ | CH$_3$ | |
| 1.753 | 2-NO$_2$ | 6-CH$_3$ | H | 2-Furyl | CF$_3$ | CH$_3$ | |
| 1.754 | 2-NO$_2$ | H | H | 2-Furyl | CF$_3$ | CH$_3$ | |
| 1.755 | 2-Cl | H | H | 2-Furyl | CF$_3$ | CH$_3$ | |

| Comp. No | R¹ | R² | R³ | —R$_5$—R$_6$— | R⁴ | Phys. data |
|---|---|---|---|---|---|---|
| 1.756 | 2-NO$_2$ | H | H | —CH$_2$CH$_2$COCH$_2$— | CF$_3$ | |
| 1.757 | 2-NO$_2$ | 6-CH$_3$ | H | —CH$_2$CH$_2$COCH$_2$— | CF$_3$ | |
| 1.758 | 2-NO$_2$ | H | H | —CH$_2$CH$_2$CHClCH$_2$— | CF$_3$ | |
| 1.759 | 2-NO$_2$ | 6-CH$_3$ | H | —CH$_2$CH$_2$CHClCH$_2$— | CF$_3$ | |
| 1.760 | 2-Cl | 5-Cl | H | —CH$_2$CH$_2$CHClCH$_2$— | CF$_3$ | |
| 1.761 | 2-Cl | 5-Cl | H | —CH$_2$CH$_2$COCH$_2$— | CF$_3$ | |
| 1.762 | 2-Cl | 6-Cl | H | —CH$_2$CH$_2$COCH$_2$— | CF$_3$ | |
| 1.763 | 2-OCF$_3$ | H | H | —CH$_2$CH$_2$COCH$_2$— | CF$_3$ | |
| 1.764 | 2-Cl | 6-CH$_3$ | H | —CH$_2$CH$_2$COCH$_2$— | CF$_3$ | |
| 1.765 | 2-SCH$_3$ | H | H | —CH$_2$CH$_2$CH$_2$CH$_2$— | CF$_3$ | |
| 1.766 | 2-SCH$_3$ | H | H | —CH$_2$—CH$_2$CH$_2$— | CF$_3$ | |
| 1.767 | 2-SC$_2$H$_5$ | H | H | —CH$_2$—CH$_2$—CH$_2$—CH$_2$— | CF$_3$ | |
| 1.768 | 2-SOC$_2$H$_5$ | H | H | —CH$_2$—CH$_2$—CH$_2$—CH$_2$— | CF$_3$ | |
| 1.769 | 2-SCHF$_2$ | H | H | —CH$_2$—CH$_2$—CH$_2$—CH$_2$— | CF$_3$ | |
| 1.770 | 2-SOCHF$_2$ | H | H | —CH$_2$—CH$_2$—CH$_2$—CH$_2$— | CF$_3$ | |
| 1.771 | 2-F | 6-Cl | H | —CH$_2$—CH$_2$—CH$_2$—CH$_2$— | CF$_3$ | m.p. 192–193° C. |
| 1.772 | 2-F | 6-Cl | H | —CH$_2$—CH$_2$—CH$_2$— | CF$_3$ | m.p. 176–177° C. |
| 1.773 | 2-SOCH$_3$ | 5-Cl | H | —CH$_2$—CH$_2$—CH$_2$—CH$_2$— | CF$_3$ | m.p. 164–165° C. |
| 1.774 | 2-SCH$_3$ | 5-Cl | H | —(CH$_2$)$_4$— | CF$_3$ | m.p. 151–152° C. |
| 1.775 | 2-NO$_2$ | 6-CH$_3$ | H | —(CH$_2$)$_6$— | CF$_3$ | m.p. 163–166° C. |
| 1.776 | 2-NO$_2$ | H | H | —(CH$_2$)$_4$— | CF$_2$Cl | m.p. 149–150° C. |
| 1.777 | 2-NO$_2$ | 6-CH$_3$ | H | —(CH$_2$)$_2$—CHCH$_3$—CH$_2$ | CF$_3$ | m.p. 164–165° C. |
| 1.778 | 2-F | H | H | —(CH$_2$)$_4$— | CF$_3$ | m.p. 170–171° C. |
| 1.779 | 2-Cl | 6-Cl | 3-CH$_3$ | —(CH$_2$)$_4$— | CF$_3$ | m.p. 168–170° C. |
| 1.780 | 2-Cl | 6-Cl | 3-CH$_3$ | —(CH$_2$)$_3$— | CF$_3$ | m.p. 166–167° C. |
| 1.781 | 2-NO$_2$ | 6-F | H | —(CH$_2$)$_4$— | CF$_3$ | m.p. 142–143° C. |
| 1.782 | 2-NO$_2$ | 6-F | H | —(CH$_2$)$_3$— | CF$_3$ | m.p. 143–144° C. |
| 1.783 | 2-OCH$_3$ | 6-Cl | H | —(CH$_2$)$_4$— | CF$_3$ | m.p. 164–165° C. |
| 1.784 | 2-OCH$_3$ | 6-Cl | H | —(CH$_3$)$_3$— | CF$_3$ | m.p. 154–157° C. |
| 1.785 | 2-F | 6-F | H | —(CH$_2$)$_4$— | CF$_3$ | m.p. 176–178° C. |
| 1.786 | 2-F | 6-F | H | —(CH$_2$)$_4$— | CF$_2$Cl | m.p. 169–171° C. |
| 1.787 | 2-F | 6-F | H | —(CH$_2$)$_4$— | CHF$_2$ | m.p. 172–174° C. |
| 1.788 | 2-CH$_3$ | 5-F | H | —(CH$_2$)$_4$— | CF$_3$ | m.p. 137–138° C. |
| 1.789 | 2-Br | 6-Br | H | —(CH$_2$)$_4$— | CF$_3$ | m.p. 186–187° C. |
| 1.790 | 2-CH$_3$ | 6-CH$_3$ | H | —(CH$_2$)$_4$— | CHF$_2$ | m.p. 166–168° C. |
| 1.791 | 2-NO$_2$ | H | H | —(CH$_2$)$_3$— | CF$_2$Cl | m.p. 156–157° C. |
| 1.792 | 2-NO$_2$ | H | H | —(CH$_2$)$_3$— | CHF$_2$ | m.p. 157–158° C. |
| 1.793 | 2-Cl | 5-Cl | H | —(CH$_2$)$_3$— | CHF$_2$ | m.p. 154–155° C. |
| 1.794 | 2-F | 6-Cl | H | —(CH$_2$)$_3$— | CHF$_2$ | m.p. 169–170° C. |
| 1.795 | 2-SCHF$_2$ | H | H | —(CH$_2$)$_3$— | CF$_3$ | m.p. 118–119° C. |
| 1.796 | 2-OCHF$_2$ | 6-CH$_3$ | H | —(CH$_2$)$_4$— | CF$_3$ | m.p. 125–126° C. |
| 1.797 | 2-F | 6-F | H | —(CH$_2$)$_3$— | CHF$_2$ | |

| Comp. No | R¹ | R² | R³ | R⁴ | R⁵ | R⁶ | Phys. data |
|---|---|---|---|---|---|---|---|

TABLE 1-continued

Compounds of formula: (I)

| | $R^1$ | $R^2$ | $R^3$ | $R^4$ | $R^5$ | $R^6$ | |
|---|---|---|---|---|---|---|---|
| 1.798 | 2-$NO_2$ | H | H | Cl | $CF_3$ | $CH_3$ | m.p. 170–171° C. |
| 1.799 | 2-$CH_3$ | 6-Cl | H | Cl | $CF_3$ | $CH_3$ | m.p. 175–176° C. |
| 1.800 | 2-$NO_2$ | H | H | $CF_3$ | $OC_2H_5$ | $CH_3$ | m.p. 179–180° C. |
| 1.801 | 2-$NO_2$ | H | H | $CF_3$ | Cl | $OCH_3$ | |

P. 2. Intermediates of formula II

P.2.1.
2-(2-methyl-6-nitrophenylamino)-5,6,7,8-tetrahydro-4-trifluoromethyl-quinazoline A mixture of 10.0 g of N-(2-methyl-6-nitrophenyl)-guanidine and 10.0 g of 2-trifluoroacetylcyclohexanone in 60 ml of tetrahydrofuran is stirred at room temperature for 90 minutes and is then heated at the boil for 3 hours. The solvent is removed by distillation, the residue is purified on silica gel with ethyl acetate/hexane (1:2), and the resulting product is recrystallised from hexane.

11.0 g of the title compound of formula

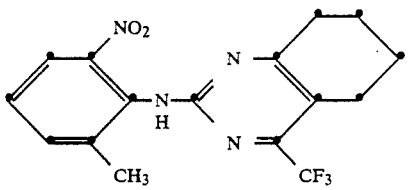

are isolated in the form of crystals having a melting point of 103°–104° C. (Comp. No. 2.563).

The compounds of Table 2 can be obtained in an analogous manner:

TABLE 2

Compounds of formula

| Comp. No. | $R^1$ | $R^2$ | $R^3$ | $R^4$ | $R^5$ | $R^6$ | Phys. data |
|---|---|---|---|---|---|---|---|
| 2.001 | 2-Cl | H | H | $CH_3$ | Cl | $CH_3$ | |
| 2.002 | 2-Cl | H | H | $CH_3$ | $CF_3$ | $CH_3$ | |
| 2.003 | 2-Cl | H | H | $C_2H_5$ | $CF_3$ | $CH_3$ | |
| 2.004 | 2-Cl | H | H | $OCH_3$ | $CF_3$ | $CH_3$ | |
| 2.005 | 2-Cl | H | H | $CH_3$ | $CF_3$ | $C_2H_5$ | |
| 2.006 | 2-F | H | H | $CH_3$ | $CF_3$ | $CH_3$ | |
| 2.007 | 2-F | H | H | $CH_3$ | Cl | $CH_3$ | |
| 2.008 | 2-F | H | H | $C_2H_5$ | $CF_3$ | $CH_3$ | |
| 2.009 | 2-F | H | H | $SCH_3$ | $CF_3$ | $CH_3$ | |
| 2.010 | 2-F | H | H | $OCH_3$ | $CH_3$ | CN | |
| 2.011 | 2-Br | H | H | $CH_3$ | Cl | $CH_3$ | |
| 2.012 | 2-Br | H | H | $CH_3$ | $CF_3$ | $CH_3$ | |
| 2.013 | 2-Br | H | H | $C_2H_5$ | $CF_3$ | $CH_3$ | |
| 2.014 | 2-Br | H | H | $C_2H_5$ | $CF_2Cl$ | $CH_3$ | |
| 2.015 | 2-Br | H | H | $C_2H_5$ | CHFCl | $CH_3$ | |
| 2.016 | 2-Br | H | H | $C_2H_5$ | $C_2F_5$ | $CH_3$ | |
| 2.017 | 2-Br | H | H | $C_2H_5$ | $CHCl_2$ | $CH_3$ | |
| 2.018 | 2-Br | H | H | $CH_3$ | $CF_2CF_3$ | $CH_3$ | |
| 2.019 | 2-Br | H | H | $OCH_3$ | $CF_3$ | $CH_3$ | |
| 2.020 | 2-Br | H | H | $SCH_3$ | $CF_3$ | $CH_3$ | |
| 2.021 | 2-Br | H | H | $SCH_3$ | $CH_3$ | $CH_3$ | |
| 2.022 | 2-Br | H | H | $SO_2CH_3$ | $CH_3$ | $CH_3$ | |
| 2.023 | 2-Br | H | H | Cyclopropyl | $CF_3$ | $CH_3$ | |
| 2.024 | 2-Br | H | H | $C_3H_7(i)$ | $CF_3$ | $CH_3$ | |
| 2.025 | 2-Br | H | H | $CH_3$ | Cl | $CH_2CH_2Cl$ | |
| 2.026 | 2-Br | H | H | $CH_3$ | Cl | $CH_2CH_2OCH_3$ | |
| 2.027 | 2-Br | H | H | $OCH_3$ | $CH_3$ | $CH_2CH_2OCH_3$ | |
| 2.028 | 2-J | H | H | $CH_3$ | Cl | $CH_3$ | |
| 2.029 | 2-J | H | H | $CH_3$ | $CF_3$ | $CH_3$ | |
| 2.030 | 2-J | H | H | $C_2H_5$ | $CF_3$ | $CH_3$ | |
| 2.031 | 2-J | H | H | $OCH_3$ | $CH_3$ | $CH_3$ | |
| 2.032 | 2-J | H | H | $CH_3$ | Cl | $C_2H_5$ | |
| 2.033 | 2-J | H | H | Cylopropyl | $CF_3$ | $CH_3$ | |
| 2.034 | 2-$CF_3$ | H | H | $CH_3$ | Cl | $CH_3$ | |

TABLE 2-continued

Compounds of formula

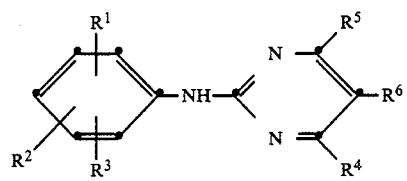

| | | R¹ | R² | R³ | R⁴ | R⁵ | R⁶ | |
|---|---|---|---|---|---|---|---|---|
| 2.035 | 2-CF$_3$ | H | H | OCH$_3$ | CH$_3$ | CH$_3$ | | |
| 2.036 | 2-CF$_3$ | H | H | SCH$_3$ | CH$_3$ | CH$_3$ | | |
| 2.037 | 2-CF$_3$ | H | H | SO$_2$CH$_3$ | CH$_3$ | CH$_3$ | | |
| 2.038 | 2-CF$_3$ | H | H | CH$_3$ | CF$_3$ | CH$_3$ | | |
| 2.039 | 2-CF$_3$ | H | H | C$_2$H$_5$ | CF$_3$ | CH$_3$ | | |
| 2.040 | 2-CF$_3$ | H | H | C$_2$H$_5$ | CF$_2$Cl | CH$_3$ | | |
| 2.041 | 2-CF$_3$ | H | H | C$_2$H$_5$ | CHCl$_2$ | CH$_3$ | | |
| 2.042 | 2-CF$_3$ | H | H | C$_2$H$_5$ | CF$_2$CF$_3$ | CH$_3$ | | |
| 2.043 | 2-CF$_3$ | H | H | OCH$_3$ | CH$_3$ | CN | | |
| 2.044 | 2-CF$_3$ | H | H | OCH$_3$ | CH$_3$ | NO$_2$ | | |
| 2.045 | 2-CF$_3$ | H | H | OCH$_3$ | CH$_3$ | Cl | | |
| 2.046 | 2-NO$_2$ | H | H | CH$_3$ | Cl | CH$_3$ | | |
| 2.047 | 2-NO$_2$ | H | H | CH$_3$ | CF$_3$ | CH$_3$ | | |
| 2.048 | 2-NO$_2$ | H | H | OCH$_3$ | CF$_3$ | CH$_3$ | | |
| 2.049 | 2-NO$_2$ | H | H | SCH$_3$ | CH$_3$ | CH$_3$ | | |
| 2.050 | 2-NO$_2$ | H | H | SOCH$_3$ | CH$_3$ | CH$_3$ | | |
| 2.051 | 2-NO$_2$ | H | H | SO$_2$CH$_3$ | CH$_3$ | CH$_3$ | | |
| 2.052 | 2-NO$_2$ | H | H | SCH$_3$ | CF$_3$ | CH$_3$ | | |
| 2.053 | 2-NO$_2$ | H | H | CH$_3$ | CF$_3$ | Phenyl | | |
| 2.054 | 2-NO$_2$ | H | H | OCH$_3$ | CF$_3$ | 4-Cl-Phenyl | | |
| 2.055 | 2-NO$_2$ | H | H | Cl | CF$_3$ | 4-Cl-Phenyl | | |
| 2.056 | 2-NO$_2$ | H | H | CH$_3$ | Cl | CH$_2$CH$_2$Cl | m.p. 145–146° C. | |
| 2.057 | 2-NO$_2$ | H | H | OCH$_3$ | CH$_3$ | CH$_2$CH$_2$OCH$_3$ | | |
| 2.058 | 2-NO$_2$ | H | H | C$_2$H$_5$ | CF$_3$ | CH$_3$ | m.p. 109–110° C. | |
| 2.059 | 2-NO$_2$ | H | H | C$_2$H$_5$ | CF$_2$Cl | CH$_3$ | | |
| 2.060 | 2-NO$_2$ | H | H | C$_2$H$_5$ | CHCl$_2$ | CH$_3$ | | |
| 2.061 | 2-NO$_2$ | H | H | C$_2$H$_5$ | CHFCl | CH$_3$ | | |
| 2.062 | 2-NO$_2$ | H | H | C$_2$H$_5$ | C$_2$F$_5$ | CH$_3$ | | |
| 2.063 | 2-NO$_2$ | H | H | C$_2$H$_5$ | C$_3$F$_7$(n) | CH$_3$ | | |
| 2.064 | 2-NO$_2$ | H | H | C$_2$H$_5$ | CCl$_2$CF$_3$ | CH$_3$ | | |
| 2.065 | 2-NO$_2$ | H | H | C$_3$H$_7$(n) | CF$_3$ | CH$_3$ | | |
| 2.066 | 2-NO$_2$ | H | H | C$_3$H$_7$(n) | CF$_3$ | C$_2$H$_5$ | | |
| 2.067 | 2-NO$_2$ | H | H | C$_3$H$_7$(i) | CF$_3$ | CH$_3$ | | |
| 2.068 | 2-NO$_2$ | H | H | Cyclopropyl | CF$_3$ | CH$_3$ | | |
| 2.069 | 2-NO$_2$ | H | H | CH$_3$ | OCHF$_2$ | CH$_3$ | | |
| 2.070 | 2-NO$_2$ | H | H | OCH$_3$ | CH$_3$ | NO$_2$ | | |
| 2.071 | 2-NO$_2$ | H | H | OCH$_3$ | CH$_3$ | Cl | | |
| 2.072 | 2-NO$_2$ | H | H | OCH$_3$ | CH$_3$ | CN | | |
| 2.073 | 2-NO$_2$ | H | H | CH$_3$ | Cl | CN | | |
| 2.074 | 2-NO$_2$ | H | H | CH$_3$ | Cl | NO$_2$ | | |
| 2.075 | 2-NO$_2$ | H | H | CH$_3$ | Cl | Cl | | |
| 2.076 | 2-NO$_2$ | H | H | SCH$_3$ | CH$_3$ | Cl | m.p. 104–105° C. | |
| 2.077 | 2-NO$_2$ | H | H | SO$_2$CH$_3$ | CH$_3$ | Cl | | |
| 2.078 | 2-NO$_2$ | H | H | OCH$_3$ | CH$_3$ | COOCH$_3$ | | |
| 2.079 | 2-NO$_2$ | H | H | CH$_3$ | CH$_3$ | COOCH$_3$ | | |
| 2.080 | 2-NO$_2$ | H | H | CH$_3$ | CF$_2$Cl | CH$_3$ | | |
| 2.081 | 2-OCH$_3$ | H | H | CH$_3$ | Cl | CH$_3$ | | |
| 2.082 | 2-OCH$_3$ | H | H | CH$_3$ | CF$_3$ | CH$_3$ | | |
| 2.083 | 2-OCH$_3$ | H | H | C$_2$H$_5$ | CF$_3$ | CH$_3$ | | |
| 2.084 | 2-OCH$_3$ | H | H | OCH$_3$ | CH$_3$ | CH$_3$ | | |
| 2.085 | 2-OCH$_3$ | H | H | OCH$_3$ | CF$_3$ | CH$_3$ | | |
| 2.086 | 2-OCF$_3$ | H | H | CH$_3$ | Cl | CH$_3$ | | |
| 2.087 | 2-OCF$_3$ | H | H | CH$_3$ | CF$_3$ | CH$_3$ | | |
| 2.088 | 2-OCF$_3$ | H | H | OCH$_3$ | CH$_3$ | CH$_3$ | | |
| 2.089 | 2-OCF$_3$ | H | H | SCH$_3$ | CH$_3$ | CH$_3$ | | |
| 2.090 | 2-OCF$_3$ | H | H | SO$_2$CH$_3$ | CH$_3$ | CH$_3$ | | |
| 2.091 | 2-OCF$_3$ | H | H | C$_2$H$_5$ | CF$_3$ | CH$_3$ | | |
| 2.092 | 2-OCF$_3$ | H | H | C$_2$H$_5$ | CF$_2$Cl | CH$_3$ | | |
| 2.093 | 2-OCF$_3$ | H | H | SCH$_3$ | CF$_3$ | CH$_3$ | | |
| 2.094 | 2-OCF$_3$ | H | H | OCH$_3$ | CF$_3$ | CH$_3$ | | |
| 2.095 | 2-OCF$_3$ | H | H | OC$_2$H$_5$ | CF$_3$ | CH$_3$ | | |
| 2.096 | 2-OCHF$_2$ | H | H | CH$_3$ | Cl | CH$_3$ | | |
| 2.097 | 2-OCHF$_2$ | H | H | CH$_3$ | Cl | C$_2$H$_5$ | | |
| 2.098 | 2-OCHF$_2$ | H | H | OCH$_3$ | CH$_3$ | C$_2$H$_5$ | | |
| 2.099 | 2-OCHF$_2$ | H | H | SCH$_3$ | CH$_3$ | CH$_3$ | | |
| 2.100 | 2-OCHF$_2$ | H | H | SO$_2$CH$_3$ | CH$_3$ | CH$_3$ | | |
| 2.101 | 2-OCHF$_2$ | H | H | CH$_3$ | CF$_3$ | CH$_3$ | | |
| 2.102 | 2-OCHF$_2$ | H | H | C$_2$H$_5$ | CF$_3$ | CH$_3$ | | |
| 2.103 | 2-OCHF$_2$ | H | H | C$_2$H$_5$ | CF$_2$Cl | CH$_3$ | | |
| 2.104 | 2-OCHF$_2$ | H | H | CH$_3$ | Cl | CH$_2$CH$_2$Cl | | |
| 2.105 | 2-OCHF$_2$ | H | H | OCH$_3$ | CH$_3$ | CH$_2$CH$_2$OCH$_3$ | | |
| 2.106 | 2-OCHF$_2$ | H | H | OC$_2$H$_5$ | CH$_3$ | CH$_2$CH$_2$OC$_2$H$_5$ | | |

TABLE 2-continued

Compounds of formula

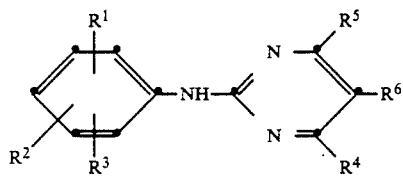

| | R¹ | R² | R³ | R⁴ | R⁵ | R⁶ |
|---|---|---|---|---|---|---|
| 2.107 | 2-OCHF$_2$ | H | H | Cyclopropyl | CF$_3$ | CH$_3$ |
| 2.108 | 2-OCHF$_2$ | H | H | C$_3$H$_7$(i) | CF$_3$ | CH$_3$ |
| 2.109 | 2-OC$_2$H$_5$ | H | H | CH$_3$ | Cl | CH$_3$ |
| 2.110 | 2-OC$_2$H$_5$ | H | H | CH$_3$ | CF$_3$ | CH$_3$ |
| 2.111 | 2-OC$_2$H$_5$ | H | H | OCH$_3$ | CH$_3$ | CH$_3$ |
| 2.112 | 2-OC$_2$H$_5$ | H | H | OCH$_3$ | CF$_3$ | CH$_3$ |
| 2.113 | 2-CN | H | H | CH$_3$ | CF$_3$ | CH$_3$ |
| 2.114 | 2-CN | H | H | C$_2$H$_5$ | CF$_3$ | CH$_3$ |
| 2.115 | 2-CN | H | H | OCH$_3$ | CH$_3$ | CH$_3$ |
| 2.116 | 2-CN | H | H | OCH$_3$ | CF$_3$ | CH$_3$ |
| 2.117 | 2-CN | H | H | SCH$_3$ | CF$_3$ | CH$_3$ |
| 2.118 | 2-CN | H | H | Cyclopropyl | CF$_3$ | CH$_3$ |
| 2.119 | 2-CN | H | H | OCH$_3$ | CH$_3$ | Cl |
| 2.120 | 2-COOCH$_3$ | H | H | CH$_3$ | CF$_3$ | CH$_3$ |
| 2.121 | 2-COOCH$_3$ | H | H | OCH$_3$ | CF$_3$ | CH$_3$ |
| 2.123 | 2-COOCH$_3$ | H | H | OCH$_3$ | CF$_3$ | Phenyl |
| 2.124 | 2-CON(CH$_3$)$_2$ | H | H | CH$_3$ | Cl | CH$_3$ |
| 2.125 | 2-CON(CH$_3$)$_2$ | H | H | CH$_3$ | CF$_3$ | CH$_3$ |
| 2.126 | 2-CON(CH$_3$)$_2$ | H | H | OCH$_3$ | CF$_3$ | CH$_3$ |
| 2.127 | 2-CON(CH$_3$)$_2$ | H | H | OCH$_3$ | CF$_3$ | C$_2$H$_5$ |
| 2.128 | 2-CH$_3$ | H | H | CH$_3$ | Cl | CH$_3$ |
| 2.129 | 2-CH$_3$ | H | H | CH$_3$ | CF$_3$ | CH$_3$ |
| 2.130 | 2-CH$_3$ | H | H | C$_2$H$_5$ | CF$_3$ | CH$_3$ |
| 2.131 | 2-CH$_3$ | H | H | CH$_3$ | CF$_2$Cl | CH$_3$ |
| 2.132 | 2-CH$_3$ | H | H | OCH$_3$ | CF$_3$ | CH$_3$ |
| 2.133 | 2-C$_2$H$_5$ | H | H | CH$_3$ | Cl | CH$_3$ |
| 2.134 | 2-C$_2$H$_5$ | H | H | CH$_3$ | CF$_3$ | CH$_3$ |
| 2.135 | 2-C$_2$H$_5$ | H | H | OCH$_3$ | CF$_3$ | CH$_3$ |
| 2.136 | 2-C$_2$H$_5$ | H | H | SCH$_3$ | CF$_3$ | CH$_3$ |
| 2.137 | 3-Cl | H | H | CH$_3$ | CF$_3$ | CH$_3$ |
| 2.138 | 3-Br | H | H | CH$_3$ | CF$_3$ | CH$_3$ |
| 2.139 | 3-CF$_3$ | H | H | C$_2$H$_5$ | CF$_3$ | CH$_3$ |
| 2.140 | 3-Cl | 5-Cl | H | CH$_3$ | Cl | CH$_3$ |
| 2.141 | 3-Cl | 5-Cl | H | CH$_3$ | CF$_3$ | CH$_3$ |
| 2.142 | 3-Cl | 5-Cl | H | C$_2$H$_5$ | CF$_3$ | CH$_3$ |
| 2.143 | 3-Cl | 5-Cl | H | OCH$_3$ | CF$_3$ | CH$_3$ |
| 2.144 | 2-Cl | 5-Cl | H | CH$_3$ | Cl | CH$_3$ |
| 2.145 | 2-Cl | 5-Cl | H | CH$_3$ | CF$_3$ | CH$_3$ |
| 2.146 | 2-Cl | 5-Cl | H | OCH$_3$ | CF$_3$ | CH$_3$ |
| 2.147 | 2-Cl | 5-Cl | H | SCH$_3$ | CH$_3$ | CH$_3$ |
| 2.148 | 2-Cl | 5-Cl | H | SOCH$_3$ | CH$_3$ | CH$_3$ |
| 2.149 | 2-Cl | 5-Cl | H | SO$_2$CH$_3$ | CH$_3$ | CH$_3$ |
| 2.150 | 2-Cl | 5-Cl | H | SC$_2$H$_5$ | CF$_3$ | CH$_3$ |
| 2.151 | 2-Cl | 5-Cl | H | SC$_3$H$_7$(i) | CF$_3$ | CH$_3$ |
| 2.152 | 2-Cl | 5-Cl | H | OC$_2$H$_5$ | CF$_3$ | CH$_3$ |
| 2.153 | 2-Cl | 5-Cl | H | SOC$_2$H$_5$ | CF$_3$ | CH$_3$ |
| 2.154 | 2-Cl | 5-Cl | H | OC$_3$H$_7$(i) | CF$_3$ | CH$_3$ |
| 2.155 | 2-Cl | 5-Cl | H | CH$_3$ | Cl | Phenyl |
| 2.156 | 2-Cl | 5-Cl | H | OCH$_3$ | CH$_3$ | Phenyl |
| 2.157 | 2-Cl | 5-Cl | H | CH$_3$ | Cl | CH$_2$CH$_2$Cl |
| 2.158 | 2-Cl | 5-Cl | H | OCH$_3$ | CH$_3$ | CH$_2$CH$_2$OCH$_3$ |
| 2.159 | 2-Cl | 5-Cl | H | C$_2$H$_5$ | CF$_3$ | CH$_3$ |
| 2.160 | 2-Cl | 5-Cl | H | CH$_3$ | CF$_2$Cl | CH$_3$ |
| 2.161 | 2-Cl | 5-Cl | H | CH$_3$ | C$_2$H$_5$ | CH$_3$ |
| 2.162 | 2-Cl | 5-Cl | H | CH$_3$ | C$_3$F$_7$(n) | CH$_3$ |
| 2.163 | 2-Cl | 5-Cl | H | C$_2$H$_5$ | CF$_2$Cl | CH$_3$ |
| 2.164 | 2-Cl | 5-Cl | H | C$_2$H$_5$ | CHF$_2$ | CH$_3$ |
| 2.165 | 2-Cl | 5-Cl | H | CH$_3$ | CCl$_2$CF$_3$ | CH$_3$ |
| 2.166 | 2-Cl | 5-Cl | H | C$_3$H$_7$(n) | CF$_3$ | CH$_3$ |
| 2.167 | 2-Cl | 5-Cl | H | C$_3$H$_7$(i) | CF$_3$ | CH$_3$ |
| 2.168 | 2-Cl | 5-Cl | H | Clyclopropyl | CF$_3$ | CH$_3$ |
| 2.169 | 2-Cl | 5-Cl | H | CH$_3$ | CF$_3$ | C$_2$H$_5$ |
| 2.170 | 2-Cl | 5-Cl | H | CH$_3$ | CF$_3$ | C$_3$H$_7$(i) |
| 2.171 | 2-Cl | 5-Cl | H | CH$_3$ | OCHF$_2$ | CH$_3$ |
| 2.172 | 2-Cl | 5-Cl | H | OCH$_3$ | CH$_3$ | NO$_2$ |
| 2.173 | 2-Cl | 5-Cl | H | OCH$_3$ | CH$_3$ | Cl |
| 2.174 | 2-Cl | 5-Cl | H | OCH$_3$ | CH$_3$ | CN |
| 2.175 | 2-Cl | 5-Cl | H | OC$_2$H$_5$ | CH$_3$ | CN |
| 2.176 | 2-Cl | 5-Cl | H | CH$_3$ | Cl | CN |
| 2.177 | 2-Cl | 5-Cl | H | CH$_3$ | Cl | NO$_2$ |
| 2.178 | 2-Cl | 5-Cl | H | CH$_3$ | Cl | Cl |
| 2.179 | 2-Cl | 5-Cl | H | C$_2$H$_5$ | Cl | Cl |

TABLE 2-continued

Compounds of formula

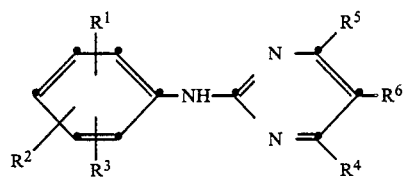

| | R1 | R2 | R3 | R4 | R5 | R6 | |
|---|---|---|---|---|---|---|---|
| 2.180 | 2-Cl | 5-Cl | H | C2H5 | Cl | Br | |
| 2.181 | 2-Cl | 5-Cl | H | OCH3 | CH3 | COOCH3 | |
| 2.182 | 2-Cl | 5-Cl | H | CH3 | CH3 | COOC2H5 | |
| 2.183 | 2-Cl | 6-Cl | H | CH3 | Cl | CH3 | |
| 2.184 | 2-Cl | 6-Cl | H | CH3 | CF3 | CH3 | |
| 2.185 | 2-Cl | 6-Cl | H | CH3 | CF3 | C2H5 | |
| 2.186 | 2-Cl | 6-Cl | H | OCH3 | CF3 | CH3 | |
| 2.187 | 2-Cl | 6-Cl | H | SCH3 | CF3 | CH3 | |
| 2.188 | 2-Cl | 6-Cl | H | CF3 | Cl | CH3 | m.p. 128–130° C. |
| 2.189 | 2-Cl | 6-Cl | H | SC4H9(n) | CF3 | CH3 | |
| 2.190 | 2-Cl | 6-Cl | H | SC2H5 | CH3 | CH3 | |
| 2.191 | 2-Cl | 6-Cl | H | SOC2H5 | CH3 | CH3 | |
| 2.192 | 2-Cl | 6-Cl | H | SO2C2H5 | CH3 | CH3 | |
| 2.193 | 2-Cl | 6-Cl | H | C2H5 | CF3 | CH3 | |
| 2.194 | 2-Cl | 6-Cl | H | C3H7(n) | CF3 | CH3 | |
| 2.195 | 2-Cl | 6-Cl | H | C4H9(n) | CF3 | CH3 | |
| 2.196 | 2-Cl | 6-Cl | H | Cyclopropyl | CF3 | CH3 | |
| 2.197 | 2-Cl | 6-Cl | H | C3H7(i) | CF3 | CH3 | m.p. 81–82° C. |
| 2.198 | 2-Cl | 6-Cl | H | CH3 | CF2Cl | CH3 | |
| 2.199 | 2-Cl | 6-Cl | H | CH3 | CHF2 | CH3 | |
| 2.200 | 2-Cl | 6-Cl | H | CH3 | CHCl2 | CH3 | |
| 2.201 | 2-Cl | 6-Cl | H | CH3 | CHFCl | CH3 | |
| 2.202 | 2-Cl | 6-Cl | H | CH3 | CCl2CF3 | CH3 | |
| 2.203 | 2-Cl | 6-Cl | H | CH3 | OCHF2 | CH3 | |
| 2.204 | 2-Cl | 6-Cl | H | OCH3 | CH3 | NO2 | |
| 2.205 | 2-Cl | 6-Cl | H | OCH3 | CF3 | NO2 | |
| 2.206 | 2-Cl | 6-Cl | H | OCH3 | CF3 | Cl | |
| 2.207 | 2-Cl | 6-Cl | H | OCH3 | CH3 | CN | |
| 2.208 | 2-Cl | 6-Cl | H | CH3 | Cl | CN | |
| 2.209 | 2-Cl | 6-Cl | H | CH3 | Cl | NO2 | |
| 2.210 | 2-Cl | 6-Cl | H | CH3 | Cl | Cl | |
| 2.211 | 2-Cl | 6-Cl | H | CH3 | Cl | Br | |
| 2.212 | 2-Cl | 6-Cl | H | OCH3 | CH3 | COOCH3 | |
| 2.213 | 2-Cl | 3-Cl | H | CH3 | Cl | CH3 | |
| 2.214 | 2-Cl | 3-Cl | H | CH3 | CF3 | CH3 | |
| 2.215 | 2-Cl | 3-Cl | H | C2H5 | CF3 | CH3 | |
| 2.216 | 2-Cl | 3-Cl | H | C2H5 | CF2Cl | CH3 | |
| 2.217 | 2-NO2 | 3-CH3 | H | CH3 | Cl | CH3 | |
| 2.218 | 2-NO2 | 3-CH3 | H | CH3 | CF3 | CH3 | |
| 2.219 | 2-NO2 | 3-CH3 | H | C2H5 | CF3 | CH3 | |
| 2.220 | 2-NO2 | 3-CH3 | H | C2H5 | CF2Cl | CH3 | |
| 2.221 | 2-NO2 | 3-Cl | H | CH3 | Cl | CH3 | |
| 2.222 | 2-NO2 | 3-Cl | H | CH3 | CF3 | CH3 | |
| 2.223 | 2-NO2 | 3-Cl | H | OCH3 | CH3 | CH3 | |
| 2.224 | 2-NO2 | 3-Cl | H | C2H5 | CF3 | CH3 | |
| 2.225 | 2-NO2 | 3-Cl | H | C2H5 | CF2Cl | CH3 | |
| 2.226 | 2-NO2 | 5-Cl | H | CH3 | Cl | CH3 | |
| 2.227 | 2-NO2 | 5-Cl | H | CH3 | CF3 | CH3 | |
| 2.228 | 2-NO2 | 5-Cl | H | C2H5 | CF3 | CH3 | |
| 2.229 | 2-NO2 | 5-Cl | H | CH3 | CF2Cl | CH3 | |
| 2.230 | 2-NO2 | 5-Cl | H | SCH3 | CH3 | CH3 | |
| 2.231 | 2-NO2 | 5-Cl | H | SOCH3 | CH3 | CH3 | |
| 2.232 | 2-NO2 | 5-Cl | H | SO2CH3 | CH3 | CH3 | |
| 2.233 | 2-NO2 | 5-Cl | H | CN | CH3 | CH3 | |
| 2.234 | 2-NO2 | 5-Cl | H | OCH3 | CF3 | CH3 | |
| 2.235 | 2-NO2 | 5-Cl | H | SCH3 | CF3 | CH3 | |
| 2.236 | 2-NO2 | 5-Cl | H | OC3H7(i) | CF3 | CH3 | |
| 2.237 | 2-NO2 | 5-Cl | H | SC2H5 | CF3 | CH3 | |
| 2.238 | 2-NO2 | 5-Cl | H | C3H7(i) | CF3 | CH3 | |
| 2.239 | 2-NO2 | 6-Cl | H | CH3 | Cl | CH3 | |
| 2.240 | 2-NO2 | 6-Cl | H | CH3 | CF3 | CH3 | |
| 2.241 | 2-NO2 | 6-Cl | H | OCH3 | CF3 | CH3 | |
| 2.242 | 2-NO2 | 6-Cl | H | SCH3 | CF3 | CH3 | |
| 2.243 | 2-NO2 | 6-Cl | H | SOCH3 | CF3 | CH3 | |
| 2.244 | 2-NO2 | 6-Cl | H | SO2CH3 | CF3 | CH3 | |
| 2.245 | 2-NO2 | 6-Cl | H | C2H5 | CF3 | CH3 | |
| 2.246 | 2-NO2 | 6-Cl | H | Cyclopropyl | CF3 | CH3 | |
| 2.247 | 2-NO2 | 6-Cl | H | C3H7(i) | CF3 | CH3 | |
| 2.248 | 2-NO2 | 6-Cl | H | CH3 | CF2Cl | CH3 | |
| 2.249 | 2-NO2 | 5-CH3 | H | CH3 | Cl | CH3 | |
| 2.250 | 2-NO2 | 5-CH3 | H | CH3 | CF3 | CH3 | |
| 2.251 | 2-NO2 | 5-CH3 | H | OCH3 | CF3 | CH3 | |

TABLE 2-continued

Compounds of formula

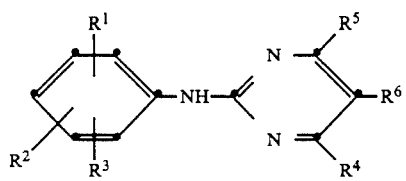

| | | | | | | | |
|---|---|---|---|---|---|---|---|
| 2.252 | 2-NO$_2$ | 5-CH$_3$ | H | CF$_3$ | Cl | CH$_3$ | |
| 2.253 | 2-NO$_2$ | 5-CH$_3$ | H | SCH$_3$ | CF$_3$ | CH$_3$ | |
| 2.254 | 2-NO$_2$ | 5-CH$_3$ | H | C$_2$H$_5$ | CF$_3$ | CH$_3$ | |
| 2.255 | 2-NO$_2$ | 5-CH$_3$ | H | C$_3$H$_7$(n) | CF$_3$ | CH$_3$ | |
| 2.256 | 2-NO$_2$ | 5-CH$_3$ | H | C$_3$H$_7$(i) | CF$_3$ | CH$_3$ | |
| 2.257 | 2-NO$_2$ | 5-CH$_3$ | H | Cyclopropyl | CF$_3$ | CH$_3$ | |
| 2.258 | 2-NO$_2$ | 5-CH$_3$ | H | CH$_3$ | CF$_2$Cl | CH$_3$ | |
| 2.259 | 2-NO$_2$ | 5-CH$_3$ | H | CH$_3$ | CHFCl | CH$_3$ | |
| 2.260 | 2-NO$_2$ | 5-CH$_3$ | H | OCH$_3$ | CH$_3$ | NO$_2$ | |
| 2.261 | 2-NO$_2$ | 5-CH$_3$ | H | OCH$_3$ | CH$_3$ | CN | |
| 2.262 | 2-NO$_2$ | 5-CH$_3$ | H | OCH$_3$ | CH$_3$ | Cl | |
| 2.263 | 2-NO$_2$ | 5-CH$_3$ | H | OCH$_3$ | CH$_3$ | COOCH$_3$ | |
| 2.264 | 2-NO$_2$ | 5-CH$_3$ | H | OC$_3$H$_7$(n) | CF$_3$ | CH$_3$ | |
| 2.265 | 2-NO$_2$ | 5-CH$_3$ | H | SC$_2$H$_5$ | CF$_3$ | CH$_3$ | |
| 2.266 | 2-NO$_2$ | 6-CH$_3$ | H | CH$_3$ | Cl | CH$_3$ | |
| 2.267 | 2-NO$_2$ | 6-CH$_3$ | H | OCH$_3$ | CH$_3$ | CH$_3$ | |
| 2.268 | 2-NO$_2$ | 6-CH$_3$ | H | SCH$_3$ | CH$_3$ | CH$_3$ | |
| 2.269 | 2-NO$_2$ | 6-CH$_3$ | H | SOCH$_3$ | CH$_3$ | CH$_3$ | |
| 2.270 | 2-NO$_2$ | 6-CH$_3$ | H | SO$_2$CH$_3$ | CH$_3$ | CH$_3$ | |
| 2.271 | 2-NO$_2$ | 6-CH$_3$ | H | CF$_3$ | Cl | CH$_3$ | |
| 2.272 | 2-NO$_2$ | 6-CH$_3$ | H | OCH$_3$ | CF$_3$ | CH$_3$ | |
| 2.273 | 2-NO$_2$ | 6-CH$_3$ | H | OC$_2$H$_5$ | CF$_3$ | CH$_3$ | |
| 2.274 | 2-NO$_2$ | 6-CH$_3$ | H | SCH$_3$ | CF$_3$ | CH$_3$ | |
| 2.275 | 2-NO$_2$ | 6-CH$_3$ | H | SOCH$_3$ | CF$_3$ | CH$_3$ | |
| 2.276 | 2-NO$_2$ | 6-CH$_3$ | H | SO$_2$CH$_3$ | CF$_3$ | CH$_3$ | |
| 2.277 | 2-NO$_2$ | 6-CH$_3$ | H | SC$_3$H$_7$(i) | CF$_3$ | CH$_3$ | |
| 2.278 | 2-NO$_2$ | 6-CH$_3$ | H | CF$_3$ | Cl | C$_2$H$_5$ | |
| 2.279 | 2-NO$_2$ | 6-CH$_3$ | H | OCH$_3$ | CF$_3$ | C$_2$H$_5$ | |
| 2.280 | 2-NO$_2$ | 6-CH$_3$ | H | SCH$_3$ | CF$_3$ | C$_2$H$_5$ | |
| 2.281 | 2-NO$_2$ | 6-CH$_3$ | H | CF$_3$ | Cl | C$_3$H$_7$(i) | |
| 2.282 | 2-NO$_2$ | 6-CH$_3$ | H | OCH$_3$ | CF$_3$ | C$_3$H$_7$(i) | |
| 2.283 | 2-NO$_2$ | 6-CH$_3$ | H | SC$_2$H$_5$ | CF$_3$ | C$_3$H$_7$(i) | |
| 2.284 | 2-NO$_2$ | 6-CH$_3$ | H | CH$_3$ | CF$_3$ | CH$_3$ | m.p. 134–135° C. |
| 2.285 | 2-NO$_2$ | 6-CH$_3$ | H | C$_2$H$_5$ | CF$_3$ | CH$_3$ | m.p. 112–113° C. |
| 2.286 | 2-NO$_2$ | 6-CH$_3$ | H | C$_3$H$_7$(n) | CF$_3$ | CH$_3$ | |
| 2.287 | 2-NO$_2$ | 6-CH$_3$ | H | C$_3$H$_7$(i) | CF$_3$ | CH$_3$ | |
| 2.288 | 2-NO$_2$ | 6-CH$_3$ | H | Cyclopropyl | CF$_3$ | CH$_3$ | |
| 2.289 | 2-NO$_2$ | 6-CH$_3$ | H | C$_4$H$_9$(n) | CF$_3$ | CH$_3$ | |
| 2.290 | 2-NO$_2$ | 6-CH$_3$ | H | CH$_3$ | CF$_2$Cl | CH$_3$ | |
| 2.291 | 2-NO$_2$ | 6-CH$_3$ | H | CH$_3$ | CHF$_2$ | CH$_3$ | |
| 2.292 | 2-NO$_2$ | 6-CH$_3$ | H | CH$_3$ | CHCl$_2$ | CH$_3$ | |
| 2.293 | 2-NO$_2$ | 6-CH$_3$ | H | CH$_3$ | CHFCl | CH$_3$ | |
| 2.294 | 2-NO$_2$ | 6-CH$_3$ | H | CH$_3$ | C$_2$F$_5$ | CH$_3$ | |
| 2.295 | 2-NO$_2$ | 6-CH$_3$ | H | CH$_3$ | C$_3$F$_7$(n) | CH$_3$ | |
| 2.296 | 2-NO$_2$ | 6-CH$_3$ | H | C$_2$H$_5$ | CF$_2$Cl | CH$_3$ | |
| 2.297 | 2-NO$_2$ | 6-CH$_3$ | H | C$_3$H$_7$(i) | CF$_2$Cl | CH$_3$ | |
| 2.298 | 2-NO$_2$ | 6-CH$_3$ | H | Cyclopropyl | CF$_2$Cl | CH$_3$ | |
| 2.299 | 2-NO$_2$ | 6-CH$_3$ | H | C$_2$H$_5$ | C$_2$F$_5$ | CH$_3$ | |
| 2.300 | 2-NO$_2$ | 6-CH$_3$ | H | C$_2$H$_5$ | CHCl$_2$ | CH$_3$ | |
| 2.301 | 2-NO$_2$ | 6-CH$_3$ | H | CH$_3$ | CCl$_2$CF$_3$ | CH$_3$ | |
| 2.302 | 2-NO$_2$ | 6-CH$_3$ | H | CH$_3$ | OCHF$_2$ | CH$_3$ | |
| 2.303 | 2-NO$_2$ | 6-CH$_3$ | H | CH$_3$ | Cl | CH$_2$CH$_2$Cl | |
| 2.304 | 2-NO$_2$ | 6-CH$_3$ | H | OCH$_3$ | CH$_3$ | CH$_2$CH$_2$OCH$_3$ | |
| 2.305 | 2-NO$_2$ | 6-CH$_3$ | H | SCH$_3$ | CH$_3$ | CH$_2$CH$_2$SCH$_3$ | |
| 2.306 | 2-NO$_2$ | 6-CH$_3$ | H | CN | CH$_3$ | CH$_3$ | |
| 2.307 | 2-NO$_2$ | 6-CH$_3$ | H | CH$_3$ | CF$_3$ | Phenyl | |
| 2.308 | 2-NO$_2$ | 6-CH$_3$ | H | CH$_3$ | Cl | Phenyl | |
| 2.309 | 2-NO$_2$ | 6-CH$_3$ | H | OCH$_3$ | CH$_3$ | NO$_2$ | |
| 2.310 | 2-NO$_2$ | 6-CH$_3$ | H | OCH$_3$ | CH$_3$ | Cl | |
| 2.311 | 2-NO$_2$ | 6-CH$_3$ | H | OCH$_3$ | CH$_3$ | CN | |
| 2.312 | 2-NO$_2$ | 6-CH$_3$ | H | CH$_3$ | Cl | CN | |
| 2.313 | 2-NO$_2$ | 6-CH$_3$ | H | CH$_3$ | Cl | NO$_2$ | |
| 2.314 | 2-NO$_2$ | 6-CH$_3$ | H | CH$_3$ | Cl | Cl | |
| 2.315 | 2-NO$_2$ | 6-CH$_3$ | H | SCH$_3$ | CH$_3$ | Cl | |
| 2.316 | 2-NO$_2$ | 6-CH$_3$ | H | Cl | OCH$_3$ | | |
| 2.317 | 2-NO$_2$ | 6-CH$_3$ | H | OCH$_3$ | CH$_3$ | COOC$_2$H$_5$ | |
| 2.318 | 2-NO$_2$ | 6-CH$_3$ | H | CH$_3$ | CH$_3$ | COOCH$_3$ | |
| 2.319 | 2-NO$_2$ | 5-F | H | CH$_3$ | Cl | CH$_3$ | |
| 2.320 | 2-NO$_2$ | 5-F | H | CH$_3$ | CF$_3$ | CH$_3$ | |
| 2.321 | 2-NO$_2$ | 5-F | H | C$_2$H$_5$ | CF$_3$ | CH$_3$ | |
| 2.322 | 2-NO$_2$ | 6-F | H | CH$_3$ | Cl | CH$_3$ | |
| 2.323 | 2-NO$_2$ | 6-F | H | OCH$_3$ | CH$_3$ | CH$_3$ | |

TABLE 2-continued

Compounds of formula

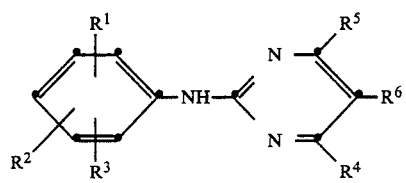

| | R¹ | R² | R³ | R⁴ | R⁵ | R⁶ | |
|---|---|---|---|---|---|---|---|
| 2.324 | 2-NO$_2$ | 6-F | H | CH$_3$ | CF$_3$ | CH$_3$ | |
| 2.325 | 2-NO$_2$ | 6-F | H | CF$_2$Cl | CH$_3$ | | |
| 2.326 | 2-NO$_2$ | 6-Br | H | CH$_3$ | Cl | CH$_3$ | |
| 2.327 | 2-NO$_2$ | 6-Br | H | CH$_3$ | CF$_3$ | CH$_3$ | |
| 2.328 | 2-NO$_2$ | 6-Br | H | C$_2$H$_5$ | CF$_3$ | CH$_3$ | |
| 2.329 | 2-NO$_2$ | 6-Br | H | Cyclopropyl | CF$_3$ | CH$_3$ | |
| 2.330 | 2-NO$_2$ | 6-Br | H | CH$_3$ | CHFCl | CH$_3$ | |
| 2.331 | 2-NO$_2$ | 6-Br | H | CH$_3$ | CF$_2$Cl | CH$_3$ | |
| 2.332 | 2-NO$_2$ | 6-Br | H | CH$_3$ | CHCl$_2$ | CH$_3$ | |
| 2.333 | 2-F | 5-F | H | CH$_3$ | Cl | CH$_3$ | |
| 2.334 | 2-F | 5-F | H | CH$_3$ | CF$_3$ | CH$_3$ | |
| 2.335 | 2-F | 5-F | H | C$_2$H$_5$ | CF$_3$ | CH$_3$ | |
| 2.336 | 2-F | 5-F | H | C$_2$H$_5$ | C$_2$F$_5$ | CH$_3$ | |
| 2.337 | 2-F | 5-F | H | C$_2$H$_5$ | CF$_2$Cl | CH$_3$ | |
| 2.338 | 2-F | 6-F | H | CH$_3$ | Cl | CH$_3$ | |
| 2.339 | 2-F | 6-F | H | CH$_3$ | CF$_3$ | CH$_3$ | |
| 2.340 | 2-F | 6-F | H | C$_2$H$_5$ | CF$_3$ | CH$_3$ | m.p. 75° |
| 2.341 | 2-F | 6-F | H | OCH$_3$ | CF$_3$ | CH$_3$ | |
| 2.342 | 2-F | 6-F | H | SCH$_3$ | CF$_3$ | CH$_3$ | |
| 2.343 | 2-F | 6-Cl | H | CH$_3$ | Cl | CH$_3$ | |
| 2.344 | 2-F | 6-Cl | H | CH$_3$ | CF$_3$ | CH$_3$ | |
| 2.345 | 2-F | 6-Cl | H | CH$_3$ | C$_2$F$_5$ | CH$_3$ | |
| 2.346 | 2-F | 6-Cl | H | C$_2$H$_5$ | CF$_3$ | CH$_3$ | |
| 2.347 | 2-F | 6-Cl | H | C$_2$H$_5$ | CF$_2$Cl | CH$_3$ | |
| 2.348 | 2-CF$_3$ | 6-Cl | H | CH$_3$ | Cl | CH$_3$ | |
| 2.349 | 2-CF$_3$ | 6-Cl | H | CH$_3$ | CF$_3$ | CH$_3$ | |
| 2.350 | 2-CF$_3$ | 6-Cl | H | C$_2$H$_5$ | CF$_3$ | CH$_3$ | |
| 2.351 | 2-CF$_3$ | 6-Cl | H | C$_2$H$_5$ | CF$_2$Cl | CH$_3$ | |
| 2.352 | 2-CF$_3$ | 6-Cl | H | CH$_3$ | C$_2$F$_5$ | CH$_3$ | |
| 2.353 | 2-CF$_3$ | 6-CH$_3$ | H | CH$_3$ | Cl | CH$_3$ | |
| 2.354 | 2-CF$_3$ | 6-CH$_3$ | H | CH$_3$ | CF$_3$ | CH$_3$ | |
| 2.355 | 2-CF$_3$ | 6-CH$_3$ | H | C$_2$H$_5$ | CF$_3$ | CH$_3$ | |
| 2.356 | 2-CF$_3$ | 6-CH$_3$ | H | Cyclopropyl | CF$_3$ | CH$_3$ | |
| 2.357 | 2-OCHF$_2$ | 5-Cl | H | CH$_3$ | Cl | CH$_3$ | |
| 2.358 | 2-OCHF$_2$ | 5-Cl | H | CH$_3$ | CF$_3$ | CH$_3$ | |
| 2.359 | 2-OCHF$_2$ | 5-Cl | H | C$_2$H$_5$ | CF$_3$ | CH$_3$ | |
| 2.360 | 2-OCHF$_2$ | 5-Cl | H | CH$_3$ | CF$_2$Cl | CH$_3$ | |
| 2.361 | 2-OCHF$_2$ | 5-Cl | H | CH$_3$ | CHCl$_2$ | CH$_3$ | |
| 2.362 | 2-OCHF$_2$ | 5-Cl | H | CF$_3$ | Cl | CH$_3$ | |
| 2.363 | 2-OCHF$_2$ | 5-Cl | H | OCH$_3$ | CF$_3$ | CH$_3$ | |
| 2.364 | 2-OCHF$_2$ | 5-Cl | H | SC$_2$H$_5$ | CF$_3$ | CH$_3$ | |
| 2.365 | 2-OCHF$_2$ | 5-Cl | H | CF$_3$ | Cl | C$_2$H$_5$ | |
| 2.366 | 2-OCHF$_2$ | 5-Cl | H | OCH$_3$ | CF$_3$ | C$_2$H$_5$ | |
| 2.367 | 2-OCHF$_2$ | 5-Cl | H | OC$_2$H$_5$ | CF$_3$ | C$_2$H$_5$ | |
| 2.368 | 2-OCHF$_2$ | 5-Cl | H | SCH$_3$ | CF$_3$ | C$_2$H$_5$ | |
| 2.369 | 2-OCF$_3$ | 5-Cl | H | CH$_3$ | Cl | CH$_3$ | |
| 2.370 | 2-OCF$_3$ | 5-Cl | H | CH$_3$ | CF$_3$ | CH$_3$ | |
| 2.371 | 2-OCF$_3$ | 5-Cl | H | C$_2$H$_5$ | CF$_3$ | CH$_3$ | |
| 2.372 | 2-OCF$_3$ | 5-Cl | H | CH$_3$ | C$_2$H$_5$ | CH$_3$ | |
| 2.373 | 2-OCF$_3$ | 5-Cl | H | CH$_3$ | CF$_2$Cl | CH$_3$ | |
| 2.374 | 2-C$_2$H$_5$ | 6-CH$_3$ | H | CH$_3$ | Cl | CH$_3$ | |
| 2.375 | 2-C$_2$H$_5$ | 6-CH$_3$ | H | CH$_3$ | CF$_3$ | CH$_3$ | |
| 2.376 | 2-C$_2$H$_5$ | 6-CH$_3$ | H | OCH$_3$ | CF$_3$ | CH$_3$ | |
| 2.377 | 2-C$_2$H$_5$ | 6-CH$_3$ | H | SCH$_3$ | CF$_3$ | CH$_3$ | |
| 2.378 | 2-C$_2$H$_5$ | 6-CH$_3$ | H | OC$_3$H$_7$(i) | CF$_3$ | CH$_3$ | |
| 2.379 | 2-CF$_3$ | 6-NO$_2$ | H | CH$_3$ | Cl | CH$_3$ | |
| 2.380 | 2-CF$_3$ | 6-NO$_2$ | H | CH$_3$ | CF$_3$ | CH$_3$ | |
| 2.381 | 2-NO$_2$ | 6-NO$_2$ | H | CH$_3$ | CF$_3$ | CH$_3$ | |
| 2.382 | 2-NO$_2$ | 6-NO$_2$ | H | OCH$_3$ | CF$_3$ | CH$_3$ | |
| 2.383 | 2-Cl | 6-Cl | 3-CH$_3$ | CH$_3$ | Cl | CH$_3$ | |
| 2.384 | 2-Cl | 6-Cl | 3-CH$_3$ | CH$_3$ | CF$_3$ | CH$_3$ | |
| 2.385 | 2-Cl | 6-Cl | 3-CH$_3$ | CH$_3$ | CF$_3$ | C$_2$H$_5$ | |
| 2.386 | 2-Cl | 6-Cl | 3-Cl | CH$_3$ | Cl | CH$_3$ | |
| 2.387 | 2-Cl | 6-Cl | 3-Cl | CH$_3$ | CF$_3$ | CH$_3$ | |
| 2.388 | 2-Cl | 6-Cl | 3-Cl | C$_2$H$_5$ | CF$_3$ | CH$_3$ | |
| 2.389 | 2-CH$_3$ | 3-Cl | H | CH$_3$ | Cl | CH$_3$ | |
| 2.390 | 2-CH$_3$ | 3-Cl | H | CH$_3$ | CF$_3$ | CH$_3$ | |
| 2.391 | 2-CH$_3$ | 3-Cl | H | C$_2$H$_5$ | CF$_3$ | CH$_3$ | |
| 2.392 | 2-CH$_3$ | 5-Cl | H | CH$_3$ | Cl | CH$_3$ | |
| 2.393 | 2-CH$_3$ | 5-Cl | H | CH$_3$ | CF$_3$ | CH$_3$ | |
| 2.394 | 2-CH$_3$ | 5-Cl | H | C$_2$H$_5$ | CF$_3$ | CH$_3$ | |
| 2.395 | 2-CH$_3$ | 5-Cl | H | C$_2$H$_5$ | CF$_2$Cl | CH$_3$ | |

TABLE 2-continued

Compounds of formula

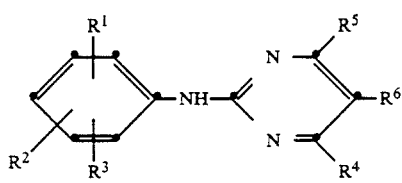

| Comp. No | R¹ | R² | R³ | R⁴ | R⁵ | R⁶ |
|---|---|---|---|---|---|---|
| 2.396 | 2-CH₃ | 5-Cl | H | OCH₃ | CF₃ | CH₃ |
| 2.397 | 2-CH₃ | 6-Cl | H | CH₃ | Cl | CH₃ |
| 2.398 | 2-CH₃ | 6-Cl | H | CH₃ | CF₃ | CH₃ |
| 2.399 | 2-CH₃ | 6-Cl | H | C₂H₅ | CF₃ | CH₃ |
| 2.400 | 2-CH₃ | 6-Cl | H | C₂H₅ | CHCl₂ | CH₃ |
| 2.401 | 2-CH₃ | 6-Cl | H | C₂H₅ | CF₂Cl | CH₃ |
| 2.402 | 2-CH₃ | 6-Cl | H | OC₂H₅ | CF₃ | CH₃ |
| 2.403 | 2-CH₃ | 6-Cl | H | SCH₃ | CF₃ | CH₃ |
| 2.404 | 2-CH₃ | 6-Cl | H | OC₄H₉(n) | CF₃ | CH₃ |
| 2.405 | 2-CH₃ | 6-Cl | H | CH₃ | Cl | SCH₃ |
| 2.406 | 2-CH₃ | 6-CH₃ | H | CH₃ | Cl | CH₃ |
| 2.407 | 2-CH₃ | 6-CH₃ | H | CH₃ | CF₃ | CH₃ |
| 2.408 | 2-CH₃ | 6-CH₃ | H | C₂H₅ | CF₃ | CH₃ |
| 2.409 | 2-CH₃ | 6-CH₃ | H | Cyclopropyl | CF₃ | CH₃ |
| 2.410 | 2-CH₃ | 6-CH₃ | H | C₂H₅ | CF₂Cl | CH₃ |
| 2.411 | 2-Cl | 3-CH₃ | H | CH₃ | Cl | CH₃ |
| 2.412 | 2-Cl | 3-CH₃ | H | CH₃ | CF₃ | CH₃ |
| 2.413 | 2-Cl | 3-CH₃ | H | C₂H₅ | CF₃ | CH₃ |
| 2.414 | 2-Cl | 5-CH₃ | H | CH₃ | Cl | CH₃ |
| 2.415 | 2-Cl | 5-CH₃ | H | CH₃ | CF₃ | CH₃ |
| 2.416 | 2-Cl | 5-CH₃ | H | C₂H₅ | CF₃ | CH₃ |
| 2.417 | 2-Cl | 5-CH₃ | H | C₂H₅ | CF₂Cl | CH₃ |
| 2.418 | 2-NO₂ | H | H | CH₂Cl | Cl | CH₃ |
| 2.419 | 2-NO₂ | H | H | CH₂OCH₃ | Cl | CH₃ |
| 2.420 | 2-NO₂ | H | H | CH₃ | Cl | SCH₃ |
| 2.421 | 2-NO₂ | H | H | CH₃ | Cl | SC₂H₅ |
| 2.422 | 2-NO₂ | H | H | CH₃ | Cl | OCH₃ |
| 2.423 | 2-NO₂ | H | H | CH₃ | Cl | OC₂H₅ |
| 2.424 | 2-NO₂ | 6-CH₃ | H | CH₂OCH₃ | Cl | CH₃ |
| 2.425 | 2-NO₂ | 6-CH₃ | H | CH₃ | Cl | SCH₃ |
| 2.426 | 2-NO₂ | 6-CH₃ | H | CH₃ | Cl | OC₂H₅ |
| 2.427 | 2-NO₂ | 6-CH₃ | H | CH₃ | Cl | SC₂H₅ |
| 2.428 | 2-NO₂ | 6-CH₃ | H | CH₃ | Cl | SC₃H₇(i) |
| 2.429 | 2-Cl | 5-Cl | H | CH₃ | Cl | OCH₃ |
| 2.430 | 2-Cl | 5-Cl | H | CH₃ | Cl | SCH₃ |
| 2.431 | 2-Cl | 5-Cl | H | CH₃ | Cl | OC₂H₅ |
| 2.432 | 2-Cl | 6-Cl | H | CH₂OCH₃ | CF₃ | CH₃ |
| 2.433 | 2-Cl | 6-Cl | H | CH₂OCH₃ | Cl | CH₃ |
| 2.434 | 2-Cl | 6-Cl | H | CH₃ | Cl | OCH₃ |
| 2.435 | 2-Cl | 6-Cl | H | CH₃ | Cl | SCH₃ |
| 2.436 | 2-Cl | 6-Cl | H | CH₃ | Cl | OC₂H₅ |
| 2.437 | 2-Cl | 6-Cl | H | CH₃ | Cl | SC₂H₅ |
| 2.438 | 2-NO₂ | H | H | CH₂COOCH₃ | CF₃ | CH₃ |
| 2.4389 | 2-NO₂ | H | H | CH₂C(=O)CH₃ | CF₃ | CH₃ |
| 2.440 | 2-OCH₃ | 5-Cl | H | CH₃ | Cl | CH₃ |
| 2.441 | 2-OCH₃ | 5-Cl | H | CH₃ | CF₃ | CH₃ |
| 2.442 | 2-OCH₃ | 5-Cl | H | C₂H₅ | CF₃ | CH₃ |
| 2.443 | 2-OCH₃ | 5-Cl | H | CH₃ | CF₂Cl | CH₃ |
| 2.444 | 2-OCH₃ | 5-Cl | H | CH₃ | C₂F₅ | CH₃ |
| 2.445 | 2-OCH₃ | 5-Cl | H | Cyclopropyl | CF₃ | CH₃ |

| Comp. No | R¹ | R² | R³ | —R⁵—R⁶— | R⁴ | Phys. data |
|---|---|---|---|---|---|---|
| 2.446 | 2-NO₂ | H | H | —CH₂—CH₂— | CF₃ | |
| 2.447 | 2-NO₂ | H | H | —CHCH₃—CH₂— | CF₃ | |
| 2.448 | 2-NO₂ | H | H | —CH₂—CH₂— | CF₂Cl | |
| 2.449 | 2-NO₂ | H | H | —(CH₂)₃— | CF₃ | m.p. 148–150° C. |
| 2.450 | 2-NO₂ | H | H | —(CH₂)₃— | Cl | |
| 2.451 | 2-NO₂ | H | H | —(CH₂)₃— | OCH₃ | |
| 2.452 | 2-NO₂ | H | H | —(CH₂)₃— | SCH₃ | |
| 2.453 | 2-NO₂ | H | H | —(CH₂)₃— | SOCH₃ | |
| 2.454 | 2-NO₂ | H | H | —(CH₂)₃— | SO₂CH₃ | |
| 2.455 | 2-NO₂ | H | H | —CHCH₃—CH₂—CH₂— | CF₃ | |
| 2.456 | 2-NO₂ | H | H | —CHCH₃—CH₂—CH₂— | Cl | |
| 2.457 | 2-NO₂ | H | H | —CHCH₃—CH₂—CH₂— | CHCl₂ | |
| 2.458 | 2-NO₂ | H | H | —CHCH₃—CH₂—CH₂— | CHFCl | |
| 2.459 | 2-NO₂ | H | H | —CHCH₃—CH₂—CH₂— | CF₂Cl | |
| 2.460 | 2-NO₂ | H | H | —C(CH₃)₂—CH₂—CH₂— | CF₃ | |
| 2.461 | 2-NO₂ | H | H | —C(CH₃)₂—CH₂CH₂ | Cl | |

TABLE 2-continued

Compounds of formula

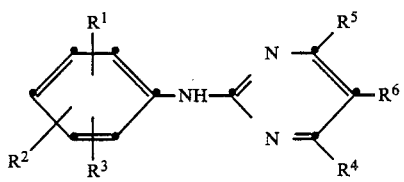

| No. | R¹ | R² | R³ | R⁴ | R⁵/R⁶ | m.p. |
|---|---|---|---|---|---|---|
| 2.462 | 2-NO$_2$ | H | H | —C(CH$_3$)$_2$—CH$_2$—CH$_2$— | CF$_2$CF$_3$ | |
| 2.463 | 2-NO$_2$ | H | H | —CH=CCH$_3$—CH$_2$— | CF$_3$ | |
| 2.464 | 2-NO$_2$ | H | H | —CH=CCH$_3$—CH$_2$— | Cl | |
| 2.465 | 2-NO$_2$ | H | H | —CH=CCH$_3$—CH$_2$— | CHF$_2$ | |
| 2.466 | 2-NO$_2$ | H | H | —CH$_2$—CHCH$_3$—CH$_2$— | Cl | |
| 2.467 | 2-NO$_2$ | H | H | —CH$_2$—CHCH$_3$—CH$_2$— | CF$_3$ | |
| 2.468 | 2-NO$_2$ | H | H | —CH$_2$—CH$_2$—CHCH$_3$— | Cl | |
| 2.469 | 2-NO$_2$ | H | H | —CH$_2$—CH$_2$—CHCH$_3$— | CF$_3$ | |
| 2.470 | 2-NO$_2$ | H | H | —CH(COOCH$_3$)—CH$_2$—CH$_2$— | Cl | |
| 2.471 | 2-NO$_2$ | H | H | —CH(COOC$_2$H$_5$)—CH$_2$—CH$_2$— | Cl | |
| 2.472 | 2-NO$_2$ | H | H | —CH$_2$—CH$_2$—S— | Cl | |
| 2.473 | 2-NO$_2$ | H | H | —CH$_2$—CH$_2$—S— | CF$_3$ | |
| 2.474 | 2-NO$_2$ | H | H | —CH$_2$—CH$_2$—S— | CF$_2$Cl | |
| 2.475 | 2-NO$_2$ | H | H | —CH$_2$—CH$_2$—S— | CHCl$_2$ | |
| 2.476 | 2-NO$_2$ | H | H | —CH$_2$—C(CH$_3$)$_2$—CH$_2$— | Cl | |
| 2.477 | 2-NO$_2$ | H | H | —CH$_2$—C(CH$_3$)$_2$—CH$_2$— | CF$_3$ | |
| 2.478 | 2-NO$_2$ | H | H | —CH$_2$—C(CH$_3$)$_2$—CH$_2$— | CF$_2$CF$_3$ | |
| 2.479 | 2-NO$_2$ | H | H | —CH$_2$—CH$_2$—C(CH$_3$)$_2$— | Cl | |
| 2.480 | 2-NO$_2$ | H | H | —CH$_2$—CH$_2$—C(CH$_3$)$_2$— | CF$_3$ | |
| 2.481 | 2-NO$_2$ | H | H | —CH$_2$—CH$_2$—C(CH$_3$)$_2$— | CF$_2$CF$_3$ | |
| 2.482 | 2-NO$_2$ | H | H | —CHCH$_3$—CHCH$_3$—CH$_2$— | Cl | |
| 2.483 | 2-NO$_2$ | H | H | —CHCH$_3$—CHCH$_3$—CH$_2$— | CF$_3$ | |
| 2.484 | 2-NO$_2$ | H | H | —CHCH$_3$—CHCH$_3$—CH$_2$— | CF$_2$Cl | |
| 2.485 | 2-NO$_2$ | H | H | —CH(C$_2$H$_5$)—CH$_2$—CH$_2$— | Cl | |
| 2.486 | 2-NO$_2$ | H | H | —CH(C$_2$H$_5$)—CH$_2$—CH$_2$— | CF$_3$ | |
| 2.487 | 2-NO$_2$ | H | H | —C(CH$_3$)(C$_2$H$_5$)—CH$_2$—CH$_2$ | Cl | |
| 2.488 | 2-NO$_2$ | H | H | —C(CH$_3$)(C$_2$H$_5$)—CH$_2$CH$_2$ | CF$_3$ | |
| 2.489 | 2-NO$_2$ | H | H | —CHCH$_3$—(CH$_2$)$_3$— | Cl | |
| 2.490 | 2-NO$_2$ | H | H | —CHCH$_3$—(CH$_2$)$_3$— | CF$_3$ | m.p. 88–89° C. |
| 2.491 | 2-NO$_2$ | H | H | —CHCH$_3$—(CH$_2$)$_3$— | CF$_2$CF$_3$ | |
| 2.492 | 2-NO$_2$ | H | H | —CHCH$_3$—(CH$_2$)$_3$— | CF$_2$Cl | |
| 2.493 | 2-NO$_2$ | H | H | —CHCH$_3$—(CH$_2$)$_3$— | CHF$_2$ | |
| 2.494 | 2-NO$_2$ | H | H | —(CH$_2$)$_4$— | Cl | m.p. 153–154° C. |
| 2.495 | 2-NO$_2$ | H | H | —(CH$_2$)$_4$— | OCH$_3$ | m.p. 109–112° C. |
| 2.496 | 2-NO$_2$ | H | H | —(CH$_2$)$_4$— | CF$_3$ | m.p. 129–130° C. |
| 2.497 | 2-NO$_2$ | H | H | —(CH$_2$)$_4$— | CHF$_2$ | m.p. 127–128° C. |
| 2.498 | 2-NO$_2$ | H | H | —(CH$_2$)$_4$— | CHCl$_2$ | |
| 2.499 | 2-NO$_2$ | H | H | —(CH$_2$)$_4$— | CHFCl | |
| 2.500 | 2-NO$_2$ | H | H | —(CH$_2$)$_4$— | CF$_2$CF$_3$ | |
| 2.501 | 2-NO$_2$ | H | H | —(CH$_2$)$_4$— | C$_3$F$_7$(n) | |
| 2.502 | 2-NO$_2$ | H | H | —(CH$_2$)$_4$— | CCl$_2$CF$_3$ | |
| 2.503 | 2-NO$_2$ | H | H | —(CH$_2$)$_4$— | SCH$_3$ | |
| 2.504 | 2-NO$_2$ | H | H | —(CH$_2$)$_4$— | SOCH$_3$ | |
| 2.505 | 2-NO$_2$ | H | H | —(CH$_2$)$_4$— | SO$_2$CH$_3$ | |
| 2.506 | 2-NO$_2$ | H | H | —C(CH$_3$)$_2$—(CH$_2$)$_3$— | Cl | |
| 2.507 | 2-NO$_2$ | H | H | —C(CH$_3$)$_2$—(CH$_2$)$_3$— | CF$_3$ | |
| 2.508 | 2-NO$_2$ | H | H | —C(CH$_3$)$_2$—(CH$_2$)$_3$— | CF$_2$Cl | |
| 2.509 | 2-NO$_2$ | H | H | —C(CH$_3$)$_2$—(CH$_2$)$_3$— | CHF$_2$ | |
| 2.510 | 2-NO$_2$ | H | H | —C(CH$_3$)$_2$—(CH$_2$)$_3$— | CF$_2$CF$_3$ | |
| 2.511 | 2-NO$_2$ | H | H | —CH$_2$—CHCH$_3$—(CH$_2$)$_2$— | Cl | |
| 2.512 | 2-NO$_2$ | H | H | —CH$_2$—CHCH$_3$—(CH$_2$)$_2$— | CF$_3$ | m.p. 119–120° C. |
| 2.513 | 2-NO$_2$ | H | H | —(CH$_2$)$_3$—CHCH$_3$— | Cl | |
| 2.514 | 2-NO$_2$ | H | H | —(CH$_2$)$_3$—CHCH$_3$— | CF$_3$ | |
| 2.515 | 2-NO$_2$ | H | H | —(CH$_2$)$_2$—CHCH$_3$—CH$_2$— | Cl | |
| 2.516 | 2-NO$_2$ | H | H | —(CH$_2$)$_2$—CHCH$_3$—CH$_2$— | OCH$_3$ | |
| 2.517 | 2-NO$_2$ | H | H | —(CH$_2$)$_2$—CHCH$_3$—CH$_2$— | CF$_3$ | m.p. 184–185° C. |
| 2.518 | 2-NO$_2$ | H | H | —(CH$_2$)$_2$—CHCH$_3$—CH$_2$— | CF$_2$Cl | |
| 2.519 | 2-NO$_2$ | H | H | —(CH$_2$)$_2$—CHCH$_3$—CH$_2$— | CHCl$_2$ | |
| 2.520 | 2-NO$_2$ | H | H | —(CH$_2$)$_2$—C(CH$_3$)$_2$—CH$_2$— | Cl | |
| 2.521 | 2-NO$_2$ | H | H | —(CH$_2$)$_2$—C(CH$_3$)$_2$—CH$_3$— | CF$_3$ | |
| 2.522 | 2-NO$_2$ | H | H | —CH=CCH$_3$—CH$_2$—C(CH$_3$)$_2$— | Cl | |
| 2.523 | 2-NO$_2$ | H | H | —CH=CCH$_3$—CH$_2$—C(CH$_3$)$_2$— | CF$_3$ | |
| 2.524 | 2-NO$_2$ | H | H | —CH$_2$—CH(OCH$_3$)—(CH$_2$)$_2$ | Cl | |
| 2.525 | 2-NO$_2$ | H | H | —CH$_2$—CH(OCH$_3$)—(CH$_2$)$_2$ | CF$_3$ | |
| 2.526 | 2-NO$_2$ | H | H | —(CH$_2$)$_2$—S—CH$_2$— | Cl | |
| 2.527 | 2-NO$_2$ | H | H | —(CH$_2$)$_2$—S—CH$_2$— | CF$_3$ | |
| 2.528 | 2-NO$_2$ | H | H | —(CH$_2$)$_2$—O—CH$_2$— | Cl | |
| 2.529 | 2-NO$_2$ | H | H | —(CH$_2$)$_2$—NCH$_3$—CH$_2$— | CF$_3$ | m.p. 194–195° C. |
| 2.530 | 2-NO$_2$ | H | H | —O—(CH$_2$)$_2$— | CF$_3$ | |
| 2.531 | 2-NO$_2$ | H | H | —O—(CH$_2$)$_3$— | CF$_3$ | |
| 2.532 | 2-NO$_2$ | H | H | —CH(COOC$_2$H$_5$)—(CH$_2$)$_3$ | Cl | |
| 2.533 | 2-NO$_2$ | H | H | —CH(COOC$_2$H$_5$)—(CH$_2$)$_3$ | CF$_3$ | |

TABLE 2-continued

Compounds of formula

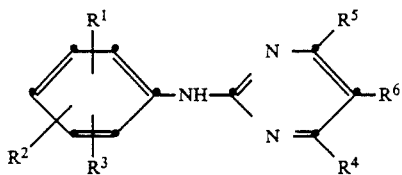

| | $R^1$ | $R^2$ | $R^3$ | | $R^6$ | |
|---|---|---|---|---|---|---|
| 2.534 | 2-$NO_2$ | H | H | —$CHCH_3$—$CH_2$—$C(CH_3)_2$—$CH_2$— | Cl | |
| 2.535 | 2-$NO_2$ | H | H | —$CHCH_3$—$CH_2$—$C(CH_3)_2$—$CH_2$— | $CF_3$ | |
| 2.536 | 2-$NO_2$ | H | H | —$CHCH_3$—$CH_2$—$C(CH_3)_2$—$CH_2$— | $CF_2CF_3$ | |
| 2.537 | 2-$NO_2$ | H | H | —$(CH_2)_5$— | Cl | |
| 2.538 | 2-$NO_2$ | H | H | —$(CH_2)_5$— | $CF_3$ | m.p. 148–149° C. |
| 2.539 | 2-$NO_2$ | H | H | —$CHCH_3$—$(CH_2)_4$— | Cl | |
| 2.540 | 2-$NO_2$ | H | H | —$CHCH_3$—$(CH_2)_4$— | $CF_3$ | |
| 2.541 | 2-$NO_2$ | H | H | —$C(CH_3)_2$—$(CH_2)_4$— | Cl | |
| 2.542 | 2-$NO_2$ | H | H | —$C(CH_3)_2$—$(CH_2)_4$— | $CF_3$ | |
| 2.543 | 2-$NO_2$ | H | H | —$(CH_2)_6$— | Cl | |
| 2.544 | 2-$NO_2$ | H | H | —$(CH_2)_6$— | $CF_3$ | m.p. 150–151° C. |
| 2.545 | 2-$NO_2$ | 6-$CH_3$ | H | —$(CH_2)_3$— | $CF_3$ | m.p. 135–136° C. |
| 2.546 | 2-$NO_2$ | 6-$CH_3$ | H | —$(CH_2)_3$— | Cl | |
| 2.547 | 2-$NO_2$ | 6-$CH_3$ | H | —$(CH_2)_3$— | $OCH_3$ | |
| 2.548 | 2-$NO_2$ | 6-$CH_3$ | H | —$(CH_2)_3$— | $CF_2Cl$ | m.p. 116–118° C. |
| 2.549 | 2-$NO_2$ | 6-$CH_3$ | H | —$(CH_2)_3$— | $CF_2CF_3$ | |
| 2.550 | 2-$NO_2$ | 6-$CH_3$ | H | —$(CH_2)_3$— | $CHCl_2$ | |
| 2.551 | 2-$NO_2$ | 6-$CH_3$ | H | —$CHCH_3$—$CH_2$—$CH_2$— | Cl | |
| 2.552 | 2-$NO_2$ | 6-$CH_3$ | H | —$CHCH_3$—$CH_2$—$CH_2$ | $CF_3$ | |
| 2.553 | 2-$NO_2$ | 6-$CH_3$ | H | —$CHCH_3$—$CH_2$—$CH_2$ | $CF_2Cl$ | |
| 2.554 | 2-$NO_2$ | 6-$CH_3$ | H | —$C(CH_3)_2$—$CH_2$—$CH_2$— | Cl | |
| 2.555 | 2-$NO_2$ | 6-$CH_3$ | H | —$C(CH_3)_2$—$CH_2$—$CH_2$— | $CF_3$ | |
| 2.556 | 2-$NO_2$ | 6-$CH_3$ | H | —$C(CH_3)_2$—$CH_2$—$CH_2$— | $CF_2CF_3$ | |
| 2.557 | 2-$NO_2$ | 6-$CH_3$ | H | —$C(CH_3)_2$—$CH_2$—$CH_2$— | $CF_2Cl$ | |
| 2.558 | 2-$NO_2$ | 6-$CH_3$ | H | —$C(CH_3)_2$—$CH_2$—$CH_2$— | $CHCl_2$ | |
| 2.559 | 2-$NO_2$ | 6-$CH_3$ | H | —$CH_2$—$CH_2$—S— | Cl | |
| 2.560 | 2-$NO_2$ | 6-$CH_3$ | H | —$CH_2$—$CH_2$—S— | $CF_3$ | |
| 2.561 | 2-$NO_2$ | 6-$CH_3$ | H | —$(CH_2)_4$— | Cl | |
| 2.562 | 2-$NO_2$ | 6-$CH_3$ | H | —$(CH_2)_4$— | $OCH_3$ | |
| 2.563 | 2-$NO_2$ | 6-$CH_3$ | H | —$(CH_2)_4$— | $CF_3$ | m.p. 103–104° C. |
| 2.564 | 2-$NO_2$ | 6-$CH_3$ | H | —$(CH_2)_4$— | $CF_2Cl$ | m.p. 85–86° C. |
| 2.565 | 2-$NO_2$ | 6-$CH_3$ | H | —$(CH_2)_4$— | $CHF_2$ | m.p. 124–126° C. |
| 2.566 | 2-$NO_2$ | 6-$CH_3$ | H | —$(CH_2)_4$— | CHFCl | |
| 2.567 | 2-$NO_2$ | 6-$CH_3$ | H | —$(CH_2)_4$— | $CHCl_2$ | |
| 2.568 | 2-$NO_2$ | 6-$CH_3$ | H | —$(CH_2)_4$— | $CF_2CF_3$ | |
| 2.569 | 2-$NO_2$ | 6-$CH_3$ | H | —$(CH_2)_4$— | $C_3F_7(n)$ | |
| 2.570 | 2-$NO_2$ | 6-$CH_3$ | H | —$(CH_2)_4$— | $CCl_2CF_3$ | |
| 2.571 | 2-$NO_2$ | 6-$CH_3$ | H | —$(CH_2)_4$— | $SCH_3$ | |
| 2.572 | 2-$NO_2$ | 6-$CH_3$ | H | —$(CH_2)_4$ | $SOCH_3$ | |
| 2.573 | 2-$NO_2$ | 6-$CH_3$ | H | —$(CH_2)_4$ | $SO_2CH_3$ | |
| 2.574 | 2-$NO_2$ | 6-$CH_3$ | H | —$C(CH_3)_2$—$(CH_2)_3$— | Cl | |
| 2.575 | 2-$NO_2$ | 6-$CH_3$ | H | —$C(CH_3)_2$—$(CH_2)_3$— | $CF_3$ | |
| 2.576 | 2-$NO_2$ | 6-$CH_3$ | H | —$CH_2$—$CHCH_3$—$(CH_2)_2$— | Cl | |
| 2.577 | 2-$NO_2$ | 6-$CH_3$ | H | —$CH_2$—$CHCH_3$—$(CH_2)_2$— | $CF_3$ | m.p. 154–155° C. |
| 2.578 | 2-$NO_2$ | 6-$CH_3$ | H | —$CH_2$—$CHCH_3$—$(CH_2)_2$— | $CF_2Cl$ | |
| 2.579 | 2-$NO_2$ | 6-$CH_3$ | H | —$CH_2$—$CHCH_3$—$(CH_2)_2$— | $CHCl_2$ | |
| 2.580 | 2-$NO_2$ | 6-$CH_3$ | H | —$(CH_2)_2$—$NCH_3$—$CH_2$— | $CF_3$ | |
| 2.581 | 2-$NO_2$ | 6-$CH_3$ | H | —$(CH_2)_5$— | Cl | |
| 2.582 | 2-$NO_2$ | 6-$CH_3$ | H | —$(CH_2)_5$— | $CF_3$ | oil |
| 2.583 | 2-$NO_2$ | 6-$CH_3$ | H | —$CH_2$—$CH_2$—$CH_2$—O— | Cl | |
| 2.584 | 2-$NO_2$ | 6-$CH_3$ | H | —$CH_2$—$CH_2$—O— | $CF_3$ | |
| 2.585 | 2-Cl | H | H | —$(CH_2)_3$— | $CF_3$ | |
| 2.586 | 2-Cl | H | H | —$(CH_2)_4$— | $CF_3$ | |
| 2.587 | 2-Cl | 5-Cl | H | —$(CH_2)_3$— | Cl | |
| 2.588 | 2-Cl | 5-Cl | H | —$(CH_2)_3$— | $CF_3$ | m.p. 127–128° C. |
| 2.589 | 2-Cl | 5-Cl | H | —$(CH_2)_3$— | $OCH_3$ | |
| 2.590 | 2-Cl | 5-Cl | H | —$(CH_2)_3$— | $CF_2Cl$ | |
| 2.591 | 2-Cl | 5-Cl | H | —$(CH_2)_3$— | $CF_2CF_3$ | |
| 2.592 | 2-Cl | 5-Cl | H | —$(CH_2)_3$— | $CHCl_2$ | |
| 2.593 | 2-Cl | 5-Cl | H | —$C(CH_3)_2$—$CH_2$—$CH_2$— | Cl | |
| 2.594 | 2-Cl | 5-Cl | H | —$C(CH_3)_2$—$CH_2$—$CH_2$— | $OCH_3$ | |
| 2.595 | 2-Cl | 5-Cl | H | —$C(CH_3)_2$—$CH_2$—$CH_2$— | $CF_3$ | |
| 2.596 | 2-Cl | 5-Cl | H | —$C(CH_3)_2$—$CH_2$—$CH_2$— | $CF_2Cl$ | |
| 2.597 | 2-Cl | 5-Cl | H | —$C(CH_3)_2$—$CH_2$—$CH_2$— | $CHCl_2$ | |
| 2.598 | 2-Cl | 5-Cl | H | —$C(CH_3)_2$—$CH_2$—$CH_2$— | $CF_2CF_3$ | |
| 2.599 | 2-Cl | 5-Cl | H | —$CH_2$—$CH_2$—S— | Cl | |
| 2.600 | 2-Cl | 5-Cl | H | —$CH_2$—$CH_2$—S— | $CF_3$ | |
| 2.601 | 2-Cl | 5-Cl | H | —$(CH_2)_4$— | Cl | m.p. 119–120° C. |
| 2.602 | 2-Cl | 5-Cl | H | —$(CH_2)_4$— | $OCH_3$ | m.p. 101–103° C. |
| 2.603 | 2-Cl | 5-Cl | H | —$(CH_2)_4$— | $SCH_3$ | |
| 2.604 | 2-Cl | 5-Cl | H | —$(CH_2)_4$— | $SOCH_3$ | |
| 2.605 | 2-Cl | 5-Cl | H | —$(CH_2)_4$— | $SO_2CH_3$ | |

TABLE 2-continued

Compounds of formula

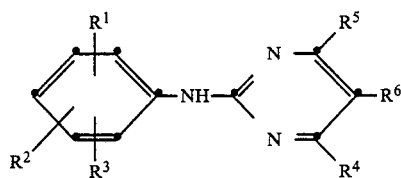

| | $R^1$ | $R^2$ | $R^3$ | $R^4$ / (bridge) | $R^5$/$R^6$ | |
|---|---|---|---|---|---|---|
| 2.606 | 2-Cl | 5-Cl | H | —(CH$_2$)$_4$— | CF$_3$ | m.p. 123–124° C. |
| 2.607 | 2-Cl | 5-Cl | H | —(CH$_2$)$_4$— | CF$_2$Cl | |
| 2.608 | 2-Cl | 5-Cl | H | —(CH$_2$)$_4$— | CHF$_2$ | |
| 2.609 | 2-Cl | 5-Cl | H | —(CH$_2$)$_4$— | CHCl$_2$ | |
| 2.610 | 2-Cl | 5-Cl | H | —(CH$_2$)$_4$— | CHFCl | |
| 2.611 | 2-Cl | 5-Cl | H | —(CH$_2$)$_4$— | CF$_2$CF$_3$ | |
| 2.612 | 2-Cl | 5-Cl | H | —(CH$_2$)$_4$— | C$_3$F$_7$n | |
| 2.613 | 2-Cl | 5-Cl | H | —C(CH$_3$)$_2$—(CH$_2$)$_3$— | Cl | |
| 2.614 | 2-Cl | 5-Cl | H | —C(CH$_3$)$_2$—(CH$_2$)$_3$— | OCH$_3$ | |
| 2.615 | 2-Cl | 5-Cl | H | —C(CH$_3$)$_2$—(CH$_2$)$_3$— | CF$_3$ | |
| 2.616 | 2-Cl | 5-Cl | H | —C(CH$_3$)$_2$—(CH$_2$)$_3$— | CF$_2$Cl | |
| 2.617 | 2-Cl | 5-Cl | H | —(CH$_2$)$_5$— | Cl | |
| 2.618 | 2-Cl | 5-Cl | H | —(CH$_2$)$_5$— | OCH$_3$ | |
| 2.619 | 2-Cl | 5-Cl | H | —(CH$_2$)$_5$— | CF$_3$ | m.p. 104–105° C. |
| 2.620 | 2-Cl | 5-Cl | H | —(CH$_2$)$_5$— | CF$_2$Cl | |
| 2.621 | 2-Cl | 5-Cl | H | —(CH$_2$)$_6$— | Cl | |
| 2.622 | 2-Cl | 5-Cl | H | —(CH$_2$)$_6$— | OCH$_3$ | |
| 2.623 | 2-Cl | 5-Cl | H | —(CH$_2$)$_6$— | CF$_3$ | m.p. 91–92° C. |
| 2.624 | 2-Cl | 6-Cl | H | —(CH$_2$)$_6$— | CF$_2$Cl | |
| 2.625 | 2-Cl | 6-Cl | H | —(CH$_2$)$_3$— | Cl | |
| 2.626 | 2-Cl | 6-Cl | H | —(CH$_2$)$_3$— | OCH$_3$ | |
| 2.627 | 2-Cl | 6-Cl | H | —(CH$_3$)$_2$— | CF$_3$ | m.p. 169–170° C. |
| 2.628 | 2-Cl | 6-Cl | H | —(CH$_2$)$_3$— | CF$_2$Cl | |
| 2.629 | 2-Cl | 6-Cl | H | —(CH$_2$)$_3$— | CHF$_2$ | m.p. 145–146° C. |
| 2.630 | 2-Cl | 6-Cl | H | —(CH$_2$)$_3$— | CF$_2$CF$_3$ | |
| 2.631 | 2-Cl | 6-Cl | H | —(CH$_2$)$_4$— | Cl | |
| 2.632 | 2-Cl | 6-Cl | H | —(CH$_2$)$_4$— | OCH$_3$ | |
| 2.633 | 2-Cl | 6-Cl | H | —(CH$_2$)$_4$— | CF$_3$ | m.p. 165–166° C. |
| 2.634 | 2-Cl | 6-Cl | H | —(CH$_2$)$_4$— | CF$_2$Cl | |
| 2.635 | 2-Cl | 6-Cl | H | —(CH$_2$)$_4$— | CHCl$_2$ | |
| 2.636 | 2-Cl | 6-Cl | H | —(CH$_2$)$_4$— | CHF$_2$ | |
| 2.637 | 2-Cl | 6-Cl | H | —CH$_2$—CH$_2$—CHCH$_3$—CH$_3$— | CF$_3$ | |
| 2.638 | 2-Cl | 6-Cl | H | —CH$_2$—CH$_2$—CHCH$_3$—CH$_3$— | CF$_2$Cl | |
| 2.639 | 2-Cl | 6-Cl | H | —CH$_2$—CH$_2$—CHCH$_3$—CH$_2$— | CHF$_3$ | |
| 2.640 | 2-Cl | 6-Cl | H | —(CH$_2$)$_5$— | CF$_3$ | |
| 2.641 | 2-Cl | 6-CH$_3$ | H | —(CH$_2$)$_3$— | Cl | |
| 2.642 | 2-Cl | 6-CH$_3$ | H | —(CH$_2$)$_3$— | CF$_3$ | m.p. 138–141° C. |
| 2.643 | 2-Cl | 6-CH$_3$ | H | —(CH$_2$)$_3$— | CF$_2$Cl | m.p. 135–137° C. |
| 2.644 | 2-Cl | 6-CH$_3$ | H | —(CH$_2$)$_3$— | CHF$_2$ | m.p. 129–130° C. |
| 2.645 | 2-Cl | 6-CH$_3$ | H | —(CH$_2$)$_4$— | Cl | |
| 2.646 | 2-Cl | 6-CH$_3$ | H | —(CH$_2$)$_4$— | CF$_3$ | m.p. 131–132° C. |
| 2.647 | 2-Cl | 6-CH$_3$ | H | —(CH$_2$)$_4$— | CF$_2$Cl | m.p. 101–103° C. |
| 2.648 | 2-Cl | 6-CH$_3$ | H | —(CH$_2$)$_4$— | CHF$_2$ | m.p. 134–136° C. |
| 2.649 | 2-Cl | 6-CH$_3$ | H | —(CH$_2$)$_5$— | CF$_3$ | |
| 2.650 | 2-Cl | 6-CH$_3$ | H | —(CH$_2$)$_6$— | CF$_3$ | |
| 2.651 | 2-Br | H | H | —(CH$_2$)$_3$— | Cl | |
| 2.652 | 2-Br | H | H | —(CH$_2$)$_3$— | CF$_3$ | |
| 2.653 | 2-Br | H | H | —(CH$_2$)$_4$— | Cl | |
| 2.654 | 2-Br | H | H | —(CH$_2$)$_4$— | CF$_3$ | |
| 2.655 | 2-Br | H | H | —(CH$_2$)$_4$— | CF$_2$Cl | |
| 2.656 | 2-CF$_3$ | H | H | —(CH$_2$)$_3$— | Cl | |
| 2.657 | 2-CF$_3$ | H | H | —(CH$_2$)$_3$— | CF$_3$ | |
| 2.658 | 2-CF$_3$ | H | H | —(CH$_2$)$_3$— | CF$_2$Cl | |
| 2.659 | 2-CF$_3$ | 6-Cl | H | —(CH$_2$)$_3$— | CF$_3$ | |
| 2.660 | 2-CF$_3$ | 6-Cl | H | —(CH$_2$)$_4$— | CF$_3$ | |
| 2.661 | 2-OCH$_3$ | H | H | —(CH$_2$)$_3$— | Cl | |
| 2.662 | 2-OCH$_3$ | H | H | —(CH$_2$)$_3$— | CF$_3$ | |
| 2.663 | 2-OCH$_3$ | H | H | —(CH$_2$)$_4$— | Cl | |
| 2.664 | 2-OCH$_3$ | H | H | —(CH$_2$)$_4$— | CF$_3$ | |
| 2.665 | 2-OCH$_3$ | 5-Cl | H | —(CH$_2$)$_3$— | Cl | |
| 2.666 | 2-OCH$_3$ | 5-Cl | H | —(CH$_2$)$_3$— | CF$_3$ | |
| 2.667 | 2-OCH$_3$ | 5-Cl | H | —(CH$_2$)$_4$— | Cl | |
| 2.668 | 2-OCH$_3$ | 5-Cl | H | —(CH$_2$)$_4$— | CF$_3$ | |
| 2.669 | 2-OCHF$_2$ | H | H | —(CH$_2$)$_3$— | Cl | |
| 2.670 | 2-OCHF$_2$ | H | H | —(CH$_2$)$_3$— | CF$_3$ | |
| 2.671 | 2-OCHF$_2$ | H | H | —(CH$_2$)$_4$— | Cl | |
| 2.672 | 2-OCHF$_2$ | H | H | —(CH$_2$)$_4$— | CF$_3$ | m.p. 114–115° C. |
| 2.673 | 2-OCHF$_2$ | 5-Cl | H | —(CH$_2$)$_3$— | Cl | |
| 2.674 | 2-OCHF$_2$ | 5-Cl | H | —(CH$_2$)$_3$— | CF$_3$ | |
| 2.675 | 2-OCHF$_2$ | 5-Cl | H | —(CH$_2$)$_4$— | Cl | |
| 2.676 | 2-OCHF$_2$ | 5-Cl | H | —(CH$_2$)$_4$— | CF$_3$ | |
| 2.677 | 2-OCF$_3$ | H | H | —(CH$_2$)$_3$— | Cl | |

TABLE 2-continued

Compounds of formula

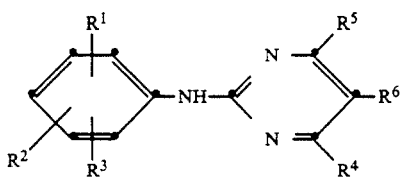

| Comp.No | R¹ | R² | R³ | R⁴ | | R⁶ | Phys. data |
|---|---|---|---|---|---|---|---|
| 2.678 | 2-OCF₃ | H | H | —(CH₂)₃— | | CF₃ | |
| 2.679 | 2-OCF₃ | H | H | —(CH₂)₄— | | Cl | |
| 2.680 | 2-OCF₃ | H | H | —(CH₂)₄— | | CF₃ | |
| 2.681 | 2-OCF₃ | 5-Cl | H | —(CH₂)₃— | | Cl | |
| 2.682 | 2-OCF₃ | 5-Cl | H | —(CH₂)₃— | | CF₃ | |
| 2.683 | 2-OCF₃ | 5-Cl | H | —(CH₂)₄— | | CF₃ | |
| 2.684 | 2-CH₃ | 5-Cl | H | —(CH₂)₃— | | Cl | |
| 2.685 | 2-CH₃ | 5-Cl | H | —(CH₂)₃— | | CF₃ | |
| 2.686 | 2-CH₃ | 5-Cl | H | —(CH₂)₄— | | Cl | |
| 2.687 | 2-CH₃ | 5-Cl | H | —(CH₂)₄— | | CF₃ | |
| 2.688 | 2-CN | H | H | —(CH₂)₃— | | CF₃ | |
| 2.689 | 2-CN | H | H | —(CH₂)₄— | | CF₃ | |
| 2.690 | 2-COOCH₃ | H | H | —(CH₂)₃— | | CF₃ | |
| 2.691 | 2-COOCH₃ | H | H | —(CH₂)₄— | | CF₃ | |
| 2.692 | 2-CH₃ | 2-CH₃ | H | —(CH₂)₄— | | Cl | |
| 2.693 | 2-CH₃ | 6-CH₃ | H | —(CH₂)₄— | | CF₃ | |
| 2.694 | 2-CH₃ | 6-CH₃ | H | —(CH₂)₃— | | CF₃ | m.p. 119° C. |
| 2.695 | 2-CH₃ | 6-C₂H₅ | H | —(CH₂)₃— | | CF₃ | |
| 2.696 | 2-CH₃ | 6-C₂H₅ | H | —(CH₂)₄— | | CF₃ | |
| 2.697 | 2-NO₂ | H | H | —(CH₂)₃— | | CH₃ | |
| 2.698 | 2-NO₂ | H | H | —(CH₂)₄— | | CH₃ | |
| 2.699 | 2-NO₂ | 6-CH₃ | H | —(CH₂)₃— | | CH₃ | |
| 2.700 | 2-NO₂ | 6-CH₃ | H | —(CH₂)₄— | | CH₃ | |

| Comp.No | R¹ | R² | R³ | R⁴ | R⁵ | R⁶ | Phys. data |
|---|---|---|---|---|---|---|---|
| 2.701 | 2-SCH₃ | H | H | CH₃ | CF₃ | CH₃ | |
| 2.702 | 2-SOCH₃ | H | H | CH₃ | CF₃ | CH₃ | |
| 2.703 | 2-SCHF₂ | H | H | CH₃ | CF₃ | CH₃ | |
| 2.704 | 2-SOCHF₂ | H | H | CH₃ | CF₃ | CH₃ | |
| 2.705 | 2-CHF₂ | H | H | C₂H₅ | CF₃ | CH₃ | |
| 2.706 | 2-CH₂F | H | H | CH₃ | CF₃ | CH₃ | |
| 2.707 | 2-CF₂CH₃ | H | H | CH₃ | CF₃ | CH₃ | |
| 2.708 | 2-CH₂CH₂CF₃ | H | H | CH₃ | CF₃ | CH₃ | |
| 2.709 | 2-CHClCHClCF₃ | H | H | CH₃ | CF₃ | CH₃ | |
| 2.710 | 2-OCF₂CHF₂ | H | H | CH₃ | CF₃ | CH₃ | |
| 2.711 | 2-OCF₂CHF₂ | 5-Cl | H | CH₃ | CF₃ | CH₃ | |
| 2.712 | 2-SCH₃ | 5-Cl | H | CH₃ | CF₃ | CH₃ | |
| 2.713 | 2-SO₂CH₃ | 5-Cl | H | CH₃ | CF₃ | CH₃ | |
| 2.714 | 2-SCHF₂ | 5-Cl | H | CH₃ | CF₃ | CH₃ | |
| 2.715 | 2-SO₂CHF₂ | 5-Cl | H | CH₃ | CF₃ | CH₃ | |
| 2.716 | 2-CF₂CF₃ | H | H | C₂H₅ | CF₃ | CH₃ | |
| 2.717 | 2-CF₂CF₃ | H | H | CH₃ | CF₃ | Cl | |
| 2.718 | 2-OCH₂CH₂Cl | H | H | CH₃ | CF₃ | CH₃ | |
| 2.719 | 2-OCH₂CH₂Cl | 5-Cl | H | C₂H₅ | CF₃ | CH₃ | |
| 2.720 | 2-COOCH₃ | 6-Cl | H | CH₃ | CF₃ | CH₃ | |
| 2.721 | 2-COOCH₃ | 6-Cl | H | C₂H₅ | CF₃ | CH₃ | |
| 2.722 | 2-COOC₂H₅ | 6-Cl | H | CH₃ | CF₃ | SCH₃ | |
| 2.723 | 2-COOCH₃ | 6-Cl | CH₃ | Cl | SCH₃ | | |
| 2.724 | 2-COOCH₃ | 6-Cl | H | CH₃ | Br | SCH₃ | |
| 2.725 | 2-COOCH₃ | 6-CH₃ | H | CH₃ | CF₃ | CH₃ | |
| 2.726 | 2-COOCH₃ | 6-CH₃ | H | CF₃ | Cl | CF₃ | |
| 2.727 | 2-COOC₃H₇(n) | 6-CH₃ | H | CH₃ | CF₃ | CH₃ | |
| 2.728 | 2-NO₂ | H | H | CH₃ | Br | Cl | |
| 2.729 | 2-NO₂ | 6-CH₃ | H | CF₃ | F | CH₃ | |
| 2.730 | 2-NO₂ | 6-CH₃ | H | CF₃ | Br | CH₃ | |
| 2.731 | 2-NO₂ | 6-CH₃ | H | CH₃ | F | CH₃ | |
| 2.732 | 2-NO₂ | 6-CH₃ | H | CH₃ | Br | CH₃ | |
| 2.733 | 2-NO₂ | 6-CH₃ | H | CH₃ | CF₃ | Cyclopentyl | |
| 2.734 | 2-NO₂ | 6-CH₃ | H | CH₃ | CF₃ | Cyclopropyl | |
| 2.735 | 2-NO₂ | H | H | CH₃ | CF₃ | Cyclohexyl | |
| 2.736 | 2-NO₂ | H | H | C₂H₅ | CF₃ | Cyclopentyl | |
| 2.737 | 2-Cl | 5-Cl | H | CH₃ | CF₃ | Cyclopentyl | |
| 2.738 | 2-NO₂ | H | H | Cyclopentyl | CF₃ | CH₃ | |
| 2.739 | 2-NO₂ | 6-CH₃ | H | Cyclopentyl | CF₃ | CH₃ | |
| 2.740 | 2-Cl | 5-Cl | H | Cyclopentyl | CF₃ | CH₃ | |
| 2.741 | 2-Cl | 5-Cl | H | Cyclohexyl | CF₃ | CH₃ | |
| 2.742 | 2-Cl | 5-Cl | H | Cyclohexyl | Cl | CH₃ | |
| 2.743 | 2-NO₂ | H | H | Cyclohexyl | CF₃ | CH₃ | |
| 2.744 | 2-NO₂ | 6-CH₃ | H | Cyclohexyl | CF₃ | CH₃ | |
| 2.745 | 2-NO₂ | H | H | SCHF₂ | CF₃ | CH₃ | |
| 2.756 | 2-NO₂ | H | H | SCF₃ | CF₃ | CH₃ | |
| 2.747 | 2-NO₂ | 6-CH₃ | H | SCHF₂ | CF₃ | CH₃ | |

TABLE 2-continued

Compounds of formula

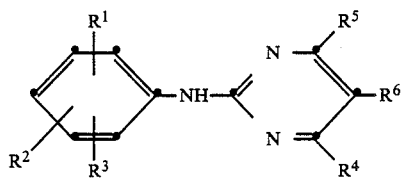

| Comp.No | $R^1$ | $R^2$ | $R^3$ | $R^5$ | $R^6$ | $R^4$ | Phys. data |
|---|---|---|---|---|---|---|---|
| 2.748 | 2-$NO_2$ | 6-$CH_3$ | H | SCHFCl | $CF_3$ | $CH_3$ | |
| 2.749 | 2-Cl | 5-Cl | H | $SCHF_2$ | $CF_3$ | $CH_3$ | |
| 2.750 | 2-Cl | 6-$CH_3$ | H | $SCHF_2$ | $CF_3$ | $CH_3$ | |
| 2.751 | 2-$NO_2$ | 6-$CH_3$ | H | Phenyl | $CF_3$ | $CH_3$ | |
| 2.752 | 2-$NO_2$ | 6-$CH_3$ | H | 4-Cl-Phenyl | $CF_3$ | $CH_3$ | |
| 2.753 | 2-$NO_2$ | 6-$CH_3$ | H | 2-Furyl | $CF_3$ | $CH_3$ | |
| 2.754 | 2-$NO_2$ | H | H | 2-Furyl | $CF_3$ | $CH_3$ | |
| 2.755 | 2-Cl | H | H | 2-Furyl | $CF_3$ | $CH_3$ | |

| Comp.No | $R^1$ | $R^2$ | $R^3$ | —$R^5$—$R^6$ | $R^4$ | Phys. data |
|---|---|---|---|---|---|---|
| 2.756 | 2-$NO_2$ | H | H | —$CH_2CH_2COCH_2$— | $CF_3$ | |
| 2.757 | 2-$NO_2$ | 6-$CH_3$ | H | —$CH_2CH_2COCH_2$— | $CF_3$ | |
| 2.758 | 2-$NO_2$ | H | H | —$CH_2CH_2CHClCH_2$— | $CF_3$ | |
| 2.759 | 2-$NO_2$ | 6-$CH_3$ | H | —$CH_2CH_2CHClCH_2$— | $CF_3$ | |
| 2.760 | 2-Cl | 5-Cl | H | —$CH_2CH_2CHClCH_2$— | $CF_3$ | |
| 2.761 | 2-Cl | 5-Cl | H | —$CH_2CH_2COCH_2$— | $CF_3$ | |
| 2.762 | 2-Cl | 5-Cl | H | —$CH_2CH_2COCH_2$— | $CF_3$ | |
| 2.763 | 2-$OCF_3$ | H | H | —$CH_2CH_2COCH_2$— | $CF_3$ | |
| 2.764 | 2-Cl | 6-$CH_3$ | H | —$CH_2CH_2COCH_2$— | $CF_3$ | |
| 2.765 | 2-$SCH_3$ | H | H | —$CH_2CH_2CH_2CH_2$— | $CF_3$ | |
| 2.766 | 2-$SCH_3$ | H | H | —$CH_2$—$CH_2CH_2$— | $CF_3$ | |
| 2.767 | 2-$SC_2H_5$ | H | H | —$CH_2$—$CH_2$—$CH_2$—$CH_2$— | $CF_3$ | |
| 2.768 | 2-$SOC_2H_5$ | H | H | —$CH_2$—$CH_2$—$CH_2$—$CH_2$— | $CF_3$ | |
| 2.769 | 2-$SCHF_2$ | H | H | —$CH_2$—$CH_2$—$CH_2$—$CH_2$— | $CF_3$ | |
| 2.770 | 2-$SOCHF_2$ | H | H | —$CH_2$—$CH_2$—$CH_2$—$CH_2$— | $CF_3$ | |
| 2.771 | 2-F | 6-Cl | H | —$CH_2$—$CH_2$—$CH_2$—$CH_2$— | $CF_3$ | m.p. 112–113° C. |
| 2.772 | 2-F | 6-Cl | H | —$CH_2$—$CH_2$—$CH_2$— | $CF_3$ | m.p. 147–148° C. |
| 2.773 | 2-$SOCH_3$ | 5-Cl | H | —$CH_2$—$CH_2$—$CH_2$—$CH_2$— | $CF_3$ | m.p. 194–195° C. |
| 2.774 | 2-$SCH_3$ | 5-Cl | H | —$(CH_2)_4$— | $CF_3$ | m.p. 123–124° C. |
| 2.775 | 2-$NO_2$ | 6-$CH_3$ | H | —$(CH_2)_6$— | $CF_3$ | m.p. 143–144° C. |
| 2.776 | 2-$NO_2$ | H | H | —$(CH_2)_4$— | $CF_2Cl$ | m.p. 111–112° C. |
| 2.777 | 2-$NO_2$ | 6-$CH_3$ | H | —$(CH_2)_2$—$CHCH_3$—$CH_2$ | $CF_3$ | m.p. 141–142° C. |
| 2.778 | 2-F | H | H | —$(CH_2)_4$— | $CF_3$ | m.p. 55–56° C. |
| 2.779 | 2-Cl | 6-Cl | 3-$CH_3$ | —$(CH_2)_4$— | $CF_3$ | m.p. 116–118° C. |
| 2.780 | 2-Cl | 6-Cl | 3-$CH_3$ | —$(CH_2)_3$— | $CF_3$ | m.p. 129–130° C. |
| 2.781 | 2-$NO_2$ | 6-F | H | —$(CH_2)_4$— | $CF_3$ | m.p. 109–110° C. |
| 2.782 | 2-$NO_2$ | 6-F | H | —$(CH_2)_3$— | $CF_3$ | m.p. 142–145° C. |
| 2.783 | 2-$OCH_3$ | 6-Cl | H | —$(CH_2)_4$— | $CF_3$ | m.p. 118–119° C. |
| 2.784 | 2-$OCH_3$ | 6-Cl | H | —$(CH_2)_3$— | $CF_3$ | m.p. 128–131° C. |
| 2.785 | 2-F | 6-F | H | —$(CH_2)_4$— | $CF_3$ | m.p. 120–121° C. |
| 2.786 | 2-F | 6-F | H | —$(CH_2)_4$— | $CF_2Cl$ | semicristalline |
| 2.787 | 2-F | 6-F | H | —$(CH_2)_4$— | $CHF_2$ | m.p. 128–129° C. |
| 2.788 | 2-$CH_3$ | 5-F | H | —$(CH_2)_4$— | $CF_3$ | m.p. 88–89° C. |
| 2.789 | 2-Br | 6-Br | H | —$(CH_2)_4$— | $CF_3$ | m.p. 167–169° C. |
| 2.790 | 2-$CH_3$ | 6-$CH_3$ | H | —$(CH_2)_4$— | $CHF_2$ | m.p. 97–101° C. |
| 2.791 | 2-$NO_2$ | H | H | —$(CH_2)_3$— | $CF_2Cl$ | m.p. 118–119° C. |
| 2.792 | 2-$NO_2$ | H | H | —$(CH_2)_3$— | $CHF_2$ | m.p. 146–147° C. |
| 2.793 | 2-Cl | 5-Cl | H | —$(CH_2)_3$— | $CHF_2$ | m.p. 130–132° C. |
| 2.794 | 2-F | 6-Cl | H | —$(CH_2)_3$— | $CHF_2$ | m.p. 129–131° C. |
| 2.795 | 2-$SCHF_2$ | H | H | —$(CH_2)_3$— | $CF_3$ | m.p. 109–110° C. |
| 2.796 | 2-$OCHF_2$ | 6-$CH_3$ | H | —$(CH_2)_4$— | m.p. 79–80° C. | m.p. 109–110° C. |
| 2.797 | 2-F | 6-F | H | —$(CH_2)_3$— | $CHF_2$ | m.p. 114–115° C. |

| Comp.No | $R^1$ | $R^2$ | $R^3$ | $R^4$ | $R^5$ | $R^6$ | Phys. data |
|---|---|---|---|---|---|---|---|
| 2.798 | 2-$NO_2$ | H | H | Cl | $CF_3$ | $CH_3$ | m.p. 122–123° C. |
| 2.799 | 2-$CH_3$ | 6-Cl | H | Cl | $CF_3$ | $CH_3$ | m.p. 99–100° C. |
| 2.800 | 2-$NO_2$ | H | H | $CF_3$ | $OC_2H_5$ | $CH_3$ | m.p. 117–118° C. |
| 2.801 | 2-$NO_2$ | H | H | $CF_3$ | Cl | $OCH_3$ | m.p. 97–98° C. |

Biological Examples

Example B1: Pre-emergence herbicidal action

In a greenhouse, immediately after sowing the test plants in seed trays the surface of the soil is treated with an aqueous spray mixture corresponding to a rate of application of 4 kg of active ingredient/hectare. The seed trays are kept in the greenhouse at 22°–25° C. and 50–70% relative humidity.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action. Ratings of 6 to 9 (especially 7 to 9) indicate a good tolerance (especially in the case of crop plants).

Results of this test are compiled in Table 3

TABLE 3

| Comp. No. | Setaria italica | Stellaria media |
|---|---|---|
| 1.058 | 2 | 2 |
| 1.284 | 1 | 2 |
| 1.340 | 2 | 2 |
| 1.449 | 1 | 2 |
| 1.496 | 1 | 1 |
| 1.512 | 2 | 4 |
| 1.545 | 1 | 1 |
| 1.548 | 2 | 1 |
| 1.577 | 2 | 1 |
| 1.627 | 1 | 2 |
| 1.642 | 2 | 1 |
| 1.672 | 2 | 2 |
| 1.772 | 1 | 1 |

Example B2: Pre-emergence herbicidal action (selective herbicidal, action)

Immediately after the test plants have been sawn into beakers with 12 to 15 cm diameter the covering soil was treated with an aqueous formulation containing the active ingredient according to an application rate of 1000 and 500 [g]AS/[ha].

The beakers were kept in a greenhouse at temperatures between 22° and 25° C. and a rel. humidity of 50 to 70%.

After 3 weeks the herbicidal action is assessed in comparison with an untreated control group using a nine-stage evaluation scale (1=total damage, 9=no effect).

Ratings of 1 to 4 (especially 1 to 3) indicate a good to very good herbicidal action. Ratings of 6 to 9 (especially 7 to 9) indicate a good tolerance (especially in case of crop plants).

In this experiment inter alia compounds 1.284, 1.545, 1.563, 1.627 and 1.782 show good to very good tolerance in barley, maize, soya, cotton or rape with good herbicidal activity inter alia against Solanum nigrum, Galium aparine and Veronica sp.

Example B3: Herbicidal action in paddy

The water weeds Echinochloa crus galli and Monocharia vag. are sown in plastics beakers (60 cm² surface area, 500 ml volume). After sowing, the beakers are filled to the soil surface with water. 3 days after sowing, the water level is raised to slightly above (3–5 mm) the surface of the soil. Application is carried out 3 days after sowing by spraying the test substances onto the vessels. The dose which is used corresponds to a quantity of active ingredient of 4 kg per hectare. The plant beakers are then placed in a greenhouse under optimum growth conditions for the rice weeds, i.e. at 25°–30° C. and high humidity.

The tests are evaluated 3 weeks after the application. The compounds of Table 1 damage the weeds but not the rice.

Example B4: Growth inhibition in grasses with trefoil

A mixture of grasses (for example Poa, Festuca, Lolium, Bromus, Cynosurus) and trefoil (Trifolium pratense/repens) is sown in 15 cm plastics pots containing sterile soil and cultivated in a greenhouse at a daytime temperature of 21° C. and a night time temperature of 17° C. The illumination time is 13.5 hours/day at a light intensity of at least 7000 Lux. After emergence the plants are cut back weekly to a height of approximately 6 cm. Approximately 42 days after sowing and 1 day after the last cut, 0.3 to 3 kg of active ingredient/hectare are applied, generally in a 25% strength formulation in an aqueous spray mixture. The amount of water applied is approximately 500 /1 ha.

Evaluation is carried out approximately 3 weeks after the treatment. At this point the height of the new growth is measured. The compounds of Table 1 tested cause a reduction in new growth compared with the untreated control.

Example B5: Growth inhibition in cereals

The plants (for example summer barley of the Iban variety) are sown in 15 cm plastics pots containing sterilised soil and cultivated in a climatic chamber at a daytime temperature of 10°–15° C. and a night time temperature of 5°–10° C. The illumination time is 13.5 hours.

Approximately 34 days after sowing and after thinning out to 4 plants per pot, 0.3 to 3 kg of active ingredient/ha, generally as a 25 % strength formulation in an aqueous spray mixture, are applied. The amount of water applied is approximately 500 l/ha. After the application the plants are placed in a greenhouse at a daytime temperature of at least 10° C. The illumination time is at least 13.5 hours/day.

The evaluation is carried out approximately 28 days after the treatment. At this point the height of the new growth is measured. The compounds of Table 1 tested cause a reduction in new growth compared with the untreated control.

Example B6: Growth inhibition in grasses

The grasses Lolium perenne, Poa pratensis, Festuca ovina, Dactylis glomerata and Cynodon dactylon are sown in a greenhouse in plastics trays containing a soil/peat/sand mixture (6:3:1) and watered as required. The emerged grasses are cut back weekly to a height of 4 cm and, about 50 days after sowing and one day after the last cut, sprayed with an aqueous spray mixture of an active ingredient from Table 1. The quantity of active ingredient is equivalent to up to 500 g of active ingredient per hectare. 21 days after application, the growth of the grasses is assessed.

The compounds of Table 1 tested cause a reduction in the new groth compared with the untreated control.

Formulation Examples

Example F1: Formulation Examples for active ingredients of formula I, (throughout, percentages are by weight)

| (a) Emulsifiable concentrates | (a) | (b) | (c) |
|---|---|---|---|
| a compound according to Table 1 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) |
|---|---|---|---|
| a compound according to Table 1 | 80% | 10% | 5% |
| ethylene glycol monomethyl ether | 20% | — | — |

-continued

| (b) Solutions | (a) | (b) | (c) |
|---|---|---|---|
| polyethylene glycol MW 400 | — | 70% | — |
| N-methyl-2-pyrrolidone | — | 20% | 5% |
| epoxidised coconut oil | — | — | 90% |

These solutions are suitable for application in the form of micro-drops.

| (c) Granulates | (a) | (b) |
|---|---|---|
| a compound according to Table 1 | 5% | 10% |
| kaolin | 94% | — |
| highly dispersed silicic acid | 1% | — |
| attapulgite | — | 90% |

A solution of the active ingredient is sprayed onto the carrier, and the solvent is subsequently evaporated off in vacuo.

| (d) Dusts | (a) | (b) |
|---|---|---|
| a compound according to Table 1 | 2% | 5% |
| highly dispersed silicic acid | 1% | 5% |
| talcum | 97% | — |
| kaolin | — | 90% |

Ready-for-use dusts are obtained by homogeneously mixing the carriers with the active ingredient.

| (e) Wettable powders | (a) | (b) |
|---|---|---|
| a compound according to Table 1 | 20% | 60% |
| sodium lignosulfonate | 5% | 5% |
| sodium lauryl sulfate | — | 6% |
| octylphenol polyethylene glycol ether (7-8 moles of ethylene oxide) | — | 2% |
| highly dispersed silicic acid | 5% | 27% |
| kaolin | 70% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| an compound according to Table 1 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (g) Coated granulate | |
|---|---|
| a compound according to Table 1 | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound according to Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | ad 100% |

The active ingredient is intimately mixed with the adjuvants, giving a suspension concentrate from which suspensions of any desired concentration can be obtained by dilution with water.

What is claimed is:

1. An urea of formula I

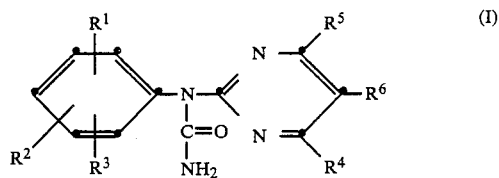

in which
R$^1$, R$^2$ and R$^3$ are each, independently of the others, hydrogen; nitro; cyano; halogen; C$_1$-C$_4$alkyl; C$_1$-C$_4$-alkyl-S(O)$_n$; C$_1$-C$_4$alkoxy; C$_1$-C$_4$haloalkyl; C$_1$-C$_4$haloalkoxy; C$_1$-C$_4$haloalkyl-S(O)$_n$; C$_1$-C$_4$alkoxycarbonyl; C$_1$-C$_4$alkylcarbonyl; aminocarbonyl; mono-C$_1$-C$_4$alkylaminocarbonyl; or di-C$_1$-C$_4$alkylaminocarbonyl;

R$^4$ and R$^5$ are each, independently of the other, hydrogen; C$_1$-C$_4$alkyl; C$_1$-C$_4$alkoxy; C$_1$-C$_4$alkyl-S(O)$_n$; C$_1$-C$_4$haloalkyl; C$_1$-C$_4$haloalkoxy; C$_1$-C$_4$haloalkyl-S(O)$_n$; phenyl that is unsubstituted or is substituted by up to three identical or different substituents from C$_1$-C$_4$alkyl, halogen, C$_1$-C$_4$alkoxy, C$_1$-C$_4$haloalkyl, nitro and cyano; furanyl; thiophenyl; C$_3$-C$_6$cycloalkyl; C$_1$-C$_4$-alkoxycarbonyl; C$_1$-C$_4$alkoxy-C$_1$-C$_4$alkyl; C$_1$-C$_4$alkoxycarbonyl-C$_1$-C$_4$alkyl; C$_1$-C$_4$alkylcarbonyl-C$_1$-C$_4$alkyl; C$_3$-C$_4$alkenyloxycarbonyl-C$_1$-C$_4$alkyl; C$_3$-C$_4$alkynyloxycarbonyl-C$_1$-C$_4$alkyl; halogen; or cyano;

R$^6$ is C$_1$-C$_4$alkyl; halogen; cyano; C$_3$-C$_6$cycloalkyl; C$_1$-C$_4$haloalkyl; C$_1$-C$_4$alkoxy; nitro; C$_1$-C$_4$alkyl-S(O)$_n$; C$_1$-C$_4$haloalkoxy; C$_1$-C$_4$haloalkyl-S(O)$_n$; or phenyl that is unsubstituted or is substituted by up to three identical or different substituents from halogen, C$_1$-C$_4$alkyl, C$_1$-C$_4$haloalkyl, C$_1$-C$_4$alkyl-S(O)$_n$, C$_1$-C$_4$alkoxy, C$_1$-C$_4$haloalkoxy, nitro and cyano; or C$_1$-C$_4$alkylthio-C$_1$-C$_4$alkyl;

n is 0, 1 or 2; or

R$^5$ and R$^6$, together with the two carbon atoms to which they are bonded, are a fused, partially unsaturated, 4- to 8-membered ring which may be substituted by up to three identical or different substituents from C$_1$-C$_4$alkyl, halogen and C$_1$-C$_4$alkoxycarbonyl and/or is interrupted by O, S or N-(C$_1$-C$_4$)-alkyl and/or may contain a double bond and/or a carbonyl group;

including the salts thereof with acids, bases and complex formers.

2. An urea according to claim 1 in which $R^1$ is hydrogen; nitro; cyano; halogen; $C_1$-$C_3$alkyl; $C_1$-$C_2$-alkyl-S(O)$_n$; $C_1$-$C_2$haloalkyl-S(O)$_n$; $C_1$-$C_3$alkoxy; $C_1$-$C_3$haloalkyl; $C_1$-$C_2$-haloalkoxy; $C_1$-$C_3$alkoxycarbony; or dimethylaminocarbonyl;

$R^2$ is hydrogen; nitro; fluorine; chlorine; bromine; or $C_1$-$C_3$-alkyl;

$R^3$ is hydrogen; chlorine; or $C_1$-$C_3$alkyl;

$R^4$ is hydrogen; $C_1C_4$alkyl; $C_1$-$C_3$alkoxy; $C_1$-$C_4$alkyl-S(O)$_n$-; $C_1$-$C_3$haloalkyl; $C_1$-$C_2$haloalkoxy; phenyl; chlorophenyl; furanyl; $C_3$-$C_6$cycloalkyl; $C_1$-$C_4$alkoxycarbonyl-$C_1$-$C_2$alkyl; $C_1$-$C_2$alkoxy-$C_1$-$C_2$alkyl; $C_1$-$C_2$haloalkylthio; chlorine; cyano; or acetonyl;

$R^5$ is hydrogen; $C_1$-$C_3$alkyl; $C_1$-$C_3$alkoxy; halogen; $C_1$-$C_3$haloalkyl; or $C_1$-$C_3$haloalkoxy;

$R^6$ is $C_1$-$C_3$alkyl; $C_1$-$C_3$alkoxy; $C_1$-$C_3$haloalkyl; $C_1$-$C_3$haloalkoxy; chlorine, bromine; $C_1$-$C_3$alkylthio; cyano; nitro; $C_1$-$C_2$alkoxy-$C_1$-$C_2$alkyl; phenyl; chlorophenyl; $C_1$-$C_3$alkoxycarbonyl; $C_1$-$C_2$alkylthio-$C_1$-$C_2$alkyl; or $C_3$-$C_6$cycloalkyl;

n is 0, 1 and 2;

$R^5$ and $R^6$ together are a —CH$_2$CH$_2$—, —CH$_2$—CH$_2$—CH$_2$—, —CH$_2$—CH$_2$—CH$_2$—CH$_2$—, —CH$_2$—CH$_2$—CO—CH$_2$—, —CH═CH—CH$_2$—, —CH═CH—CH$_2$—CH$_2$—, —O—CH$_2$—CH$_2$—CH$_2$—, —CH$_2$—CH$_2$—S. —CH$_2$—CH$_2$—S—CH$_2$—, —O—CH$_2$—CH$_2$—, —(CH$_2$)$_5$—, —(CH$_2$)$_6$—, —CH$_2$—CH$_2$—CH$_2$—O—, —CH$_2$—CH$_2$—O—, —CH$_2$—CH$_2$—O—CH$_2$— or, each of which is unsubstituted or is substituted by up to three $C_1$-$C_3$alkyl radicals or by one methoxy or one $C_1$-$C_3$alkoxycarbonyl radical or one chlorine atom.

3. An urea according to claim 1 of formula Ia

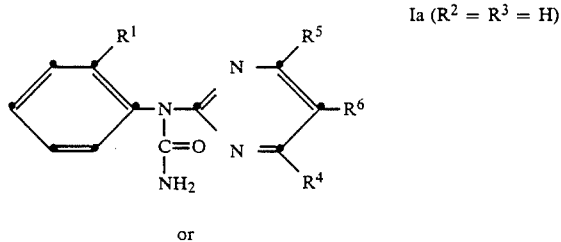

Ia ($R^2 = R^3$ = H)

or

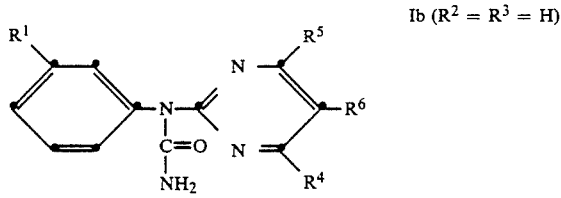

Ib ($R^2 = R^3$ = H)

wherein $R^2$ and $R^3$ is hydrogen.

4. An urea according to claim 1 of formula Ic, Id, Ie or If

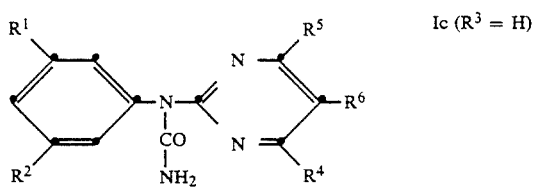

Ic ($R^3$ = H)

-continued

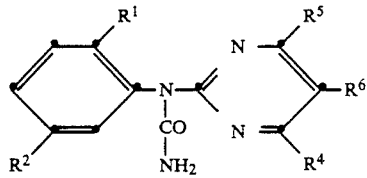

Id ($R^3$ = H)

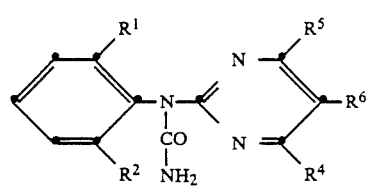

Ie ($R^3$ = H)

or

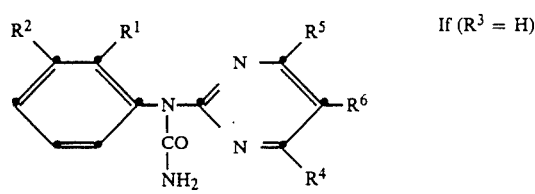

If ($R^3$ = H)

wherein $R^3$ is hydrogen.

5. An urea according to claim 1 of formula Ig

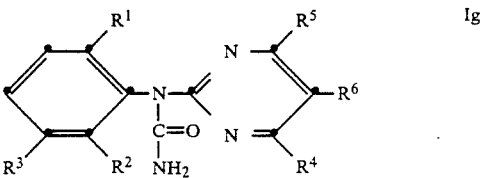

Ig

6. An aniline of formula II according to claim 1 in which $R^1$ to $R^4$ are as defined hereinbefore and $R^5$ and $R^6$, together with the two carbon atoms to which they are bonded, are a fused, partially unsaturated, 4- to 8-membered ring which may be substituted by up to three identical or different substituents from $C_1$-$C_4$alkyl, halogen and $C_1$-$C_4$alkoxycarbonyl and/or is interrupted by O, S or N-($C_1$-$C_4$)-alkyl and/or may contain a double bond and/or a carbonyl group.

7. A carbamoyl chloride of formula III

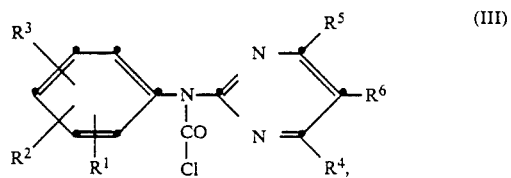

(III)

in which the radicals $R^1$ to $R^6$ are as defined in claim 1.

8. An urea of formula IV

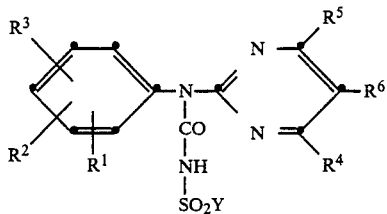

in which the radicals $R^1$ to $R^6$ are as defined in claim 1 and Y is halogen.

9. A herbicidal composition comprising as active ingredient a compound of formula I according to claim 1 and a carrier.

10. A plant growth-regulating composition comprising as active ingredient a compound of formula I according to claim 1 and a carrier.

11. A method of controlling undesired plant growth which comprises allowing to act upon the plant to be controlled or the locus thereof a herbicidally effective amount of a compound according to claim 1 or a composition according to claim 9.

12. A method according to claim 11 for the pre- or post-emergence control of undesired plant growth in crops of useful plants.

13. A method of influencing plant growth which comprises allowing to act upon the plant or the locus thereof an amount of a compound according to claim 1, or of a composition according to claim 10, that is effective in plant growth regulation.

14. A method for regulating the growth of intersown plants in maize or for regulating the growth of grasses which comprises allowing to act upon the intersown plants or grasses an amount of a compound according to claim 1 that is effective in plant growth regulation.

15. An aniline of the formula II

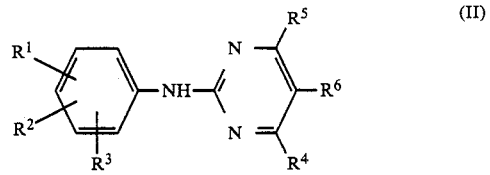

in which the radicals $R^1$ to $R^6$ are as defined in claim 1.

* * * * *